US008546337B2

(12) United States Patent
Burkhard

(10) Patent No.: US 8,546,337 B2
(45) Date of Patent: Oct. 1, 2013

(54) SELF-ASSEMBLING PEPTIDE NANOPARTICLES USEFUL AS VACCINES

(75) Inventor: Peter Burkhard, Mansfield Center, CT (US)

(73) Assignee: Alpha-O-Peptides AG, Riehen (CH)

( * ) Notice: Subject to any disclaimer, the term of this patent is extended or adjusted under 35 U.S.C. 154(b) by 261 days.

(21) Appl. No.: 12/864,576

(22) PCT Filed: Jan. 29, 2009

(86) PCT No.: PCT/EP2009/050996
§ 371 (c)(1), (2), (4) Date: Jul. 26, 2010

(87) PCT Pub. No.: WO2009/109428
PCT Pub. Date: Sep. 11, 2009

(65) Prior Publication Data
US 2011/0020378 A1 Jan. 27, 2011

(30) Foreign Application Priority Data
Feb. 1, 2008 (EP) .................................... 08101221

(51) Int. Cl.
*A61K 38/00* (2006.01)
*A61K 39/00* (2006.01)
*C07K 14/00* (2006.01)
*C07K 2/00* (2006.01)

(52) U.S. Cl.
USPC ........ 514/21.3; 514/1.1; 424/184.1; 530/300; 530/350

(58) Field of Classification Search
None
See application file for complete search history.

(56) References Cited

U.S. PATENT DOCUMENTS

| | | | |
|---|---|---|---|
| 6,756,039 B1 * | 6/2004 | Yeates et al. ............... | 424/192.1 |
| 6,783,761 B2 * | 8/2004 | Grimes et al. ............. | 424/185.1 |
| 2007/0014804 A1 * | 1/2007 | Burkhard ................... | 424/184.1 |

FOREIGN PATENT DOCUMENTS

| | | |
|---|---|---|
| WO | 94/26903 | 11/1994 |
| WO | 01/00010 | 1/2001 |
| WO | 02/100325 | 12/2002 |
| WO | 03/045415 | 6/2003 |
| WO | 2004/071493 | 8/2004 |
| WO | 2006/033679 | 3/2006 |

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*

"Designing Custom Peptides," from SIGMA Genosys, pp. 1-2. Accessed Dec. 16, 2004.*

Schinzel R, Drueckes P, "The phosphate recognition site of *Escherichia coli* maltodextrin phosphorylase," FEBS, Jul. 1991, 286(1,2): 125-128.*

Berendsen HJC, "A Glimpse of the Holy Grail?" Science, 1998, 282: 642-643.*

Voet D, Voet JG, Biochemistry, Second Edition, John Wiley & Sons, Inc., 1995, pp. 235-241.*

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*

International Search Report issued Feb. 16, 2010 in International (PCT) Application No. PCT/EP2009/050996 along with the Written Opinion.

M. Wang et al., "CTL Epitopes for Influenza A Including the H5N1 Bird Flu; Genome-, Pathogen-, and HLA-Wide Screening", Vaccine, vol. 25, No. 15, pp. 2823-2831, Apr. 12, 2007.

S. Raman et al., "Structure-Based Design of Peptides that Self-Assemble into Regular Polyhedral Nanoparticles", Nanomedicine: Nanotechnology, Biology and Medicine, vol. 2, pp. 95-102, Jan. 1, 2006.

J. A. Cooper et al., "Mapping of Conformational β Cell Epitopes within Alpha-Helical Coiled Coil Proteins", Molecular Immunology, vol. 34, No. 6, pp. 433-440, Jan. 1, 1997.

T. Pimentel et al., "Peptide Nanoparticles as Novel Immunogens: Design and Analysis of a Prototypic Severe Acute Respiratory Syndrome Vaccine", Chemical Biology & Drug Design, vol. 73, No. 1, pp. 53-61, Dec. 18, 2008.

* cited by examiner

*Primary Examiner* — Julie Ha

(74) *Attorney, Agent, or Firm* — Wenderoth, Lind & Ponack, L.L.P.

(57) ABSTRACT

Self-assembling peptide nanoparticles (SAPN) incorporating T-cell epitopes and/or B-cell epitopes are described. The nanoparticles of the invention consist of aggregates of a continuous peptidic chain comprising two oligomerization domains connected by a linker segment wherein one or both oligomerization domains incorporate T-cell epitopes and/or B-cell epitopes within their peptide sequence. These nanoparticles are useful as vaccines and adjuvants.

6 Claims, 7 Drawing Sheets

A

B

A (P5c-6-CSP)

A (T1c-7-CSP)

A (BN5c-M2eN-CTL)

B (BN5c-M2eN-ctl_CH)

A (T811c-9-Pf)

SEQUENCE LISTING

```
<160> NUMBER OF SEQ ID NOS: 296

<210> SEQ ID NO 1
<211> LENGTH: 44
<212> TYPE: PRT
<213> ORGANISM: Artificial sequence
<220> FEATURE:
<223> OTHER INFORMATION: Synthetic construct; pentamerization domain
      of COMP

<400> SEQUENCE: 1

Leu Ala Pro Gln Met Leu Arg Glu Leu Gln Glu Thr Asn Ala Ala Leu
1               5                   10                  15

Gln Asp Val Arg Glu Leu Leu Arg Gln Gln Val Lys Gln Ile Thr Phe
            20                  25                  30

Leu Lys Asn Thr Val Met Glu Cys Asp Ala Cys Gly
        35                  40


<210> SEQ ID NO 2
<211> LENGTH: 53
<212> TYPE: PRT
<213> ORGANISM: Artificial sequence
<220> FEATURE:
<223> OTHER INFORMATION: Synthetic construct; pentamerization domain
      of tryptophan zipper

<400> SEQUENCE: 2

Ser Ser Asn Ala Lys Trp Asp Gln Trp Ser Ser Asp Trp Gln Thr Trp
1               5                   10                  15

Asn Ala Lys Trp Asp Gln Trp Ser Asn Asp Trp Asn Ala Trp Arg Ser
            20                  25                  30

Asp Trp Gln Ala Trp Lys Asp Asp Trp Ala Arg Trp Asn Gln Arg Trp
        35                  40                  45

Asp Asn Trp Ala Thr
    50


<210> SEQ ID NO 3
<211> LENGTH: 27
<212> TYPE: PRT
<213> ORGANISM: Artificial sequence
<220> FEATURE:
<223> OTHER INFORMATION: Synthetic construct; trimerization domain
      of T4 protein fibritin

<400> SEQUENCE: 3

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25


<210> SEQ ID NO 4
<211> LENGTH: 59
<212> TYPE: PRT
<213> ORGANISM: Artificial sequence
```

<220> FEATURE:
<223> OTHER INFORMATION: Synthetic construct; T4 protein fibritin

<400> SEQUENCE: 4

Val Gln Asn Leu Gln Val Glu Ile Gly Asn Asn Ser Ala Gly Ile Lys
1 5 10 15

Gly Gln Val Val Ala Leu Asn Thr Leu Val Asn Gly Thr Asn Pro Asn
20 25 30

Gly Ser Thr Val Glu Glu Arg Gly Leu Thr Asn Ser Ile Lys Ala Asn
35 40 45

Glu Thr Asn Ile Ala Ser Val Thr Gln Glu Val
50 55

<210> SEQ ID NO 5
<211> LENGTH: 53
<212> TYPE: PRT
<213> ORGANISM: Artificial sequence
<220> FEATURE:
<223> OTHER INFORMATION: Synthetic construct; V3 epitope of gp120 HIV incorporated into fibritin trimerization domain

<400> SEQUENCE: 5

Leu Glu Glu Leu Glu Arg Arg Leu Glu Glu Leu Glu Arg Arg Leu Glu
1 5 10 15

Glu Leu Glu Arg Arg Leu Gly Ser Ile Arg Ile Gly Pro Gly Gln Thr
20 25 30

Phe Tyr Ala Gly Val Asp Leu Glu Leu Ala Ala Leu Arg Arg Arg Leu
35 40 45

Glu Glu Leu Ala Arg
50

<210> SEQ ID NO 6
<211> LENGTH: 17
<212> TYPE: PRT
<213> ORGANISM: Artificial sequence
<220> FEATURE:
<223> OTHER INFORMATION: Synthetic construct; ER targeting signal E3/19K

<400> SEQUENCE: 6

Met Arg Tyr Met Ile Leu Gly Leu Leu Ala Leu Ala Ala Val Cys Ser
1 5 10 15

Ala

<210> SEQ ID NO 7
<211> LENGTH: 46
<212> TYPE: PRT
<213> ORGANISM: Artificial sequence
<220> FEATURE:
<223> OTHER INFORMATION: Synthetic construct; coiled coil trimerization domain incorporating PADRE

<400> SEQUENCE: 7

Arg Leu Leu Ala Arg Leu Glu Glu Leu Glu Arg Arg Leu Glu Glu Leu
1 5 10 15

Ala Lys Phe Val Ala Ala Trp Thr Leu Lys Ala Ala Ala Val Asp Leu
20 25 30

Glu Leu Ala Ala Leu Arg Arg Arg Leu Glu Glu Leu Ala Arg
35 40 45

<210> SEQ ID NO 8
<211> LENGTH: 127
<212> TYPE: PRT
<213> ORGANISM: Artificial sequence
<220> FEATURE:
<223> OTHER INFORMATION: Synthetic construct; building block comprising His tag, COMP, PADRE and CS protein

<400> SEQUENCE: 8

```
Met Gly His His His His His His Gly Asp Trp Lys Trp Asp Gly Gly
1               5                   10                  15

Leu Val Pro Arg Gly Ser Asp Glu Met Leu Arg Glu Leu Gln Glu Thr
            20                  25                  30

Asn Ala Ala Leu Gln Asp Val Arg Glu Leu Leu Arg Gln Gln Val Lys
        35                  40                  45

Gln Ile Thr Phe Leu Arg Ala Leu Leu Met Gly Gly Arg Leu Leu Ala
    50                  55                  60

Arg Leu Glu Glu Leu Glu Arg Arg Leu Glu Glu Leu Ala Lys Phe Val
65                  70                  75                  80

Ala Ala Trp Thr Leu Lys Ala Ala Ala Val Asp Leu Glu Leu Ala Ala
                85                  90                  95

Leu Arg Arg Arg Leu Glu Glu Leu Ala Arg Gly Gly Ser Gly Asp Pro
            100                 105                 110

Pro Pro Pro Asn Pro Asn Asp Pro Pro Pro Pro Asn Pro Asn Asp
        115                 120                 125
```

<210> SEQ ID NO 9
<211> LENGTH: 46
<212> TYPE: PRT
<213> ORGANISM: Artificial sequence
<220> FEATURE:
<223> OTHER INFORMATION: Synthetic construct; coiled coil P5c-6 with overlapping HTL epitopes

<400> SEQUENCE: 9

```
Arg Leu Leu Ala Arg Leu Glu Glu Leu Glu Arg Ser Ile Trp Met Leu
1               5                   10                  15

Gln Gln Ala Ala Ala Arg Leu Glu Arg Ala Ile Asn Thr Val Asp Leu
            20                  25                  30

Glu Leu Ala Ala Leu Arg Arg Arg Leu Glu Glu Leu Ala Arg
        35                  40                  45
```

<210> SEQ ID NO 10
<211> LENGTH: 127
<212> TYPE: PRT
<213> ORGANISM: Artificial sequence
<220> FEATURE:
<223> OTHER INFORMATION: Synthetic construct; building block with His tag, COMP, overlapping HTL epitopes and CS protein

<400> SEQUENCE: 10

```
Met Gly His His His His His His Gly Asp Trp Lys Trp Asp Gly Gly
1               5                   10                  15

Leu Val Pro Arg Gly Ser Asp Glu Met Leu Arg Glu Leu Gln Glu Thr
            20                  25                  30

Asn Ala Ala Leu Gln Asp Val Arg Glu Leu Leu Arg Gln Gln Val Lys
        35                  40                  45

Gln Ile Thr Phe Leu Arg Ala Leu Leu Met Gly Gly Arg Leu Leu Ala
    50                  55                  60

Arg Leu Glu Glu Leu Glu Arg Ser Ile Trp Met Leu Gln Gln Ala Ala
65                  70                  75                  80

Ala Arg Leu Glu Arg Ala Ile Asn Thr Val Asp Leu Glu Leu Ala Ala
                85                  90                  95

Leu Arg Arg Arg Leu Glu Glu Leu Ala Arg Gly Gly Ser Gly Asp Pro
```

100 105 110

Pro Pro Pro Asn Pro Asn Asp Pro Pro Pro Pro Asn Pro Asn Asp
115 120 125

<210> SEQ ID NO 11
<211> LENGTH: 46
<212> TYPE: PRT
<213> ORGANISM: Artificial sequence
<220> FEATURE:
<223> OTHER INFORMATION: Synthetic construct; coiled coil with HTL epitopes from influenza

<400> SEQUENCE: 11

Arg Leu Leu Ala Arg Leu Glu Glu Ile Arg His Glu Asn Arg Met Val
1 5 10 15

Leu Tyr Lys Ile Phe Lys Ile Glu Lys Gly Ile Asn Thr Val Asp Leu
20 25 30

Glu Leu Ala Ala Leu Arg Arg Arg Leu Glu Glu Leu Ala Arg
35 40 45

<210> SEQ ID NO 12
<211> LENGTH: 128
<212> TYPE: PRT
<213> ORGANISM: Artificial sequence
<220> FEATURE:
<223> OTHER INFORMATION: Synthetic construct; building block with His tag, Trp zipper, HTL epitopes from influenza and CS protein

<400> SEQUENCE: 12

Met Gly His His His His His His Gly Asp Trp Lys Trp Asp Gly Gly
1 5 10 15

Leu Val Pro Arg Gly Ser Trp Gln Thr Trp Asn Ala Lys Trp Asp Gln
20 25 30

Trp Ser Asn Asp Trp Asn Ala Trp Arg Ser Asp Trp Gln Ala Trp Lys
35 40 45

Asp Asp Trp Ala Arg Trp Arg Ala Leu Trp Met Gly Gly Arg Leu Leu
50 55 60

Ala Arg Leu Glu Glu Ile Arg His Glu Asn Arg Met Val Leu Tyr Lys
65 70 75 80

Ile Phe Lys Ile Glu Lys Gly Ile Asn Thr Val Asp Leu Glu Leu Ala
85 90 95

Ala Leu Arg Arg Arg Leu Glu Glu Leu Ala Arg Gly Gly Ser Gly Asp
100 105 110

Pro Pro Pro Pro Asn Pro Asn Asp Pro Pro Pro Pro Asn Pro Asn Asp
115 120 125

<210> SEQ ID NO 13
<211> LENGTH: 85
<212> TYPE: PRT
<213> ORGANISM: Artificial sequence
<220> FEATURE:
<223> OTHER INFORMATION: Synthetic construct; trimeric coiled coil with cancer CTL epitope

<400> SEQUENCE: 13

Trp Gln Thr Trp Asn Ala Lys Trp Asp Gln Trp Ser Asn Asp Trp Asn
1 5 10 15

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

```
Glu Arg Arg Leu Glu Met Leu Leu Ala Tyr Leu Tyr Gln Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 14
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 14

Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Arg Leu Glu Glu Leu Leu Asp Gly Thr Ala Thr Leu Arg Leu
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 15
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 15

Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Arg Leu Leu Ile Tyr Arg Arg Arg Leu Met Lys Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 16
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 16

Trp Gln Thr Trp Asn Ala Lys Trp Asp Gln Trp Ser Asn Asp Trp Asn
1               5                   10                  15
```

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

Glu Arg Arg Leu Glu Ile Leu Thr Val Ile Leu Gly Val Leu Glu Arg
50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 17
<211> LENGTH: 85
<212> TYPE: PRT
<213> ORGANISM: Artificial sequence
<220> FEATURE:
<223> OTHER INFORMATION: Synthetic construct; trimeric coiled coil with cancer CTL epitope

<400> SEQUENCE: 17

Trp Gln Thr Trp Asn Ala Lys Trp Asp Gln Trp Ser Asn Asp Trp Asn
1 5 10 15

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

Glu Arg Glu Leu Ala Gly Ile Gly Ile Leu Thr Val Glu Leu Glu Arg
50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 18
<211> LENGTH: 85
<212> TYPE: PRT
<213> ORGANISM: Artificial sequence
<220> FEATURE:
<223> OTHER INFORMATION: Synthetic construct; trimeric coiled coil with cancer CTL epitope

<400> SEQUENCE: 18

Trp Gln Thr Trp Asn Ala Lys Trp Asp Gln Trp Ser Asn Asp Trp Asn
1 5 10 15

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

Glu Arg Arg Met Ser Leu Gln Arg Gln Phe Leu Arg Glu Leu Glu Arg
50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 19
<211> LENGTH: 85
<212> TYPE: PRT
<213> ORGANISM: Artificial sequence
<220> FEATURE:

<223> OTHER INFORMATION: Synthetic construct; trimeric coiled coil with
cancer CTL epitope

<400> SEQUENCE: 19

```
Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Arg Leu Glu Lys Ile Phe Gly Ser Leu Ala Phe Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85
```

<210> SEQ ID NO 20
<211> LENGTH: 85
<212> TYPE: PRT
<213> ORGANISM: Artificial sequence
<220> FEATURE:
<223> OTHER INFORMATION: Synthetic construct; trimeric coiled coil with
cancer CTL epitope

<400> SEQUENCE: 20

```
Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Arg Leu Glu Ile Ile Ser Ala Val Val Gly Ile Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85
```

<210> SEQ ID NO 21
<211> LENGTH: 85
<212> TYPE: PRT
<213> ORGANISM: Artificial sequence
<220> FEATURE:
<223> OTHER INFORMATION: Synthetic construct; trimeric coiled coil with
cancer CTL epitope

<400> SEQUENCE: 21

```
Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Leu Leu His Glu Thr Asp Ser Ala Val Glu Glu Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85
```

```
<210> SEQ ID NO 22
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 22

Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Ala Leu Phe Asp Ile Glu Ser Lys Val Glu Glu Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 23
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 23

Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Arg Leu Ser Leu Phe Arg Ala Val Ile Thr Lys Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 24
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 24

Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Lys Met Val Glu Leu Val His Phe Leu Glu Glu Leu Glu Arg
```

50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 25
<211> LENGTH: 85
<212> TYPE: PRT
<213> ORGANISM: Artificial sequence
<220> FEATURE:
<223> OTHER INFORMATION: Synthetic construct; trimeric coiled coil with cancer CTL epitope

<400> SEQUENCE: 25

Trp Gln Thr Trp Asn Ala Lys Trp Asp Gln Trp Ser Asn Asp Trp Asn
1 5 10 15

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

Glu Arg Arg Tyr Leu Gln Leu Val Phe Gly Ile Glu Val Leu Glu Arg
50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 26
<211> LENGTH: 85
<212> TYPE: PRT
<213> ORGANISM: Artificial sequence
<220> FEATURE:
<223> OTHER INFORMATION: Synthetic construct; trimeric coiled coil with cancer CTL epitope

<400> SEQUENCE: 26

Trp Gln Thr Trp Asn Ala Lys Trp Asp Gln Trp Ser Asn Asp Trp Asn
1 5 10 15

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

Glu Arg Ala Ala Arg Ala Val Phe Leu Ala Leu Glu Glu Leu Glu Arg
50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 27
<211> LENGTH: 85
<212> TYPE: PRT
<213> ORGANISM: Artificial sequence
<220> FEATURE:
<223> OTHER INFORMATION: Synthetic construct; trimeric coiled coil with cancer CTL epitope

<400> SEQUENCE: 27

Trp Gln Thr Trp Asn Ala Lys Trp Asp Gln Trp Ser Asn Asp Trp Asn
1 5 10 15

```
Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Arg Leu Glu Glu Gln Asp Leu Thr Met Lys Tyr Gln Ile Phe
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 28
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 28

Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Glu Ala Tyr Gly Leu Asp Phe Tyr Ile Leu Glu Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 29
<211> LENGTH: 85
<212> TYPE: PRT
<213> ORGANISM: Artificial sequence
<220> FEATURE:
<223> OTHER INFORMATION: Synthetic construct; trimeric coiled coil with
      cancer CTL epitope

<400> SEQUENCE: 29

Trp Gln Thr Trp Asn Ala Lys Trp Asp Gln Trp Ser Asn Asp Trp Asn
1               5                   10                  15

Ala Trp Arg Ser Asp Trp Gln Ala Trp Lys Asp Asp Trp Ala Arg Trp
            20                  25                  30

Arg Ala Leu Trp Met Gly Gly Arg Leu Leu Ala Arg Leu Glu Glu Leu
        35                  40                  45

Glu Arg Arg Leu Ser Tyr Leu Asp Ser Gly Ile His Phe Leu Glu Arg
    50                  55                  60

Ala Ile Asn Thr Val Asp Leu Glu Leu Ala Ala Leu Arg Arg Arg Leu
65                  70                  75                  80

Glu Glu Leu Ala Arg
                85


<210> SEQ ID NO 30
<211> LENGTH: 85
<212> TYPE: PRT
<213> ORGANISM: Artificial sequence
<220> FEATURE:
<223> OTHER INFORMATION: Synthetic construct; trimeric coiled coil with
```

cancer CTL epitope

<400> SEQUENCE: 30

Trp Gln Thr Trp Asn Ala Lys Trp Asp Gln Trp Ser Asn Asp Trp Asn
1 5 10 15

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

Glu Arg Arg Leu Glu Glu Thr Val Ser Glu Gln Ser Asn Val Glu Arg
50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 31
<211> LENGTH: 85
<212> TYPE: PRT
<213> ORGANISM: Artificial sequence
<220> FEATURE:
<223> OTHER INFORMATION: Synthetic construct; trimeric coiled coil with cancer CTL epitope

<400> SEQUENCE: 31

Trp Gln Thr Trp Asn Ala Lys Trp Asp Gln Trp Ser Asn Asp Trp Asn
1 5 10 15

Ala Trp Arg Ser Asp Trp Gln Ala Trp Lys Asp Asp Trp Ala Arg Trp
20 25 30

Arg Ala Leu Trp Met Gly Gly Arg Leu Leu Ala Arg Leu Glu Glu Leu
35 40 45

Glu Glu Lys Leu Ile Val Val Leu Phe Arg Leu Glu Glu Leu Glu Arg
50 55 60

Ala Ile Asn Thr Val Asp Leu Glu Leu Ala Ala Leu Arg Arg Arg Leu
65 70 75 80

Glu Glu Leu Ala Arg
85

<210> SEQ ID NO 32
<211> LENGTH: 58
<212> TYPE: PRT
<213> ORGANISM: Artificial sequence
<220> FEATURE:
<223> OTHER INFORMATION: Synthetic construct; coiled coil with HIV-V3 B-cell epitope

<400> SEQUENCE: 32

Arg Leu Leu Ala Arg Leu Glu Glu Leu Glu Arg Arg Leu Glu Glu Leu
1 5 10 15

Glu Arg Arg Leu Glu Glu Leu Glu Arg Arg Leu Gly Ser Ile Arg Ile
20 25 30

Gly Pro Gly Gln Thr Phe Tyr Ala Gly Val Asp Leu Glu Leu Ala Ala
35 40 45

Leu Arg Arg Arg Leu Glu Glu Leu Ala Arg
50 55

<210> SEQ ID NO 33
<211> LENGTH: 106
<212> TYPE: PRT
<213> ORGANISM: Artificial sequence
<220> FEATURE:

<223> OTHER INFORMATION: Synthetic construct; building block comprising His-tag, COMP and P5c6

<400> SEQUENCE: 33

Met Gly His His His His His His Gly Asp Trp Lys Trp Asp Gly Gly
1 5 10 15

Leu Val Pro Arg Gly Ser Asp Glu Met Leu Arg Glu Leu Gln Glu Thr
20 25 30

Asn Ala Ala Leu Gln Asp Val Arg Glu Leu Leu Arg Gln Gln Val Lys
35 40 45

Gln Ile Thr Phe Leu Arg Ala Leu Leu Met Gly Gly Arg Leu Leu Ala
50 55 60

Arg Leu Glu Glu Leu Glu Arg Arg Leu Glu Glu Leu Glu Arg Arg Leu
65 70 75 80

Glu Glu Leu Glu Arg Ala Ile Asn Thr Val Asp Leu Glu Leu Ala Ala
85 90 95

Leu Arg Arg Arg Leu Glu Glu Leu Ala Arg
100 105

<210> SEQ ID NO 34
<211> LENGTH: 49
<212> TYPE: PRT
<213> ORGANISM: Artificial sequence
<220> FEATURE:
<223> OTHER INFORMATION: Synthetic construct; trimeric coiled coil with HBV epitopes

<400> SEQUENCE: 34

Arg Leu Leu Ala Arg Leu Glu Glu Leu Glu Arg Arg Leu Glu Glu Leu
1 5 10 15

Gln Ser Leu Thr Asn Leu Leu Ser Ser Asn Leu Ser Trp Leu Ser Leu
20 25 30

Asp Val Ser Ala Ala Phe Arg Arg Leu Glu Glu Leu Glu Ala Arg Val
35 40 45

Met

<210> SEQ ID NO 35
<211> LENGTH: 46
<212> TYPE: PRT
<213> ORGANISM: Artificial sequence
<220> FEATURE:
<223> OTHER INFORMATION: Synthetic construct; trimeric coiled coil with PADRE and HBV epitope

<400> SEQUENCE: 35

Arg Leu Leu Ala Arg Leu Glu Glu Leu Glu Arg Arg Leu Glu Glu Leu
1 5 10 15

Ala Arg Phe Val Ala Ala Trp Thr Leu Lys Val Arg Glu Val Glu Arg
20 25 30

Glu Leu Ser Trp Leu Ser Leu Asp Val Ser Ala Ala Phe Arg
35 40 45

<210> SEQ ID NO 36
<211> LENGTH: 42
<212> TYPE: PRT
<213> ORGANISM: Artificial sequence
<220> FEATURE:
<223> OTHER INFORMATION: Synthetic construct; modified tetrameric coiled coil from tetrabrachion

<400> SEQUENCE: 36

Leu Tyr Arg Leu Thr Val Ile Ile Asp Asp Arg Tyr Glu Ser Leu Lys

```
1               5                   10                  15

Asn Leu Ile Thr Leu Arg Ala Asp Arg Leu Glu Met Ile Ile Asn Asp
            20                  25                  30

Asn Val Ser Thr Leu Arg Ala Leu Leu Met
        35                  40


<210> SEQ ID NO 37
<211> LENGTH: 129
<212> TYPE: PRT
<213> ORGANISM: Artificial sequence
<220> FEATURE:
<223> OTHER INFORMATION: Synthetic construct; tetrameric coiled coil
      with M2e B-cell epitope from human influenza

<400> SEQUENCE: 37

Met Gly His His His His His His Ala Ser Leu Val Pro Arg Gly Ser
1               5                   10                  15

Leu Leu Thr Glu Val Glu Thr Pro Ile Arg Asn Glu Trp Gly Cys Arg
            20                  25                  30

Cys Asn Asp Ser Ser Gly Ser Leu Tyr Arg Leu Thr Val Ile Ile Asp
        35                  40                  45

Asp Arg Tyr Glu Ser Leu Lys Asn Leu Ile Thr Leu Arg Ala Asp Arg
    50                  55                  60

Leu Glu Met Ile Ile Asn Asp Asn Val Ser Thr Leu Arg Ala Leu Leu
65                  70                  75                  80

Met Gly Gly Arg Leu Leu Ala Arg Leu Glu Glu Leu Glu Arg Arg Leu
                85                  90                  95

Glu Glu Leu Glu Arg Arg Leu Glu Glu Leu Glu Arg Ala Ile Asn Thr
            100                 105                 110

Val Asp Leu Glu Leu Ala Ala Leu Arg Arg Arg Leu Glu Glu Leu Ala
        115                 120                 125

Arg


<210> SEQ ID NO 38
<211> LENGTH: 129
<212> TYPE: PRT
<213> ORGANISM: Artificial sequence
<220> FEATURE:
<223> OTHER INFORMATION: Synthetic construct; tetrameric coiled coil
      with M2e B-cell epitope from chicken influenza

<400> SEQUENCE: 38

Met Gly His His His His His His Ala Ser Leu Val Pro Arg Gly Ser
1               5                   10                  15

Leu Leu Thr Glu Val Glu Thr Pro Thr Arg Asn Gly Trp Glu Cys Lys
            20                  25                  30

Cys Ser Asp Ser Ser Gly Ser Leu Tyr Arg Leu Thr Val Ile Ile Asp
        35                  40                  45

Asp Arg Tyr Glu Ser Leu Lys Asn Leu Ile Thr Leu Arg Ala Asp Arg
    50                  55                  60

Leu Glu Met Ile Ile Asn Asp Asn Val Ser Thr Leu Arg Ala Leu Leu
65                  70                  75                  80

Met Gly Gly Arg Leu Leu Ala Arg Leu Glu Glu Leu Glu Arg Arg Leu
                85                  90                  95

Glu Glu Leu Glu Arg Arg Leu Glu Glu Leu Glu Arg Ala Ile Asn Thr
            100                 105                 110

Val Asp Leu Glu Leu Ala Ala Leu Arg Arg Arg Leu Glu Glu Leu Ala
        115                 120                 125
```

Arg

<210> SEQ ID NO 39
<211> LENGTH: 33
<212> TYPE: PRT
<213> ORGANISM: Artificial sequence
<220> FEATURE:
<223> OTHER INFORMATION: Synthetic construct; pentameric coiled coil with HTL epitopes

<400> SEQUENCE: 39

```
Glu Arg Phe Val Ala Ala Trp Thr Leu Lys Val Ala Glu Trp Glu Glu
1               5                   10                  15

Lys Trp Lys Ile Trp Lys Ser Leu Trp Lys Ala Trp Arg Leu Leu Trp
            20                  25                  30

Met
```

<210> SEQ ID NO 40
<211> LENGTH: 46
<212> TYPE: PRT
<213> ORGANISM: Artificial sequence
<220> FEATURE:
<223> OTHER INFORMATION: Synthetic construct; trimeric coiled coil with P. falciparum HTL epitope

<400> SEQUENCE: 40

```
Arg Leu Leu Leu Arg Leu Glu Glu Leu Glu Arg Arg Leu Glu Glu Leu
1               5                   10                  15

Glu Lys Lys Ile Ala Lys Met Glu Lys Ala Ser Ser Val Phe Asn Val
            20                  25                  30

Val Leu Ala Ala Leu Arg Arg Arg Leu Glu Glu Leu Ala Arg
        35                  40                  45
```

<210> SEQ ID NO 41
<211> LENGTH: 128
<212> TYPE: PRT
<213> ORGANISM: Artificial sequence
<220> FEATURE:
<223> OTHER INFORMATION: Synthetic construct; pentameric coiled coil with tryptophane zipper and trimeric coiled coil with P. falciparum HTL epitope

<400> SEQUENCE: 41

```
Met Gly His His His His His His Ala Ser Trp Lys Trp Asp Gly Gly
1               5                   10                  15

Leu Val Pro Arg Gly Ser Trp Gln Thr Trp Asn Ala Lys Trp Asp Gln
            20                  25                  30

Trp Ser Asn Asp Trp Asn Ala Trp Arg Ser Asp Trp Gln Ala Trp Lys
        35                  40                  45

Asp Asp Trp Ala Phe Trp Arg Ala Leu Trp Met Gly Gly Arg Leu Leu
    50                  55                  60

Leu Arg Leu Glu Glu Leu Glu Arg Arg Leu Glu Glu Leu Glu Lys Lys
65                  70                  75                  80

Ile Ala Lys Met Glu Lys Ala Ser Ser Val Phe Asn Val Val Leu Ala
                85                  90                  95

Ala Leu Arg Arg Arg Leu Glu Glu Leu Ala Arg Gly Gly Ser Gly Ala
            100                 105                 110

Asn Ala Asn Pro Asn Ala Asn Pro Asn Ala Asn Pro Asn Ala Asn Pro
        115                 120                 125
```

<210> SEQ ID NO 42
<211> LENGTH: 128

<212> TYPE: PRT
<213> ORGANISM: Artificial sequence
<220> FEATURE:
<223> OTHER INFORMATION: Synthetic construct; HIV vaccine with
P. falciparum HTL epitope, PADRE HTL epitope and GP41 B-cell
epitope

<400> SEQUENCE: 42

```
Glu Leu Asp Lys Trp Ala Ser Leu Trp Asn Trp Phe Asn Ile Thr Asn
1               5                   10                  15

Trp Leu Trp Tyr Ile Arg Ser Trp Gln Thr Trp Asn Ala Lys Trp Asp
            20                  25                  30

Gln Trp Ala Lys Phe Ile Ala Ala Trp Thr Leu Lys Val Ala Ala Trp
        35                  40                  45

Lys Asp Asp Trp Ala Arg Trp Arg Ala Leu Trp Met Gly Gly Arg Leu
    50                  55                  60

Leu Leu Arg Leu Glu Glu Leu Glu Arg Arg Leu Glu Glu Leu Glu Lys
65                  70                  75                  80

Lys Ile Ala Lys Met Glu Lys Ala Ser Ser Val Phe Asn Val Val Leu
                85                  90                  95

Ala Ala Leu Arg Arg Arg Leu Glu Glu Leu Ala Arg Pro Leu Asp Glu
            100                 105                 110

Gly Phe Arg Lys Tyr Thr Ala Phe Thr Ile Pro Ser Ile Asn Asn Glu
        115                 120                 125
```

<210> SEQ ID NO 43
<211> LENGTH: 135
<212> TYPE: PRT
<213> ORGANISM: Artificial sequence
<220> FEATURE:
<223> OTHER INFORMATION: Synthetic construct; HIV vaccine with
P. falciparum HTL epitope, PADRE HTL epitope and GP41 B-cell
epitope

<400> SEQUENCE: 43

```
Glu Leu Asp Lys Trp Ala Ser Leu Trp Asn Trp Phe Asn Ile Thr Asn
1               5                   10                  15

Trp Leu Trp Tyr Ile Arg Ser Trp Gln Thr Trp Asn Ala Lys Trp Asp
            20                  25                  30

Gln Trp Ala Lys Phe Ile Ala Ala Trp Thr Leu Lys Val Ala Ala Trp
        35                  40                  45

Lys Asp Asp Trp Ala Arg Trp Arg Ala Leu Trp Met Gly Gly Arg Leu
    50                  55                  60

Leu Leu Arg Leu Glu Glu Leu Glu Arg Arg Leu Glu Glu Leu Glu Lys
65                  70                  75                  80

Lys Ile Ala Lys Met Glu Lys Ala Ser Ser Val Phe Asn Val Val Leu
                85                  90                  95

Ala Ala Leu Arg Arg Arg Leu Glu Glu Leu Ala Arg Lys Gly Pro Ala
            100                 105                 110

Lys Leu Leu Trp Lys Gly Glu Gly Ala Val Phe Ile His Asn Phe Lys
        115                 120                 125

Arg Lys Gly Gly Ile Gly Gly
    130                 135
```

<210> SEQ ID NO 44
<211> LENGTH: 134
<212> TYPE: PRT
<213> ORGANISM: Artificial sequence
<220> FEATURE:
<223> OTHER INFORMATION: Synthetic construct; HIV vaccine with
P. falciparum HTL epitope, PADRE HTL epitope and GP41 B-cell epitope

<400> SEQUENCE: 44

```
Glu Leu Asp Lys Trp Ala Ser Leu Trp Asn Trp Phe Asn Ile Thr Asn
1               5                   10                  15

Trp Leu Trp Tyr Ile Arg Ser Trp Gln Thr Trp Asn Ala Lys Trp Asp
            20                  25                  30

Gln Trp Ala Lys Phe Ile Ala Ala Trp Thr Leu Lys Val Ala Ala Trp
        35                  40                  45

Lys Asp Asp Trp Ala Arg Trp Arg Ala Leu Trp Met Gly Gly Arg Leu
    50                  55                  60

Leu Leu Arg Leu Glu Glu Leu Glu Arg Arg Leu Glu Glu Leu Glu Lys
65                  70                  75                  80

Lys Ile Ala Lys Met Glu Lys Ala Ser Ser Val Phe Asn Val Val Leu
                85                  90                  95

Ala Ala Leu Arg Arg Arg Leu Glu Glu Leu Ala Arg Ile Ile Gly Arg
            100                 105                 110

Asn Leu Leu Thr Gln Ile Gly Cys Thr Leu Asn Phe Pro Ile Ser Pro
        115                 120                 125

Ile Glu Thr Val Pro Val
    130
```

<210> SEQ ID NO 45
<211> LENGTH: 129
<212> TYPE: PRT
<213> ORGANISM: Artificial sequence
<220> FEATURE:
<223> OTHER INFORMATION: Synthetic construct; HIV vaccine with P. falciparum HTL epitope, PADRE HTL epitope and GP41 B-cell epitope

<400> SEQUENCE: 45

```
Glu Leu Asp Lys Trp Ala Ser Leu Trp Asn Trp Phe Asn Ile Thr Asn
1               5                   10                  15

Trp Leu Trp Tyr Ile Arg Ser Trp Gln Thr Trp Asn Ala Lys Trp Asp
            20                  25                  30

Gln Trp Ala Lys Phe Ile Ala Ala Trp Thr Leu Lys Val Ala Ala Trp
        35                  40                  45

Lys Asp Asp Trp Ala Arg Trp Arg Ala Leu Trp Met Gly Gly Arg Leu
    50                  55                  60

Leu Leu Arg Leu Glu Glu Leu Glu Arg Arg Leu Glu Glu Leu Glu Lys
65                  70                  75                  80

Lys Ile Ala Lys Met Glu Lys Ala Ser Ser Val Phe Asn Val Val Leu
                85                  90                  95

Ala Ala Leu Arg Arg Arg Leu Glu Glu Leu Ala Arg Asp Phe Trp Glu
            100                 105                 110

Val Gln Leu Gly Ile Pro His Pro Ala Gly Leu Lys Lys Lys Lys Ser
        115                 120                 125

Val
```

<210> SEQ ID NO 46
<211> LENGTH: 131
<212> TYPE: PRT
<213> ORGANISM: Artificial sequence
<220> FEATURE:
<223> OTHER INFORMATION: Synthetic construct; HIV vaccine with P. falciparum HTL epitope, PADRE HTL epitope and GP41 B-cell epitope

<400> SEQUENCE: 46

```
Glu Leu Asp Lys Trp Ala Ser Leu Trp Asn Trp Phe Asn Ile Thr Asn
1               5                   10                  15

Trp Leu Trp Tyr Ile Arg Ser Trp Gln Thr Trp Asn Ala Lys Trp Asp
            20                  25                  30

Gln Trp Ala Lys Phe Ile Ala Ala Trp Thr Leu Lys Val Ala Ala Trp
        35                  40                  45

Lys Asp Asp Trp Ala Arg Trp Arg Ala Leu Trp Met Gly Gly Arg Leu
    50                  55                  60

Leu Leu Arg Leu Glu Glu Leu Glu Arg Arg Leu Glu Glu Leu Glu Lys
65                  70                  75                  80

Lys Ile Ala Lys Met Glu Lys Ala Ser Ser Val Phe Asn Val Val Leu
                85                  90                  95

Ala Ala Leu Arg Arg Arg Leu Glu Glu Leu Ala Arg Leu Thr Glu Glu
            100                 105                 110

Ala Glu Leu Glu Leu Ala Glu Asn Arg Glu Ile Leu Lys Asp Pro Val
        115                 120                 125

His Gly Val
    130


<210> SEQ ID NO 47
<211> LENGTH: 125
<212> TYPE: PRT
<213> ORGANISM: Artificial sequence
<220> FEATURE:
<223> OTHER INFORMATION: Synthetic construct; HIV vaccine with
      P. falciparum HTL epitope, PADRE HTL epitope and GP41 B-cell
      epitope

<400> SEQUENCE: 47

Glu Leu Asp Lys Trp Ala Ser Leu Trp Asn Trp Phe Asn Ile Thr Asn
1               5                   10                  15

Trp Leu Trp Tyr Ile Arg Ser Trp Gln Thr Trp Asn Ala Lys Trp Asp
            20                  25                  30

Gln Trp Ala Lys Phe Ile Ala Ala Trp Thr Leu Lys Val Ala Ala Trp
        35                  40                  45

Lys Asp Asp Trp Ala Arg Trp Arg Ala Leu Trp Met Gly Gly Arg Leu
    50                  55                  60

Leu Leu Arg Leu Glu Glu Leu Glu Arg Arg Leu Glu Glu Leu Glu Lys
65                  70                  75                  80

Lys Ile Ala Lys Met Glu Lys Ala Ser Ser Val Phe Asn Val Val Leu
                85                  90                  95

Ala Ala Leu Arg Arg Arg Leu Glu Glu Leu Ala Arg Leu Val Ser Gln
            100                 105                 110

Gly Ile Arg Lys Val Leu Phe Leu Asp Gly Ile Asp Lys
        115                 120                 125


<210> SEQ ID NO 48
<211> LENGTH: 133
<212> TYPE: PRT
<213> ORGANISM: Artificial sequence
<220> FEATURE:
<223> OTHER INFORMATION: Synthetic construct; malaria vaccine with
      P. falciparum CTL epitopes

<400> SEQUENCE: 48

Lys Pro Asn Asp Lys Ser Leu Tyr Lys Pro Lys Asp Glu Leu Asp Tyr
1               5                   10                  15

Glu Ala Lys Pro Ile Val Gln Tyr Asp Asn Phe Met Asn Gly Ser Glu
            20                  25                  30
```

```
Arg Phe Val Ala Ala Trp Thr Leu Lys Val Ala Glu Trp Glu Glu Lys
        35                  40                  45

Trp Lys Ile Trp Lys Ser Leu Trp Lys Ala Trp Arg Leu Leu Trp Met
    50                  55                  60

Gly Gly Arg Leu Leu Leu Arg Leu Glu Glu Leu Met Glu Lys Leu Lys
65                  70                  75                  80

Glu Leu Glu Lys Lys Leu Arg Asn Leu Glu Glu Glu Leu His Ser Leu
                85                  90                  95

Arg Lys Asn Leu Asn Ile Leu Asn Glu Glu Leu Glu Glu Leu Thr Arg
            100                 105                 110

Gly Gly Ser Gly Ala Asn Ala Asn Pro Asn Ala Asn Pro Asn Ala Asn
        115                 120                 125

Pro Asn Ala Asn Pro
    130


<210> SEQ ID NO 49
<211> LENGTH: 137
<212> TYPE: PRT
<213> ORGANISM: Artificial sequence
<220> FEATURE:
<223> OTHER INFORMATION: Synthetic construct; malaria vaccine with
      P. falciparum CTL epitopes

<400> SEQUENCE: 49

Ala Ser Lys Asn Lys Glu Lys Ala Leu Ile Ile Ala Ala Gly Ile Ala
1               5                   10                  15

Gly Gly Leu Ala Leu Leu Arg Ser Leu Leu Met Asp Cys Ser Gly Ser
            20                  25                  30

Ile Gly Ser Glu Arg Phe Val Ala Ala Trp Thr Leu Lys Val Ala Glu
        35                  40                  45

Trp Glu Glu Lys Trp Lys Ile Trp Lys Ser Leu Trp Lys Ala Trp Arg
    50                  55                  60

Leu Leu Trp Met Gly Gly Arg Leu Leu Leu Arg Leu Glu Glu Leu Met
65                  70                  75                  80

Glu Lys Leu Lys Glu Leu Glu Lys Lys Leu Arg Asn Leu Glu Glu Glu
                85                  90                  95

Leu His Ser Leu Arg Lys Asn Leu Asn Ile Leu Asn Glu Glu Leu Glu
            100                 105                 110

Glu Leu Thr Arg Gly Gly Ser Gly Ala Asn Ala Asn Pro Asn Ala Asn
        115                 120                 125

Pro Asn Ala Asn Pro Asn Ala Asn Pro
    130                 135


<210> SEQ ID NO 50
<211> LENGTH: 135
<212> TYPE: PRT
<213> ORGANISM: Artificial sequence
<220> FEATURE:
<223> OTHER INFORMATION: Synthetic construct; malaria vaccine with
      P. falciparum CTL epitopes

<400> SEQUENCE: 50

Met Asn Pro Asn Asp Pro Asn Arg Asn Val Gln Gln Met Pro Asn Asp
1               5                   10                  15

Pro Asn Arg Asn Val Gln Gln Lys Ser Leu Tyr Asp Glu His Ile Gly
            20                  25                  30

Ser Glu Arg Phe Val Ala Ala Trp Thr Leu Lys Val Ala Glu Trp Glu
        35                  40                  45
```

```
Glu Lys Trp Lys Ile Trp Lys Ser Leu Trp Lys Ala Trp Arg Leu Leu
    50                  55                  60

Trp Met Gly Gly Arg Leu Leu Leu Arg Leu Glu Glu Leu Met Glu Lys
65                  70                  75                  80

Leu Lys Glu Leu Glu Lys Lys Leu Arg Asn Leu Glu Glu Glu Leu His
                85                  90                  95

Ser Leu Arg Lys Asn Leu Asn Ile Leu Asn Glu Glu Leu Glu Glu Leu
            100                 105                 110

Thr Arg Gly Gly Ser Gly Ala Asn Ala Asn Pro Asn Ala Asn Pro Asn
        115                 120                 125

Ala Asn Pro Asn Ala Asn Pro
    130                 135


<210> SEQ ID NO 51
<211> LENGTH: 134
<212> TYPE: PRT
<213> ORGANISM: Artificial sequence
<220> FEATURE:
<223> OTHER INFORMATION: Synthetic construct; malaria vaccine with
      P. falciparum CTL epitopes

<400> SEQUENCE: 51

Met Ile Asn Ala Tyr Leu Asp Lys Leu Arg Ala Ile Ser Lys Tyr Glu
1               5                   10                  15

Asp Glu Ile Phe Ala His Leu Gly Asn Val Lys Tyr Leu Val Gly Ser
            20                  25                  30

Glu Arg Phe Val Ala Ala Trp Thr Leu Lys Val Ala Glu Trp Glu Glu
        35                  40                  45

Lys Trp Lys Ile Trp Lys Ser Leu Trp Lys Ala Trp Arg Leu Leu Trp
    50                  55                  60

Met Gly Gly Arg Leu Leu Leu Arg Leu Glu Glu Leu Met Glu Lys Leu
65                  70                  75                  80

Lys Glu Leu Glu Lys Lys Leu Arg Asn Leu Glu Glu Glu Leu His Ser
                85                  90                  95

Leu Arg Lys Asn Leu Asn Ile Leu Asn Glu Glu Leu Glu Glu Leu Thr
            100                 105                 110

Arg Gly Gly Ser Gly Ala Asn Ala Asn Pro Asn Ala Asn Pro Asn Ala
        115                 120                 125

Asn Pro Asn Ala Asn Pro
    130


<210> SEQ ID NO 52
<211> LENGTH: 136
<212> TYPE: PRT
<213> ORGANISM: Artificial sequence
<220> FEATURE:
<223> OTHER INFORMATION: Synthetic construct; malaria vaccine with
      P. falciparum CTL epitopes

<400> SEQUENCE: 52

Glu Asn Asp Ile Glu Lys Lys Ile Ala Lys Met Glu Lys Ala Ser Lys
1               5                   10                  15

Ser Leu Tyr Asp Glu His Ile Leu Leu Met Asp Cys Ser Gly Ser Ile
            20                  25                  30

Gly Ser Glu Arg Phe Val Ala Ala Trp Thr Leu Lys Val Ala Glu Trp
        35                  40                  45

Glu Glu Lys Trp Lys Ile Trp Lys Ser Leu Trp Lys Ala Trp Arg Leu
    50                  55                  60

Leu Trp Met Gly Gly Arg Leu Leu Leu Arg Leu Glu Glu Leu Met Glu
```

```
65                  70                  75                  80

Lys Leu Lys Glu Leu Glu Lys Lys Leu Arg Asn Leu Glu Glu Glu Leu
                85                  90                  95

His Ser Leu Arg Lys Asn Leu Asn Ile Leu Asn Glu Glu Leu Glu Glu
            100                 105                 110

Leu Thr Arg Gly Gly Ser Gly Ala Asn Ala Asn Pro Asn Ala Asn Pro
        115                 120                 125

Asn Ala Asn Pro Asn Ala Asn Pro
    130                 135
```

<210> SEQ ID NO 53
<211> LENGTH: 132
<212> TYPE: PRT
<213> ORGANISM: Artificial sequence
<220> FEATURE:
<223> OTHER INFORMATION: Synthetic construct; malaria vaccine with P. falciparum CTL epitopes

<400> SEQUENCE: 53

```
Lys Ser Lys Asp Glu Leu Asp Tyr Glu Ala Ile Pro Ser Leu Ala Leu
1               5                   10                  15

Met Leu Ile Met Pro Leu Glu Thr Gln Leu Ala Ile Gly Ser Glu Arg
            20                  25                  30

Phe Val Ala Ala Trp Thr Leu Lys Val Ala Glu Trp Glu Glu Lys Trp
        35                  40                  45

Lys Ile Trp Lys Ser Leu Trp Lys Ala Trp Arg Leu Leu Trp Met Gly
    50                  55                  60

Gly Arg Leu Leu Leu Arg Leu Glu Glu Leu Met Glu Lys Leu Lys Glu
65                  70                  75                  80

Leu Glu Lys Lys Leu Arg Asn Leu Glu Glu Glu Leu His Ser Leu Arg
                85                  90                  95

Lys Asn Leu Asn Ile Leu Asn Glu Glu Leu Glu Glu Leu Thr Arg Gly
            100                 105                 110

Gly Ser Gly Ala Asn Ala Asn Pro Asn Ala Asn Pro Asn Ala Asn Pro
        115                 120                 125

Asn Ala Asn Pro
    130
```

<210> SEQ ID NO 54
<211> LENGTH: 152
<212> TYPE: PRT
<213> ORGANISM: Artificial sequence
<220> FEATURE:
<223> OTHER INFORMATION: Synthetic construct; influenza vaccine with B-cell epitope M2e and influenza CTL epitopes

<400> SEQUENCE: 54

```
Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Gln Ser Leu Thr Asn Leu Leu Ser Ser Asn Leu Ser
                85                  90                  95
```

```
Trp Leu Ser Leu Asp Val Ser Ala Ala Phe Arg Arg Leu Glu Glu Leu
            100                 105                 110

Glu Ala Arg Val Ile Arg His Glu Asn Arg Met Val Leu Gln Ala Tyr
        115                 120                 125

Gln Lys Arg Met Gly Val Leu Lys Met Pro Ala Ser Arg Tyr Leu Ser
    130                 135                 140

Arg Tyr Leu Thr Asp Met Thr Leu
145                 150


<210> SEQ ID NO 55
<211> LENGTH: 143
<212> TYPE: PRT
<213> ORGANISM: Artificial sequence
<220> FEATURE:
<223> OTHER INFORMATION: Synthetic construct; influenza vaccine with
      B-cell epitope M2e and influenza CTL epitopes

<400> SEQUENCE: 55

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Gln Ser Leu Thr Asn Leu Leu Ser Ser Asn Leu Ser
                85                  90                  95

Trp Leu Ser Leu Asp Val Ser Ala Ala Phe Arg Arg Leu Glu Glu Leu
            100                 105                 110

Glu Ala Arg Val Phe Met Leu Met Pro Lys Gln Lys Val Met Arg Met
        115                 120                 125

Gly Asp Phe His Ser Leu Tyr Leu Leu Ala Trp Lys Gln Val Leu
    130                 135                 140


<210> SEQ ID NO 56
<211> LENGTH: 143
<212> TYPE: PRT
<213> ORGANISM: Artificial sequence
<220> FEATURE:
<223> OTHER INFORMATION: Synthetic construct; influenza vaccine with
      B-cell epitope M2e and influenza CTL epitopes

<400> SEQUENCE: 56

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Gln Ser Leu Thr Asn Leu Leu Ser Ser Asn Leu Ser
                85                  90                  95
```

-continued

```
Trp Leu Ser Leu Asp Val Ser Ala Ala Phe Arg Arg Leu Glu Glu Leu
            100                 105                 110

Glu Ala Arg Val Ala Pro Ile Glu His Ile Ala Ser Met Arg Arg Asn
        115                 120                 125

Tyr Phe Thr Ala Glu Val Ile Gln Met Cys Thr Glu Leu Lys Leu
    130                 135                 140


<210> SEQ ID NO 57
<211> LENGTH: 143
<212> TYPE: PRT
<213> ORGANISM: Artificial sequence
<220> FEATURE:
<223> OTHER INFORMATION: Synthetic construct; influenza vaccine with
      B-cell epitope M2e and influenza CTL epitopes

<400> SEQUENCE: 57

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Gln Ser Leu Thr Asn Leu Leu Ser Ser Asn Leu Ser
                85                  90                  95

Trp Leu Ser Leu Asp Val Ser Ala Ala Phe Arg Arg Leu Glu Glu Leu
            100                 105                 110

Glu Ala Arg Val Ala Ala Gly Ala Ala Val Lys Gly Val Val Gly Thr
        115                 120                 125

Met Val Met Glu Leu Ile Asn Pro Thr Leu Leu Phe Leu Lys Val
    130                 135                 140


<210> SEQ ID NO 58
<211> LENGTH: 144
<212> TYPE: PRT
<213> ORGANISM: Artificial sequence
<220> FEATURE:
<223> OTHER INFORMATION: Synthetic construct; influenza vaccine with
      B-cell epitope M2e and influenza CTL epitopes

<400> SEQUENCE: 58

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Gln Ser Leu Thr Asn Leu Leu Ser Ser Asn Leu Ser
                85                  90                  95

Trp Leu Ser Leu Asp Val Ser Ala Ala Phe Arg Arg Leu Glu Glu Leu
            100                 105                 110

Glu Ala Arg Val Arg Leu Ile Asp Phe Leu Lys Asp Val Met Gln Ile
```

```
        115                 120                 125

Arg Gly Phe Val Tyr Phe Ile Met Phe Ser Asn Lys Met Ala Arg Leu
    130                 135                 140


<210> SEQ ID NO 59
<211> LENGTH: 152
<212> TYPE: PRT
<213> ORGANISM: Artificial sequence
<220> FEATURE:
<223> OTHER INFORMATION: Synthetic construct; influenza vaccine with
      B-cell epitope M2e and influenza CTL epitopes

<400> SEQUENCE: 59

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Gln Ser Leu Thr Asn Leu Leu Ser Ser Asn Leu Ser
                85                  90                  95

Trp Leu Ser Leu Asp Val Ser Ala Ala Phe Arg Arg Leu Glu Glu Leu
            100                 105                 110

Glu Ala Arg Val Glu Arg Asn Glu Gln Gly Gln Thr Leu Val Ala Tyr
        115                 120                 125

Met Leu Glu Arg Glu Leu Leu Arg His Phe Gln Lys Asp Ala Lys Val
    130                 135                 140

Arg Asp Gln Arg Gly Asn Val Leu
145                 150


<210> SEQ ID NO 60
<211> LENGTH: 142
<212> TYPE: PRT
<213> ORGANISM: Artificial sequence
<220> FEATURE:
<223> OTHER INFORMATION: Synthetic construct; influenza vaccine with
      B-cell epitope M2e and other influenza B-cell epitopes

<400> SEQUENCE: 60

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Ala Lys Phe Val Ala Ala Trp Thr Leu Lys Val Arg
                85                  90                  95

Glu Val Glu Arg Glu Leu Ser Trp Leu Ser Leu Asp Val Ser Ala Ala
            100                 105                 110

Phe Leu Glu Arg Lys Lys Arg Gly Leu Phe Gly Asp Ile Gln Ser Arg
        115                 120                 125
```

```
Gly Leu Phe Gly Asp Glu Arg Gln Thr Arg Gly Ile Phe Gly
    130                 135                 140


<210> SEQ ID NO 61
<211> LENGTH: 142
<212> TYPE: PRT
<213> ORGANISM: Artificial sequence
<220> FEATURE:
<223> OTHER INFORMATION: Synthetic construct; influenza vaccine with
      B-cell epitope M2e and other influenza B-cell epitopes

<400> SEQUENCE: 61

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Ala Lys Phe Val Ala Ala Trp Thr Leu Lys Val Arg
                85                  90                  95

Glu Val Glu Arg Glu Leu Ser Trp Leu Ser Leu Asp Val Ser Ala Ala
            100                 105                 110

Phe Leu Glu Arg Lys Thr Arg Gly Leu Phe Gly Asp Pro Lys Gly Arg
        115                 120                 125

Gly Leu Phe Gly Asp Gln Ile Glu Ser Arg Gly Leu Phe Gly
    130                 135                 140


<210> SEQ ID NO 62
<211> LENGTH: 142
<212> TYPE: PRT
<213> ORGANISM: Artificial sequence
<220> FEATURE:
<223> OTHER INFORMATION: Synthetic construct; influenza vaccine with
      B-cell epitope M2e and other influenza B-cell epitopes

<400> SEQUENCE: 62

Ser Leu Leu Thr Glu Val Glu Thr Pro Ile Arg Asn Glu Trp Gly Cys
1               5                   10                  15

Arg Cys Asn Asp Ser Ser Gly Ser Leu Tyr Arg Leu Thr Val Ile Ile
            20                  25                  30

Asp Asp Arg Tyr Glu Ser Leu Lys Asn Leu Ile Thr Leu Arg Ala Asp
        35                  40                  45

Arg Leu Glu Met Ile Ile Asn Asp Asn Val Ser Thr Leu Arg Ala Leu
    50                  55                  60

Leu Met Gly Gly Arg Leu Leu Ala Arg Leu Glu Glu Leu Glu Arg Arg
65                  70                  75                  80

Leu Glu Glu Leu Ala Lys Phe Val Ala Ala Trp Thr Leu Lys Val Arg
                85                  90                  95

Glu Val Glu Arg Glu Leu Ser Trp Leu Ser Leu Asp Val Ser Ala Ala
            100                 105                 110

Phe Leu Glu Lys Lys Gly Arg Gly Leu Phe Gly Asp Ala Ser Tyr Arg
        115                 120                 125

Gly Leu Phe Gly Asp Lys Arg Glu Lys Arg Gly Leu Phe Gly
    130                 135                 140
```

<210> SEQ ID NO 63
<211> LENGTH: 11
<212> TYPE: PRT
<213> ORGANISM: Artificial sequence
<220> FEATURE:
<223> OTHER INFORMATION: Synthetic construct; artificial antimicrobial
      peptide

<400> SEQUENCE: 63

Lys Leu Lys Leu Leu Leu Leu Leu Lys Leu Lys
1               5                   10

<210> SEQ ID NO 64
<211> LENGTH: 49
<212> TYPE: PRT
<213> ORGANISM: Artificial sequence
<220> FEATURE:
<223> OTHER INFORMATION: Synthetic construct; tetrameric coiled coil
      of tetrabrachion

<400> SEQUENCE: 64

Ile Ile Asn Glu Thr Ala Asp Asp Ile Val Tyr Arg Leu Thr Val Ile
1               5                   10                  15

Ile Asp Asp Arg Tyr Glu Ser Leu Lys Asn Leu Ile Thr Leu Arg Ala
            20                  25                  30

Asp Arg Leu Met Ile Ile Asn Asp Asn Val Ser Thr Ile Leu Ala Ser
        35                  40                  45

Gly

<210> SEQ ID NO 65
<211> LENGTH: 9
<212> TYPE: PRT
<213> ORGANISM: Plasmodium vivax

<400> SEQUENCE: 65

Gly Asp Arg Ala Ala Gly Gln Pro Ala
1               5

<210> SEQ ID NO 66
<211> LENGTH: 9
<212> TYPE: PRT
<213> ORGANISM: Plasmodium vivax

<400> SEQUENCE: 66

Gly Asp Arg Ala Asp Gly Gln Pro Ala
1               5

<210> SEQ ID NO 67
<211> LENGTH: 9
<212> TYPE: PRT
<213> ORGANISM: Plasmodium vivax

<400> SEQUENCE: 67

Gly Asp Arg Ala Asp Gly Gln Ala Ala
1               5

<210> SEQ ID NO 68
<211> LENGTH: 9
<212> TYPE: PRT
<213> ORGANISM: Plasmodium vivax

<400> SEQUENCE: 68

Gly Asn Gly Ala Gly Gly Gln Pro Ala
1               5

<210> SEQ ID NO 69
<211> LENGTH: 9
<212> TYPE: PRT
<213> ORGANISM: Plasmodium vivax

<400> SEQUENCE: 69

Gly Asp Gly Ala Ala Gly Gln Pro Ala
1               5

<210> SEQ ID NO 70
<211> LENGTH: 9
<212> TYPE: PRT
<213> ORGANISM: Plasmodium vivax

<400> SEQUENCE: 70

Gly Asp Arg Ala Ala Gly Gln Ala Ala
1               5

<210> SEQ ID NO 71
<211> LENGTH: 9
<212> TYPE: PRT
<213> ORGANISM: Plasmodium vivax

<400> SEQUENCE: 71

Gly Asn Gly Ala Gly Gly Gln Ala Ala
1               5

<210> SEQ ID NO 72
<211> LENGTH: 46
<212> TYPE: PRT
<213> ORGANISM: Plasmodium falciparum

<400> SEQUENCE: 72

Ile Lys Thr Met Asn Thr Gln Ile Ser Thr Leu Lys Asn Asp Val His
1               5                   10                  15

Leu Leu Asn Glu Gln Ile Asp Lys Leu Asn Asn Glu Lys Gly Thr Leu
            20                  25                  30

Asn Ser Lys Ile Ser Glu Leu Asn Val Gln Ile Met Asp Leu
        35                  40                  45

<210> SEQ ID NO 73
<211> LENGTH: 25
<212> TYPE: PRT
<213> ORGANISM: Plasmodium falciparum

<400> SEQUENCE: 73

Leu Leu Ser Lys Asp Lys Glu Ile Glu Glu Lys Asn Lys Lys Ile Lys
1               5                   10                  15

Glu Leu Asn Asn Asp Ile Lys Lys Leu
            20                  25

<210> SEQ ID NO 74
<211> LENGTH: 49
<212> TYPE: PRT
<213> ORGANISM: Plasmodium falciparum

<400> SEQUENCE: 74

Ile Cys Ser Leu Thr Thr Glu Val Met Glu Leu Asn Asn Lys Lys Asn
1               5                   10                  15

Glu Leu Ile Glu Glu Asn Asn Lys Leu Asn Leu Val Asp Gln Gly Lys
            20                  25                  30

Lys Lys Leu Lys Lys Asp Val Glu Lys Gln Lys Lys Glu Ile Glu Lys
        35                  40                  45

Leu

<210> SEQ ID NO 75
<211> LENGTH: 77
<212> TYPE: PRT
<213> ORGANISM: Plasmodium falciparum

<400> SEQUENCE: 75

```
Val Asp Lys Ile Glu Glu His Ile Leu Asp Tyr Asp Glu Glu Ile Asn
1               5                   10                  15

Lys Ser Arg Ser Asn Leu Phe Gln Leu Lys Asn Glu Ile Cys Ser Leu
            20                  25                  30

Thr Thr Glu Val Met Glu Leu Asn Asn Lys Lys Asn Glu Leu Ile Glu
        35                  40                  45

Glu Asn Asn Lys Leu Asn Leu Val Asp Gln Gly Lys Lys Lys Leu Lys
    50                  55                  60

Lys Asp Val Glu Lys Gln Lys Lys Glu Ile Glu Lys Leu
65                  70                  75
```

<210> SEQ ID NO 76
<211> LENGTH: 25
<212> TYPE: PRT
<213> ORGANISM: Plasmodium falciparum

<400> SEQUENCE: 76

```
Leu Asp Glu Asn Glu Asp Asn Ile Lys Lys Met Lys Ser Lys Ile Asp
1               5                   10                  15

Asp Met Glu Lys Glu Ile Lys Tyr Arg
            20                  25
```

<210> SEQ ID NO 77
<211> LENGTH: 41
<212> TYPE: PRT
<213> ORGANISM: Plasmodium falciparum

<400> SEQUENCE: 77

```
Gly Met Asn Asn Met Asn Gly Asp Ile Asn Asn Ile Asn Gly Asp Ile
1               5                   10                  15

Asn Asn Met Asn Gly Asp Ile Asn Asn Met Asn Gly Asp Ile Asn Asn
            20                  25                  30

Met Asn Gly Asp Ile Asn Asn Met Asn
        35                  40
```

<210> SEQ ID NO 78
<211> LENGTH: 27
<212> TYPE: PRT
<213> ORGANISM: Plasmodium falciparum

<400> SEQUENCE: 78

```
Lys Lys Arg Asn Val Glu Glu Glu Leu His Ser Leu Arg Lys Asn Tyr
1               5                   10                  15

Asn Ile Ile Asn Glu Glu Ile Glu Glu Ile Thr
            20                  25
```

<210> SEQ ID NO 79
<211> LENGTH: 37
<212> TYPE: PRT
<213> ORGANISM: Plasmodium falciparum

<400> SEQUENCE: 79

```
Glu Glu Ile Lys Glu Glu Ile Lys Glu Val Lys Glu Glu Ile Lys Glu
```

1 5 10 15

Val Lys Glu Glu Ile Lys Glu Val Lys Glu Glu Ile Lys Glu Val Lys
20 25 30

Glu Glu Ile Lys Glu
35

<210> SEQ ID NO 80
<211> LENGTH: 35
<212> TYPE: PRT
<213> ORGANISM: Plasmodium falciparum

<400> SEQUENCE: 80

Lys Asn Asp Ile Asn Val Gln Leu Asp Asp Ile Asn Val Gln Leu Asp
1 5 10 15

Asp Ile Asn Val Gln Leu Asp Asp Ile Asn Ile Gln Leu Asp Glu Ile
20 25 30

Asn Leu Asn
35

<210> SEQ ID NO 81
<211> LENGTH: 34
<212> TYPE: PRT
<213> ORGANISM: Plasmodium falciparum

<400> SEQUENCE: 81

Lys Ile Gln Ile Glu Glu Ile Lys Lys Glu Thr Asn Gln Ile Asn Lys
1 5 10 15

Asp Ile Asp His Ile Glu Met Asn Ile Ile Asn Leu Lys Lys Lys Ile
20 25 30

Glu Phe

<210> SEQ ID NO 82
<211> LENGTH: 33
<212> TYPE: PRT
<213> ORGANISM: Plasmodium falciparum

<400> SEQUENCE: 82

Asp Ser Met Asn Asn His Lys Asp Asp Met Asn Asn Tyr Asn Asp Asn
1 5 10 15

Ile Asn Asn Tyr Val Glu Ser Met Asn Asn Tyr Asp Asp Ile Met Asn
20 25 30

Lys

<210> SEQ ID NO 83
<211> LENGTH: 30
<212> TYPE: PRT
<213> ORGANISM: Plasmodium falciparum

<400> SEQUENCE: 83

Met Cys Glu Leu Asn Val Met Glu Asn Asn Met Asn Asn Ile His Ser
1 5 10 15

Asn Asn Asn Asn Ile Ser Thr His Met Asp Asp Val Ile Glu
20 25 30

<210> SEQ ID NO 84
<211> LENGTH: 29
<212> TYPE: PRT
<213> ORGANISM: Plasmodium falciparum

<400> SEQUENCE: 84

Lys Glu Ile Gln Met Leu Lys Asn Gln Ile Leu Ser Leu Glu Glu Ser

-continued 1 5 10 15

Ile Lys Ser Leu Asn Glu Phe Ile Asn Asn Leu Lys Asn
20 25

<210> SEQ ID NO 85
<211> LENGTH: 29
<212> TYPE: PRT
<213> ORGANISM: Plasmodium falciparum

<400> SEQUENCE: 85

Gly Gly Leu Lys Asn Ser Asn His Asn Leu Asn Asn Ile Glu Met Lys
1 5 10 15

Tyr Asn Thr Leu Asn Asn Asn Met Asn Ser Ile Asn Lys
20 25

<210> SEQ ID NO 86
<211> LENGTH: 28
<212> TYPE: PRT
<213> ORGANISM: Plasmodium falciparum

<400> SEQUENCE: 86

Glu Lys Leu Lys Lys Tyr Asn Asn Glu Ile Ser Ser Leu Lys Lys Glu
1 5 10 15

Leu Asp Ile Leu Asn Glu Lys Met Gly Lys Cys Thr
20 25

<210> SEQ ID NO 87
<211> LENGTH: 47
<212> TYPE: PRT
<213> ORGANISM: Plasmodium falciparum

<400> SEQUENCE: 87

Glu Lys Met Asn Met Lys Met Glu Gln Met Asp Met Lys Met Glu Lys
1 5 10 15

Ile Asp Val Asn Met Asp Gln Met Asp Val Lys Met Glu Gln Met Asp
20 25 30

Val Lys Met Glu Gln Met Asp Val Lys Met Lys Arg Met Asn Lys
35 40 45

<210> SEQ ID NO 88
<211> LENGTH: 55
<212> TYPE: PRT
<213> ORGANISM: Plasmodium falciparum

<400> SEQUENCE: 88

Lys Asn Lys Leu Asn Lys Lys Trp Glu Gln Ile Asn Asp His Ile Asn
1 5 10 15

Asn Leu Glu Thr Asn Ile Asn Asp Tyr Asn Lys Lys Ile Lys Glu Gly
20 25 30

Asp Ser Gln Leu Asn Asn Ile Gln Leu Gln Cys Glu Asn Ile Glu Gln
35 40 45

Lys Ile Asn Lys Ile Lys Glu
50 55

<210> SEQ ID NO 89
<211> LENGTH: 54
<212> TYPE: PRT
<213> ORGANISM: Plasmodium falciparum

<400> SEQUENCE: 89

Asn Glu Met Asn Lys Glu Val Asn Lys Met Asn Glu Glu Val Asn Lys
1 5 10 15

-continued

Met Asn Glu Glu Val Asn Lys Met Asn Glu Glu Val Asn Lys Met Asn
20 25 30

Lys Glu Val Asn Lys Met Asp Glu Glu Val Asn Lys Met Asn Lys Glu
35 40 45

Val Asn Lys Met Asn Lys
50

<210> SEQ ID NO 90
<211> LENGTH: 70
<212> TYPE: PRT
<213> ORGANISM: Plasmodium falciparum

<400> SEQUENCE: 90

Gln Asn Lys Met Glu Asn Asp Met Asn Ile Ile Lys Asn Asp Met Asn
1 5 10 15

Ile Met Glu Asn Asp Met Asn Ile Met Glu Asn Asp Met Asn Ile Ile
20 25 30

Lys Asn Asp Met Asn Ile Met Glu Lys Asp Met Asn Ile Ile Lys Asn
35 40 45

Asp Met Asn Ile Ile Lys Asn Asn Met Asn Ile Ile Lys Asn Glu Met
50 55 60

Asn Ile Ile Lys Asn Val
65 70

<210> SEQ ID NO 91
<211> LENGTH: 38
<212> TYPE: PRT
<213> ORGANISM: Plasmodium falciparum

<400> SEQUENCE: 91

Thr Lys Lys Leu Asn Lys Glu Leu Ser Glu Gly Asn Lys Glu Leu Glu
1 5 10 15

Lys Leu Glu Lys Asn Ile Lys Glu Leu Glu Glu Thr Asn Asn Thr Leu
20 25 30

Glu Asn Asp Ile Lys Val
35

<210> SEQ ID NO 92
<211> LENGTH: 31
<212> TYPE: PRT
<213> ORGANISM: Plasmodium falciparum

<400> SEQUENCE: 92

Glu Asn Ile Asn Asn Met Asp Glu Lys Ile Asn Asn Val Asp Glu Gln
1 5 10 15

Asn Asn Asn Met Asp Glu Lys Ile Asn Asn Val Asp Glu Lys Lys
20 25 30

<210> SEQ ID NO 93
<211> LENGTH: 27
<212> TYPE: PRT
<213> ORGANISM: Plasmodium falciparum

<400> SEQUENCE: 93

Ala Arg Asp Asp Ile Gln Lys Asp Ile Asn Lys Met Glu Ser Glu Leu
1 5 10 15

Ile Asn Val Ser Asn Glu Ile Asn Arg Leu Asp
20 25

<210> SEQ ID NO 94

<211> LENGTH: 22
<212> TYPE: PRT
<213> ORGANISM: Plasmodium falciparum

<400> SEQUENCE: 94

Glu Lys Lys Leu Asp Ile Leu Lys Val Asn Ile Ser Asn Ile Asn Asn
1 5 10 15

Ser Leu Asp Lys Leu Lys
20

<210> SEQ ID NO 95
<211> LENGTH: 39
<212> TYPE: PRT
<213> ORGANISM: Plasmodium falciparum

<400> SEQUENCE: 95

Asn Ser Leu Asp Tyr Tyr Lys Lys Val Ile Ile Lys Leu Lys Asn Asn
1 5 10 15

Ile Asn Asn Met Glu Glu Tyr Thr Asn Asn Ile Thr Asn Asp Ile Asn
20 25 30

Val Leu Lys Ala His Ile Asp
35

<210> SEQ ID NO 96
<211> LENGTH: 36
<212> TYPE: PRT
<213> ORGANISM: Plasmodium falciparum

<400> SEQUENCE: 96

Pro Asp Phe Asp Ala Tyr Asn Glu Lys Leu Gly Ser Ile Ser Gln Ser
1 5 10 15

Ile Asp Glu Ile Lys Lys Lys Ile Asp Asn Leu Gln Lys Glu Ile Lys
20 25 30

Val Ala Asn Lys
35

<210> SEQ ID NO 97
<211> LENGTH: 35
<212> TYPE: PRT
<213> ORGANISM: Plasmodium falciparum

<400> SEQUENCE: 97

Gln Leu Glu Glu Lys Thr Lys Gln Tyr Asn Asp Leu Gln Asn Asn Met
1 5 10 15

Lys Thr Ile Lys Glu Gln Asn Glu His Leu Lys Asn Lys Phe Gln Ser
20 25 30

Met Gly Lys
35

<210> SEQ ID NO 98
<211> LENGTH: 25
<212> TYPE: PRT
<213> ORGANISM: Plasmodium falciparum

<400> SEQUENCE: 98

Ile Ile Asp Ile Lys Lys His Leu Glu Lys Leu Lys Ile Glu Ile Lys
1 5 10 15

Glu Lys Lys Glu Asp Leu Glu Asn Leu
20 25

<210> SEQ ID NO 99
<211> LENGTH: 15

<212> TYPE: PRT
<213> ORGANISM: Plasmodium falciparum

<400> SEQUENCE: 99

Met Arg Lys Leu Ala Ile Leu Ser Val Ser Ser Phe Leu Phe Val
1 5 10 15

<210> SEQ ID NO 100
<211> LENGTH: 17
<212> TYPE: PRT
<213> ORGANISM: Plasmodium falciparum

<400> SEQUENCE: 100

Leu Val Asn Leu Leu Ile Phe His Ile Asn Gly Lys Ile Ile Lys Asn
1 5 10 15

Ser

<210> SEQ ID NO 101
<211> LENGTH: 15
<212> TYPE: PRT
<213> ORGANISM: Plasmodium falciparum

<400> SEQUENCE: 101

Met Asn Tyr Tyr Gly Lys Gln Glu Asn Trp Tyr Ser Leu Lys Lys
1 5 10 15

<210> SEQ ID NO 102
<211> LENGTH: 16
<212> TYPE: PRT
<213> ORGANISM: Plasmodium falciparum

<400> SEQUENCE: 102

Arg His Asn Trp Val Asn His Ala Val Pro Leu Ala Met Lys Leu Ile
1 5 10 15

<210> SEQ ID NO 103
<211> LENGTH: 15
<212> TYPE: PRT
<213> ORGANISM: Plasmodium falciparum

<400> SEQUENCE: 103

Val Lys Asn Val Ile Gly Pro Phe Met Lys Ala Val Cys Val Glu
1 5 10 15

<210> SEQ ID NO 104
<211> LENGTH: 15
<212> TYPE: PRT
<213> ORGANISM: Plasmodium falciparum

<400> SEQUENCE: 104

Ser Ser Val Phe Asn Val Val Asn Ser Ser Ile Gly Leu Ile Met
1 5 10 15

<210> SEQ ID NO 105
<211> LENGTH: 15
<212> TYPE: PRT
<213> ORGANISM: Plasmodium falciparum

<400> SEQUENCE: 105

Ala Gly Leu Leu Gly Asn Val Ser Thr Val Leu Leu Gly Gly Val
1 5 10 15

<210> SEQ ID NO 106
<211> LENGTH: 15
<212> TYPE: PRT

<213> ORGANISM: Plasmodium falciparum

<400> SEQUENCE: 106

Lys Ser Lys Tyr Lys Leu Ala Thr Ser Val Leu Ala Gly Leu Leu
1 5 10 15

<210> SEQ ID NO 107
<211> LENGTH: 15
<212> TYPE: PRT
<213> ORGANISM: Plasmodium falciparum

<400> SEQUENCE: 107

Gly Leu Ala Tyr Lys Phe Val Val Pro Gly Ala Ala Thr Pro Tyr
1 5 10 15

<210> SEQ ID NO 108
<211> LENGTH: 15
<212> TYPE: PRT
<213> ORGANISM: Plasmodium falciparum

<400> SEQUENCE: 108

His Asn Trp Val Asn His Ala Val Pro Leu Ala Met Lys Leu Ile
1 5 10 15

<210> SEQ ID NO 109
<211> LENGTH: 15
<212> TYPE: PRT
<213> ORGANISM: Plasmodium falciparum

<400> SEQUENCE: 109

Lys Tyr Lys Ile Ala Gly Gly Ile Ala Gly Gly Leu Ala Leu Leu
1 5 10 15

<210> SEQ ID NO 110
<211> LENGTH: 17
<212> TYPE: PRT
<213> ORGANISM: Plasmodium falciparum

<400> SEQUENCE: 110

Glu Lys Lys Ile Ala Lys Met Glu Lys Ala Ser Ser Val Phe Asn Val
1 5 10 15

Val

<210> SEQ ID NO 111
<211> LENGTH: 20
<212> TYPE: PRT
<213> ORGANISM: Plasmodium falciparum

<400> SEQUENCE: 111

Glu Tyr Leu Asn Lys Ile Gln Asn Ser Leu Ser Thr Glu Trp Ser Pro
1 5 10 15

Cys Ser Val Thr
20

<210> SEQ ID NO 112
<211> LENGTH: 8
<212> TYPE: PRT
<213> ORGANISM: Plasmodium falciparum

<400> SEQUENCE: 112

Lys Pro Asn Asp Lys Ser Leu Tyr
1 5

<210> SEQ ID NO 113

<211> LENGTH: 8
<212> TYPE: PRT
<213> ORGANISM: Plasmodium falciparum

<400> SEQUENCE: 113

Lys Pro Lys Asp Glu Leu Asp Tyr
1 5

<210> SEQ ID NO 114
<211> LENGTH: 9
<212> TYPE: PRT
<213> ORGANISM: Plasmodium falciparum

<400> SEQUENCE: 114

Lys Pro Ile Val Gln Tyr Asp Asn Phe
1 5

<210> SEQ ID NO 115
<211> LENGTH: 11
<212> TYPE: PRT
<213> ORGANISM: Plasmodium falciparum

<400> SEQUENCE: 115

Ala Ser Lys Asn Lys Glu Lys Ala Leu Ile Ile
1 5 10

<210> SEQ ID NO 116
<211> LENGTH: 9
<212> TYPE: PRT
<213> ORGANISM: Plasmodium falciparum

<400> SEQUENCE: 116

Gly Ile Ala Gly Gly Leu Ala Leu Leu
1 5

<210> SEQ ID NO 117
<211> LENGTH: 10
<212> TYPE: PRT
<213> ORGANISM: Plasmodium falciparum

<400> SEQUENCE: 117

Met Asn Pro Asn Asp Pro Asn Arg Asn Val
1 5 10

<210> SEQ ID NO 118
<211> LENGTH: 9
<212> TYPE: PRT
<213> ORGANISM: Plasmodium falciparum

<400> SEQUENCE: 118

Met Ile Asn Ala Tyr Leu Asp Lys Leu
1 5

<210> SEQ ID NO 119
<211> LENGTH: 8
<212> TYPE: PRT
<213> ORGANISM: Plasmodium falciparum

<400> SEQUENCE: 119

Ile Ser Lys Tyr Glu Asp Glu Ile
1 5

<210> SEQ ID NO 120
<211> LENGTH: 9
<212> TYPE: PRT
<213> ORGANISM: Plasmodium falciparum

<400> SEQUENCE: 120

His Leu Gly Asn Val Lys Tyr Leu Val
1 5

<210> SEQ ID NO 121
<211> LENGTH: 8
<212> TYPE: PRT
<213> ORGANISM: Plasmodium falciparum

<400> SEQUENCE: 121

Lys Ser Leu Tyr Asp Glu His Ile
1 5

<210> SEQ ID NO 122
<211> LENGTH: 9
<212> TYPE: PRT
<213> ORGANISM: Plasmodium falciparum

<400> SEQUENCE: 122

Leu Leu Met Asp Cys Ser Gly Ser Ile
1 5

<210> SEQ ID NO 123
<211> LENGTH: 8
<212> TYPE: PRT
<213> ORGANISM: Plasmodium falciparum

<400> SEQUENCE: 123

Lys Ser Lys Asp Glu Leu Asp Tyr
1 5

<210> SEQ ID NO 124
<211> LENGTH: 9
<212> TYPE: PRT
<213> ORGANISM: Plasmodium falciparum

<400> SEQUENCE: 124

Ile Pro Ser Leu Ala Leu Met Leu Ile
1 5

<210> SEQ ID NO 125
<211> LENGTH: 9
<212> TYPE: PRT
<213> ORGANISM: Plasmodium falciparum

<400> SEQUENCE: 125

Met Pro Leu Glu Thr Gln Leu Ala Ile
1 5

<210> SEQ ID NO 126
<211> LENGTH: 9
<212> TYPE: PRT
<213> ORGANISM: Plasmodium falciparum

<400> SEQUENCE: 126

Met Pro Asn Asp Pro Asn Arg Asn Val
1 5

<210> SEQ ID NO 127
<211> LENGTH: 9
<212> TYPE: PRT
<213> ORGANISM: Plasmodium falciparum

<400> SEQUENCE: 127

Tyr Leu Asn Lys Ile Gln Asn Ser Leu
1 5

<210> SEQ ID NO 128
<211> LENGTH: 9
<212> TYPE: PRT
<213> ORGANISM: Plasmodium falciparum

<400> SEQUENCE: 128

Met Glu Lys Leu Lys Glu Leu Glu Lys
1 5

<210> SEQ ID NO 129
<211> LENGTH: 8
<212> TYPE: PRT
<213> ORGANISM: Plasmodium falciparum

<400> SEQUENCE: 129

Ala Thr Ser Val Leu Ala Gly Leu
1 5

<210> SEQ ID NO 130
<211> LENGTH: 9
<212> TYPE: PRT
<213> ORGANISM: Human immunodeficiency virus

<400> SEQUENCE: 130

Pro Leu Asp Glu Gly Phe Arg Lys Tyr
1 5

<210> SEQ ID NO 131
<211> LENGTH: 9
<212> TYPE: PRT
<213> ORGANISM: Human immunodeficiency virus

<400> SEQUENCE: 131

Leu Leu Gln Leu Thr Val Trp Gly Ile
1 5

<210> SEQ ID NO 132
<211> LENGTH: 9
<212> TYPE: PRT
<213> ORGANISM: Human immunodeficiency virus

<400> SEQUENCE: 132

Tyr Thr Ala Phe Thr Ile Pro Ser Ile
1 5

<210> SEQ ID NO 133
<211> LENGTH: 9
<212> TYPE: PRT
<213> ORGANISM: Human immunodeficiency virus

<400> SEQUENCE: 133

Gly Leu Asn Lys Ile Val Arg Met Tyr
1 5

<210> SEQ ID NO 134
<211> LENGTH: 9
<212> TYPE: PRT
<213> ORGANISM: Human immunodeficiency virus

<400> SEQUENCE: 134

Ile Leu Lys Asp Pro Val His Gly Val
1 5

<210> SEQ ID NO 135
<211> LENGTH: 9
<212> TYPE: PRT
<213> ORGANISM: Human immunodeficiency virus

<400> SEQUENCE: 135

Tyr Thr Ala Phe Thr Ile Pro Ser Ile
1               5

<210> SEQ ID NO 136
<211> LENGTH: 10
<212> TYPE: PRT
<213> ORGANISM: Human immunodeficiency virus

<400> SEQUENCE: 136

Ile Ile Gly Arg Asn Leu Leu Thr Gln Ile
1               5                   10

<210> SEQ ID NO 137
<211> LENGTH: 9
<212> TYPE: PRT
<213> ORGANISM: Human immunodeficiency virus

<400> SEQUENCE: 137

Lys Gly Pro Ala Lys Leu Leu Trp Lys
1               5

<210> SEQ ID NO 138
<211> LENGTH: 9
<212> TYPE: PRT
<213> ORGANISM: Human immunodeficiency virus

<400> SEQUENCE: 138

Val Leu Phe Leu Asp Gly Ile Asp Lys
1               5

<210> SEQ ID NO 139
<211> LENGTH: 9
<212> TYPE: PRT
<213> ORGANISM: Human immunodeficiency virus

<400> SEQUENCE: 139

Ala Val Phe Ile His Asn Phe Lys Arg
1               5

<210> SEQ ID NO 140
<211> LENGTH: 9
<212> TYPE: PRT
<213> ORGANISM: Human immunodeficiency virus

<400> SEQUENCE: 140

His Asn Phe Lys Arg Lys Gly Gly Ile
1               5

<210> SEQ ID NO 141
<211> LENGTH: 9
<212> TYPE: PRT
<213> ORGANISM: Human immunodeficiency virus

<400> SEQUENCE: 141

Ile Val Trp Gln Val Asp Arg Met Arg
1               5

<210> SEQ ID NO 142
<211> LENGTH: 9

<212> TYPE: PRT
<213> ORGANISM: Human immunodeficiency virus

<400> SEQUENCE: 142

Ser Asp Ile Lys Val Val Pro Arg Arg
1 5

<210> SEQ ID NO 143
<211> LENGTH: 9
<212> TYPE: PRT
<213> ORGANISM: Human immunodeficiency virus

<400> SEQUENCE: 143

Tyr Thr Ala Phe Thr Ile Pro Ser Ile
1 5

<210> SEQ ID NO 144
<211> LENGTH: 9
<212> TYPE: PRT
<213> ORGANISM: Human immunodeficiency virus

<400> SEQUENCE: 144

Leu Gly Ile Pro His Pro Ala Gly Leu
1 5

<210> SEQ ID NO 145
<211> LENGTH: 9
<212> TYPE: PRT
<213> ORGANISM: Human immunodeficiency virus

<400> SEQUENCE: 145

Phe Ser Val Pro Leu Asp Glu Gly Phe
1 5

<210> SEQ ID NO 146
<211> LENGTH: 9
<212> TYPE: PRT
<213> ORGANISM: Human immunodeficiency virus

<400> SEQUENCE: 146

Ala Val Phe Ile His Asn Phe Lys Arg
1 5

<210> SEQ ID NO 147
<211> LENGTH: 9
<212> TYPE: PRT
<213> ORGANISM: Human immunodeficiency virus

<400> SEQUENCE: 147

Arg Trp Ile Ile Leu Gly Leu Asn Lys
1 5

<210> SEQ ID NO 148
<211> LENGTH: 9
<212> TYPE: PRT
<213> ORGANISM: Human immunodeficiency virus

<400> SEQUENCE: 148

Ala Ile Phe Gln Ser Ser Met Thr Lys
1 5

<210> SEQ ID NO 149
<211> LENGTH: 9
<212> TYPE: PRT
<213> ORGANISM: Human immunodeficiency virus

<400> SEQUENCE: 149

Ala Val Phe Ile His Asn Phe Lys Arg
1               5

<210> SEQ ID NO 150
<211> LENGTH: 9
<212> TYPE: PRT
<213> ORGANISM: Human immunodeficiency virus

<400> SEQUENCE: 150

Ala Val Phe Ile His Asn Phe Lys Arg
1               5

<210> SEQ ID NO 151
<211> LENGTH: 9
<212> TYPE: PRT
<213> ORGANISM: Human immunodeficiency virus

<400> SEQUENCE: 151

Trp Gln Val Met Ile Val Trp Gln Val
1               5

<210> SEQ ID NO 152
<211> LENGTH: 9
<212> TYPE: PRT
<213> ORGANISM: Human immunodeficiency virus

<400> SEQUENCE: 152

Tyr Ser Pro Val Ser Ile Leu Asp Ile
1               5

<210> SEQ ID NO 153
<211> LENGTH: 9
<212> TYPE: PRT
<213> ORGANISM: Human immunodeficiency virus

<400> SEQUENCE: 153

Ala Pro Arg Lys Lys Gly Cys Trp Lys
1               5

<210> SEQ ID NO 154
<211> LENGTH: 9
<212> TYPE: PRT
<213> ORGANISM: Human immunodeficiency virus

<400> SEQUENCE: 154

Leu Lys Asp Pro Val His Gly Val Tyr
1               5

<210> SEQ ID NO 155
<211> LENGTH: 9
<212> TYPE: PRT
<213> ORGANISM: Human immunodeficiency virus

<400> SEQUENCE: 155

Tyr Thr Ala Phe Thr Ile Pro Ser Ile
1               5

<210> SEQ ID NO 156
<211> LENGTH: 9
<212> TYPE: PRT
<213> ORGANISM: Human immunodeficiency virus

<400> SEQUENCE: 156

Thr Leu Asn Phe Pro Ile Ser Pro Ile 1 5

<210> SEQ ID NO 157
<211> LENGTH: 9
<212> TYPE: PRT
<213> ORGANISM: Human immunodeficiency virus

<400> SEQUENCE: 157

Phe Lys Arg Lys Gly Gly Ile Gly Gly
1 5

<210> SEQ ID NO 158
<211> LENGTH: 9
<212> TYPE: PRT
<213> ORGANISM: Human immunodeficiency virus

<400> SEQUENCE: 158

Leu Leu Gln Leu Thr Val Trp Gly Ile
1 5

<210> SEQ ID NO 159
<211> LENGTH: 10
<212> TYPE: PRT
<213> ORGANISM: Human immunodeficiency virus

<400> SEQUENCE: 159

Glu Ile Leu Lys Asp Pro Val His Gly Val
1 5 10

<210> SEQ ID NO 160
<211> LENGTH: 9
<212> TYPE: PRT
<213> ORGANISM: Human immunodeficiency virus

<400> SEQUENCE: 160

Gly Ile Pro His Pro Ala Gly Leu Lys
1 5

<210> SEQ ID NO 161
<211> LENGTH: 9
<212> TYPE: PRT
<213> ORGANISM: Human immunodeficiency virus

<400> SEQUENCE: 161

Gly Pro Ala Lys Leu Leu Trp Lys Gly
1 5

<210> SEQ ID NO 162
<211> LENGTH: 9
<212> TYPE: PRT
<213> ORGANISM: Human immunodeficiency virus

<400> SEQUENCE: 162

Ser Gln Gly Ile Arg Lys Val Leu Phe
1 5

<210> SEQ ID NO 163
<211> LENGTH: 9
<212> TYPE: PRT
<213> ORGANISM: Human immunodeficiency virus

<400> SEQUENCE: 163

Ser Asp Leu Glu Ile Gly Gln His Arg
1 5

<210> SEQ ID NO 164
<211> LENGTH: 9
<212> TYPE: PRT
<213> ORGANISM: Human immunodeficiency virus

<400> SEQUENCE: 164

Leu Val Ser Gln Gly Ile Arg Lys Val
1 5

<210> SEQ ID NO 165
<211> LENGTH: 9
<212> TYPE: PRT
<213> ORGANISM: Human immunodeficiency virus

<400> SEQUENCE: 165

Gln Gly Ile Arg Lys Val Leu Phe Leu
1 5

<210> SEQ ID NO 166
<211> LENGTH: 9
<212> TYPE: PRT
<213> ORGANISM: Human immunodeficiency virus

<400> SEQUENCE: 166

Glu Glu Ala Glu Leu Glu Leu Ala Glu
1 5

<210> SEQ ID NO 167
<211> LENGTH: 9
<212> TYPE: PRT
<213> ORGANISM: Human immunodeficiency virus

<400> SEQUENCE: 167

Phe Thr Ile Pro Ser Ile Asn Asn Glu
1 5

<210> SEQ ID NO 168
<211> LENGTH: 9
<212> TYPE: PRT
<213> ORGANISM: Human immunodeficiency virus

<400> SEQUENCE: 168

Phe Lys Arg Lys Gly Gly Ile Gly Gly
1 5

<210> SEQ ID NO 169
<211> LENGTH: 9
<212> TYPE: PRT
<213> ORGANISM: Human immunodeficiency virus

<400> SEQUENCE: 169

Lys Gly Pro Ala Lys Leu Leu Trp Lys
1 5

<210> SEQ ID NO 170
<211> LENGTH: 9
<212> TYPE: PRT
<213> ORGANISM: Human immunodeficiency virus

<400> SEQUENCE: 170

Leu Leu Thr Gln Ile Gly Cys Thr Leu
1 5

<210> SEQ ID NO 171
<211> LENGTH: 9
<212> TYPE: PRT

<213> ORGANISM: Human immunodeficiency virus

<400> SEQUENCE: 171

Lys Gly Pro Ala Lys Leu Leu Trp Lys
1 5

<210> SEQ ID NO 172
<211> LENGTH: 10
<212> TYPE: PRT
<213> ORGANISM: Human immunodeficiency virus

<400> SEQUENCE: 172

Tyr Thr Ala Phe Thr Ile Pro Ser Ile Asn
1 5 10

<210> SEQ ID NO 173
<211> LENGTH: 9
<212> TYPE: PRT
<213> ORGANISM: Human immunodeficiency virus

<400> SEQUENCE: 173

Leu Tyr Val Gly Ser Asp Leu Glu Ile
1 5

<210> SEQ ID NO 174
<211> LENGTH: 9
<212> TYPE: PRT
<213> ORGANISM: Human immunodeficiency virus

<400> SEQUENCE: 174

Leu Leu Thr Gln Ile Gly Cys Thr Leu
1 5

<210> SEQ ID NO 175
<211> LENGTH: 9
<212> TYPE: PRT
<213> ORGANISM: Human immunodeficiency virus

<400> SEQUENCE: 175

Asp Phe Trp Glu Val Gln Leu Gly Ile
1 5

<210> SEQ ID NO 176
<211> LENGTH: 9
<212> TYPE: PRT
<213> ORGANISM: Human immunodeficiency virus

<400> SEQUENCE: 176

Leu Leu Trp Lys Gly Glu Gly Ala Val
1 5

<210> SEQ ID NO 177
<211> LENGTH: 9
<212> TYPE: PRT
<213> ORGANISM: Human immunodeficiency virus

<400> SEQUENCE: 177

Met Ile Val Trp Gln Val Asp Arg Met
1 5

<210> SEQ ID NO 178
<211> LENGTH: 9
<212> TYPE: PRT
<213> ORGANISM: Human immunodeficiency virus

<400> SEQUENCE: 178

Phe Pro Ile Ser Pro Ile Glu Thr Val
1 5

<210> SEQ ID NO 179
<211> LENGTH: 9
<212> TYPE: PRT
<213> ORGANISM: Human immunodeficiency virus

<400> SEQUENCE: 179

Ala Gly Leu Lys Lys Lys Lys Ser Val
1 5

<210> SEQ ID NO 180
<211> LENGTH: 9
<212> TYPE: PRT
<213> ORGANISM: Human immunodeficiency virus

<400> SEQUENCE: 180

Ala Pro Arg Lys Lys Gly Cys Trp Lys
1 5

<210> SEQ ID NO 181
<211> LENGTH: 9
<212> TYPE: PRT
<213> ORGANISM: Human immunodeficiency virus

<400> SEQUENCE: 181

Ile Ser Pro Ile Glu Thr Val Pro Val
1 5

<210> SEQ ID NO 182
<211> LENGTH: 9
<212> TYPE: PRT
<213> ORGANISM: Human immunodeficiency virus

<400> SEQUENCE: 182

Trp Glu Val Gln Leu Gly Ile Pro His
1 5

<210> SEQ ID NO 183
<211> LENGTH: 9
<212> TYPE: PRT
<213> ORGANISM: Human immunodeficiency virus

<400> SEQUENCE: 183

Ala Ile Phe Gln Ser Ser Met Thr Lys
1 5

<210> SEQ ID NO 184
<211> LENGTH: 9
<212> TYPE: PRT
<213> ORGANISM: Human immunodeficiency virus

<400> SEQUENCE: 184

Gly Ile Pro His Pro Ala Gly Leu Lys
1 5

<210> SEQ ID NO 185
<211> LENGTH: 9
<212> TYPE: PRT
<213> ORGANISM: Human immunodeficiency virus

<400> SEQUENCE: 185

Ala Glu Leu Glu Leu Ala Glu Asn Arg
1 5

<210> SEQ ID NO 186
<211> LENGTH: 9
<212> TYPE: PRT
<213> ORGANISM: Human immunodeficiency virus

<400> SEQUENCE: 186

Ser Asp Ile Lys Val Val Pro Arg Arg
1 5

<210> SEQ ID NO 187
<211> LENGTH: 9
<212> TYPE: PRT
<213> ORGANISM: Human immunodeficiency virus

<400> SEQUENCE: 187

Leu Thr Glu Glu Ala Glu Leu Glu Leu
1 5

<210> SEQ ID NO 188
<211> LENGTH: 9
<212> TYPE: PRT
<213> ORGANISM: Human immunodeficiency virus

<400> SEQUENCE: 188

Ser Pro Ala Ile Phe Gln Ser Ser Met
1 5

<210> SEQ ID NO 189
<211> LENGTH: 20
<212> TYPE: PRT
<213> ORGANISM: Artificial sequence
<220> FEATURE:
<223> OTHER INFORMATION: Synthetic construct; combined HIV CTL epitopes

<400> SEQUENCE: 189

Pro Leu Asp Glu Gly Phe Arg Lys Tyr Thr Ala Phe Thr Ile Pro Ser
1 5 10 15

Ile Asn Asn Glu
20

<210> SEQ ID NO 190
<211> LENGTH: 15
<212> TYPE: PRT
<213> ORGANISM: Artificial sequence
<220> FEATURE:
<223> OTHER INFORMATION: Synthetic construct; combined HIV CTL epitopes

<400> SEQUENCE: 190

Ala Val Phe Ile His Asn Phe Lys Arg Lys Gly Gly Ile Gly Gly
1 5 10 15

<210> SEQ ID NO 191
<211> LENGTH: 26
<212> TYPE: PRT
<213> ORGANISM: Artificial sequence
<220> FEATURE:
<223> OTHER INFORMATION: Synthetic construct; combined HIV CTL epitopes

<400> SEQUENCE: 191

Ile Ile Gly Arg Asn Leu Leu Thr Gln Ile Gly Cys Thr Leu Asn Phe
1 5 10 15

Pro Ile Ser Pro Ile Glu Thr Val Pro Val
20 25

<210> SEQ ID NO 192
<211> LENGTH: 21
<212> TYPE: PRT
<213> ORGANISM: Artificial sequence
<220> FEATURE:
<223> OTHER INFORMATION: Synthetic construct; combined HIV CTL epitopes

<400> SEQUENCE: 192

Asp Phe Trp Glu Val Gln Leu Gly Ile Pro His Pro Ala Gly Leu Lys
1 5 10 15

Lys Lys Lys Ser Val
20

<210> SEQ ID NO 193
<211> LENGTH: 23
<212> TYPE: PRT
<213> ORGANISM: Artificial sequence
<220> FEATURE:
<223> OTHER INFORMATION: Synthetic construct; combined HIV CTL epitopes

<400> SEQUENCE: 193

Leu Thr Glu Glu Ala Glu Leu Glu Leu Ala Glu Asn Arg Glu Ile Leu
1 5 10 15

Lys Asp Pro Val His Gly Val
20

<210> SEQ ID NO 194
<211> LENGTH: 14
<212> TYPE: PRT
<213> ORGANISM: Artificial sequence
<220> FEATURE:
<223> OTHER INFORMATION: Synthetic construct; combined HIV CTL epitopes

<400> SEQUENCE: 194

Lys Gly Pro Ala Lys Leu Leu Trp Lys Gly Glu Gly Ala Val
1 5 10

<210> SEQ ID NO 195
<211> LENGTH: 17
<212> TYPE: PRT
<213> ORGANISM: Artificial sequence
<220> FEATURE:
<223> OTHER INFORMATION: Synthetic construct; combined HIV CTL epitopes

<400> SEQUENCE: 195

Leu Val Ser Gln Gly Ile Arg Lys Val Leu Phe Leu Asp Gly Ile Asp
1 5 10 15

Lys

<210> SEQ ID NO 196
<211> LENGTH: 22
<212> TYPE: PRT
<213> ORGANISM: Artificial sequence
<220> FEATURE:
<223> OTHER INFORMATION: Synthetic construct; combined HIV CTL epitopes

<400> SEQUENCE: 196

Arg Trp Ile Ile Leu Gly Leu Asn Lys Ile Val Arg Met Tyr Ser Pro
1 5 10 15

Val Ser Ile Leu Asp Ile
20

<210> SEQ ID NO 197
<211> LENGTH: 13
<212> TYPE: PRT
<213> ORGANISM: Artificial sequence
<220> FEATURE:
<223> OTHER INFORMATION: Synthetic construct; combined HIV CTL epitopes

<400> SEQUENCE: 197

Trp Gln Val Met Ile Val Trp Gln Val Asp Arg Met Arg
1 5 10

<210> SEQ ID NO 198
<211> LENGTH: 11
<212> TYPE: PRT
<213> ORGANISM: Artificial sequence
<220> FEATURE:
<223> OTHER INFORMATION: Synthetic construct; combined HIV CTL epitopes

<400> SEQUENCE: 198

Ser Pro Ala Ile Phe Gln Ser Ser Met Thr Lys
1 5 10

<210> SEQ ID NO 199
<211> LENGTH: 9
<212> TYPE: PRT
<213> ORGANISM: Artificial sequence
<220> FEATURE:
<223> OTHER INFORMATION: Synthetic construct; combined HIV CTL epitopes

<400> SEQUENCE: 199

Ser Asp Ile Lys Val Val Pro Arg Arg
1 5

<210> SEQ ID NO 200
<211> LENGTH: 9
<212> TYPE: PRT
<213> ORGANISM: Artificial sequence
<220> FEATURE:
<223> OTHER INFORMATION: Synthetic construct; combined HIV CTL epitopes

<400> SEQUENCE: 200

Leu Leu Gln Leu Thr Val Trp Gly Ile
1 5

<210> SEQ ID NO 201
<211> LENGTH: 9
<212> TYPE: PRT
<213> ORGANISM: Artificial sequence
<220> FEATURE:
<223> OTHER INFORMATION: Synthetic construct; combined HIV CTL epitopes

<400> SEQUENCE: 201

Ala Pro Arg Lys Lys Gly Cys Trp Lys
1 5

<210> SEQ ID NO 202
<211> LENGTH: 13
<212> TYPE: PRT
<213> ORGANISM: Artificial sequence
<220> FEATURE:
<223> OTHER INFORMATION: Synthetic construct; combined HIV CTL epitopes

<400> SEQUENCE: 202

Leu Tyr Val Gly Ser Asp Leu Glu Ile Gly Gln His Arg
1 5 10

<210> SEQ ID NO 203
<211> LENGTH: 24
<212> TYPE: PRT
<213> ORGANISM: Influenza A virus

<400> SEQUENCE: 203

-continued

Ser Leu Leu Thr Glu Val Glu Thr Pro Ile Arg Asn Glu Trp Gly Cys
1               5                   10                  15

Arg Cys Asn Asp Ser Ser Asp Pro
            20

<210> SEQ ID NO 204
<211> LENGTH: 24
<212> TYPE: PRT
<213> ORGANISM: Influenza A virus

<400> SEQUENCE: 204

Ser Leu Leu Thr Glu Val Glu Thr Pro Ile Arg Asn Glu Trp Gly Cys
1               5                   10                  15

Arg Cys Asn Gly Ser Ser Asp Pro
            20

<210> SEQ ID NO 205
<211> LENGTH: 24
<212> TYPE: PRT
<213> ORGANISM: Influenza A virus

<400> SEQUENCE: 205

Ser Leu Leu Thr Glu Val Glu Thr Pro Ile Arg Asn Glu Trp Gly Cys
1               5                   10                  15

Lys Cys Asn Asp Ser Ser Asp Pro
            20

<210> SEQ ID NO 206
<211> LENGTH: 24
<212> TYPE: PRT
<213> ORGANISM: Influenza A virus

<400> SEQUENCE: 206

Ser Leu Leu Thr Glu Val Glu Thr Pro Thr Arg Asn Glu Trp Glu Cys
1               5                   10                  15

Arg Cys Ser Asp Ser Ser Asp Pro
            20

<210> SEQ ID NO 207
<211> LENGTH: 24
<212> TYPE: PRT
<213> ORGANISM: Influenza A virus

<400> SEQUENCE: 207

Ser Leu Leu Thr Glu Val Glu Thr Leu Thr Arg Asn Gly Trp Gly Cys
1               5                   10                  15

Arg Cys Ser Asp Ser Ser Asp Pro
            20

<210> SEQ ID NO 208
<211> LENGTH: 24
<212> TYPE: PRT
<213> ORGANISM: Influenza A virus

<400> SEQUENCE: 208

Ser Leu Leu Thr Glu Val Glu Thr Leu Thr Arg Asn Gly Trp Glu Cys
1               5                   10                  15

Lys Cys Arg Asp Ser Ser Asp Pro
            20

<210> SEQ ID NO 209
<211> LENGTH: 24

-continued

<212> TYPE: PRT
<213> ORGANISM: Influenza A virus

<400> SEQUENCE: 209

Ser Leu Leu Thr Glu Val Glu Thr Pro Thr Arg Asn Gly Trp Glu Cys
1 5 10 15

Lys Cys Ser Asp Ser Ser Asp Pro
20

<210> SEQ ID NO 210
<211> LENGTH: 24
<212> TYPE: PRT
<213> ORGANISM: Influenza A virus

<400> SEQUENCE: 210

Ser Leu Leu Thr Glu Val Glu Thr Pro Thr Arg Asn Gly Trp Gly Cys
1 5 10 15

Arg Cys Ser Gly Ser Ser Asp Pro
20

<210> SEQ ID NO 211
<211> LENGTH: 10
<212> TYPE: PRT
<213> ORGANISM: Influenza A virus

<400> SEQUENCE: 211

Ser Ile Gln Ser Arg Gly Leu Phe Gly Ala
1 5 10

<210> SEQ ID NO 212
<211> LENGTH: 10
<212> TYPE: PRT
<213> ORGANISM: Influenza A virus

<400> SEQUENCE: 212

Gln Ile Glu Ser Arg Gly Leu Phe Gly Ala
1 5 10

<210> SEQ ID NO 213
<211> LENGTH: 10
<212> TYPE: PRT
<213> ORGANISM: Influenza A virus

<400> SEQUENCE: 213

Glu Arg Gln Thr Arg Gly Ile Phe Gly Ala
1 5 10

<210> SEQ ID NO 214
<211> LENGTH: 10
<212> TYPE: PRT
<213> ORGANISM: Influenza A virus

<400> SEQUENCE: 214

Glu Lys Ala Thr Arg Gly Leu Phe Gly Ala
1 5 10

<210> SEQ ID NO 215
<211> LENGTH: 10
<212> TYPE: PRT
<213> ORGANISM: Influenza A virus

<400> SEQUENCE: 215

Lys Arg Lys Thr Arg Gly Leu Phe Gly Ala
1 5 10

<210> SEQ ID NO 216
<211> LENGTH: 10
<212> TYPE: PRT
<213> ORGANISM: Influenza A virus

<400> SEQUENCE: 216

Arg Arg Lys Lys Arg Gly Leu Phe Gly Ala
1 5 10

<210> SEQ ID NO 217
<211> LENGTH: 10
<212> TYPE: PRT
<213> ORGANISM: Influenza A virus

<400> SEQUENCE: 217

Gln Ile Ala Thr Arg Gly Leu Phe Gly Ala
1 5 10

<210> SEQ ID NO 218
<211> LENGTH: 10
<212> TYPE: PRT
<213> ORGANISM: Influenza A virus

<400> SEQUENCE: 218

Ile Pro Lys Gly Arg Gly Leu Phe Gly Ala
1 5 10

<210> SEQ ID NO 219
<211> LENGTH: 10
<212> TYPE: PRT
<213> ORGANISM: Influenza A virus

<400> SEQUENCE: 219

Lys Lys Lys Gly Arg Gly Leu Phe Gly Ala
1 5 10

<210> SEQ ID NO 220
<211> LENGTH: 10
<212> TYPE: PRT
<213> ORGANISM: Influenza A virus

<400> SEQUENCE: 220

Lys Arg Glu Lys Arg Gly Leu Phe Gly Ala
1 5 10

<210> SEQ ID NO 221
<211> LENGTH: 10
<212> TYPE: PRT
<213> ORGANISM: Influenza A virus

<400> SEQUENCE: 221

Ser Ile Glu Pro Lys Gly Leu Phe Gly Ala
1 5 10

<210> SEQ ID NO 222
<211> LENGTH: 10
<212> TYPE: PRT
<213> ORGANISM: Influenza A virus

<400> SEQUENCE: 222

Ala Ala Ser Tyr Arg Gly Leu Phe Gly Ala
1 5 10

<210> SEQ ID NO 223
<211> LENGTH: 10

<212> TYPE: PRT
<213> ORGANISM: Influenza A virus

<400> SEQUENCE: 223

Ile Ile Gln Gly Arg Gly Leu Phe Gly Ala
1 5 10

<210> SEQ ID NO 224
<211> LENGTH: 10
<212> TYPE: PRT
<213> ORGANISM: Influenza A virus

<400> SEQUENCE: 224

Ala Ile Ala Thr Arg Gly Leu Phe Gly Ala
1 5 10

<210> SEQ ID NO 225
<211> LENGTH: 10
<212> TYPE: PRT
<213> ORGANISM: Influenza A virus

<400> SEQUENCE: 225

Ala Ile Ser Asn Arg Gly Leu Phe Gly Ala
1 5 10

<210> SEQ ID NO 226
<211> LENGTH: 10
<212> TYPE: PRT
<213> ORGANISM: Influenza B virus

<400> SEQUENCE: 226

Leu Leu Lys Glu Arg Gly Phe Phe Gly Ala
1 5 10

<210> SEQ ID NO 227
<211> LENGTH: 27
<212> TYPE: PRT
<213> ORGANISM: Artificial sequence
<220> FEATURE:
<223> OTHER INFORMATION: Synthetic construct; combined influenza A virus
B-cell epitopes

<400> SEQUENCE: 227

Ser Ile Gln Ser Arg Gly Leu Phe Gly Asp Ile Glu Ser Arg Gly Leu
1 5 10 15

Phe Gly Glu Arg Gln Thr Arg Gly Ile Phe Gly
20 25

<210> SEQ ID NO 228
<211> LENGTH: 9
<212> TYPE: PRT
<213> ORGANISM: Influenza A virus

<400> SEQUENCE: 228

Ile Arg His Glu Asn Arg Met Val Leu
1 5

<210> SEQ ID NO 229
<211> LENGTH: 9
<212> TYPE: PRT
<213> ORGANISM: Influenza A virus

<400> SEQUENCE: 229

Gln Ala Tyr Gln Lys Arg Met Gly Val
1 5

-continued

<210> SEQ ID NO 230
<211> LENGTH: 9
<212> TYPE: PRT
<213> ORGANISM: Influenza A virus

<400> SEQUENCE: 230

Leu Lys Met Pro Ala Ser Arg Tyr Leu
1               5

<210> SEQ ID NO 231
<211> LENGTH: 9
<212> TYPE: PRT
<213> ORGANISM: Influenza A virus

<400> SEQUENCE: 231

Ser Arg Tyr Leu Thr Asp Met Thr Leu
1               5

<210> SEQ ID NO 232
<211> LENGTH: 9
<212> TYPE: PRT
<213> ORGANISM: Influenza A virus

<400> SEQUENCE: 232

Phe Met Leu Met Pro Lys Gln Lys Val
1               5

<210> SEQ ID NO 233
<211> LENGTH: 9
<212> TYPE: PRT
<213> ORGANISM: Influenza A virus

<400> SEQUENCE: 233

Met Arg Met Gly Asp Phe His Ser Leu
1               5

<210> SEQ ID NO 234
<211> LENGTH: 9
<212> TYPE: PRT
<213> ORGANISM: Influenza A virus

<400> SEQUENCE: 234

Tyr Leu Leu Ala Trp Lys Gln Val Leu
1               5

<210> SEQ ID NO 235
<211> LENGTH: 9
<212> TYPE: PRT
<213> ORGANISM: Influenza A virus

<400> SEQUENCE: 235

Ala Pro Ile Glu His Ile Ala Ser Met
1               5

<210> SEQ ID NO 236
<211> LENGTH: 9
<212> TYPE: PRT
<213> ORGANISM: Influenza A virus

<400> SEQUENCE: 236

Arg Arg Asn Tyr Phe Thr Ala Glu Val
1               5

<210> SEQ ID NO 237
<211> LENGTH: 9

<212> TYPE: PRT
<213> ORGANISM: Influenza A virus

<400> SEQUENCE: 237

Ile Gln Met Cys Thr Glu Leu Lys Leu
1 5

<210> SEQ ID NO 238
<211> LENGTH: 9
<212> TYPE: PRT
<213> ORGANISM: Influenza A virus

<400> SEQUENCE: 238

Ala Ala Gly Ala Ala Val Lys Gly Val
1 5

<210> SEQ ID NO 239
<211> LENGTH: 9
<212> TYPE: PRT
<213> ORGANISM: Influenza A virus

<400> SEQUENCE: 239

Val Gly Thr Met Val Met Glu Leu Ile
1 5

<210> SEQ ID NO 240
<211> LENGTH: 9
<212> TYPE: PRT
<213> ORGANISM: Influenza A virus

<400> SEQUENCE: 240

Asn Pro Thr Leu Leu Phe Leu Lys Val
1 5

<210> SEQ ID NO 241
<211> LENGTH: 9
<212> TYPE: PRT
<213> ORGANISM: Influenza A virus

<400> SEQUENCE: 241

Arg Leu Ile Asp Phe Leu Lys Asp Val
1 5

<210> SEQ ID NO 242
<211> LENGTH: 9
<212> TYPE: PRT
<213> ORGANISM: Influenza A virus

<400> SEQUENCE: 242

Met Gln Ile Arg Gly Phe Val Tyr Phe
1 5

<210> SEQ ID NO 243
<211> LENGTH: 9
<212> TYPE: PRT
<213> ORGANISM: Influenza A virus

<400> SEQUENCE: 243

Ile Met Phe Ser Asn Lys Met Ala Arg
1 5

<210> SEQ ID NO 244
<211> LENGTH: 9
<212> TYPE: PRT
<213> ORGANISM: Influenza A virus

<400> SEQUENCE: 244

Met Phe Ser Asn Lys Met Ala Arg Leu
1 5

<210> SEQ ID NO 245
<211> LENGTH: 9
<212> TYPE: PRT
<213> ORGANISM: Influenza A virus

<400> SEQUENCE: 245

Glu Arg Asn Glu Gln Gly Gln Thr Leu
1 5

<210> SEQ ID NO 246
<211> LENGTH: 9
<212> TYPE: PRT
<213> ORGANISM: Influenza A virus

<400> SEQUENCE: 246

Val Ala Tyr Met Leu Glu Arg Glu Leu
1 5

<210> SEQ ID NO 247
<211> LENGTH: 9
<212> TYPE: PRT
<213> ORGANISM: Influenza A virus

<400> SEQUENCE: 247

Leu Arg His Phe Gln Lys Asp Ala Lys
1 5

<210> SEQ ID NO 248
<211> LENGTH: 9
<212> TYPE: PRT
<213> ORGANISM: Influenza A virus

<400> SEQUENCE: 248

Val Arg Asp Gln Arg Gly Asn Val Leu
1 5

<210> SEQ ID NO 249
<211> LENGTH: 9
<212> TYPE: PRT
<213> ORGANISM: Homo sapiens

<400> SEQUENCE: 249

Lys Cys Asp Ile Cys Thr Asp Glu Tyr
1 5

<210> SEQ ID NO 250
<211> LENGTH: 9
<212> TYPE: PRT
<213> ORGANISM: Homo sapiens

<400> SEQUENCE: 250

Tyr Met Asp Gly Thr Met Ser Gln Val
1 5

<210> SEQ ID NO 251
<211> LENGTH: 9
<212> TYPE: PRT
<213> ORGANISM: Homo sapiens

<400> SEQUENCE: 251

Met Leu Leu Ala Tyr Leu Tyr Gln Leu 1 5

<210> SEQ ID NO 252
<211> LENGTH: 9
<212> TYPE: PRT
<213> ORGANISM: Homo sapiens

<400> SEQUENCE: 252

Ala Phe Leu Pro Trp His Arg Leu Phe
1 5

<210> SEQ ID NO 253
<211> LENGTH: 10
<212> TYPE: PRT
<213> ORGANISM: Homo sapiens

<400> SEQUENCE: 253

Ala Phe Leu Pro Trp His Arg Leu Phe Leu
1 5 10

<210> SEQ ID NO 254
<211> LENGTH: 9
<212> TYPE: PRT
<213> ORGANISM: Homo sapiens

<400> SEQUENCE: 254

Ser Glu Ile Trp Arg Asp Ile Asp Phe
1 5

<210> SEQ ID NO 255
<211> LENGTH: 9
<212> TYPE: PRT
<213> ORGANISM: Homo sapiens

<400> SEQUENCE: 255

Tyr Leu Glu Pro Gly Pro Val Thr Ala
1 5

<210> SEQ ID NO 256
<211> LENGTH: 9
<212> TYPE: PRT
<213> ORGANISM: Homo sapiens

<400> SEQUENCE: 256

Lys Thr Trp Gly Gln Tyr Trp Gln Val
1 5

<210> SEQ ID NO 257
<211> LENGTH: 9
<212> TYPE: PRT
<213> ORGANISM: Homo sapiens

<400> SEQUENCE: 257

Ile Thr Asp Gln Val Pro Phe Ser Val
1 5

<210> SEQ ID NO 258
<211> LENGTH: 10
<212> TYPE: PRT
<213> ORGANISM: Homo sapiens

<400> SEQUENCE: 258

Val Leu Tyr Arg Tyr Gly Ser Phe Ser Val
1 5 10

<210> SEQ ID NO 259
<211> LENGTH: 10
<212> TYPE: PRT
<213> ORGANISM: Homo sapiens

<400> SEQUENCE: 259

Leu Leu Asp Gly Thr Ala Thr Leu Arg Leu
1 5 10

<210> SEQ ID NO 260
<211> LENGTH: 9
<212> TYPE: PRT
<213> ORGANISM: Homo sapiens

<400> SEQUENCE: 260

Ala Leu Leu Ala Val Gly Ala Thr Lys
1 5

<210> SEQ ID NO 261
<211> LENGTH: 9
<212> TYPE: PRT
<213> ORGANISM: Homo sapiens

<400> SEQUENCE: 261

Met Leu Gly Thr His Thr Met Glu Val
1 5

<210> SEQ ID NO 262
<211> LENGTH: 9
<212> TYPE: PRT
<213> ORGANISM: Homo sapiens

<400> SEQUENCE: 262

Leu Ile Tyr Arg Arg Arg Leu Met Lys
1 5

<210> SEQ ID NO 263
<211> LENGTH: 9
<212> TYPE: PRT
<213> ORGANISM: Homo sapiens

<400> SEQUENCE: 263

Ala Leu Asn Phe Pro Gly Ser Gln Lys
1 5

<210> SEQ ID NO 264
<211> LENGTH: 9
<212> TYPE: PRT
<213> ORGANISM: Homo sapiens

<400> SEQUENCE: 264

Ala Ala Gly Ile Gly Ile Leu Thr Val
1 5

<210> SEQ ID NO 265
<211> LENGTH: 9
<212> TYPE: PRT
<213> ORGANISM: Homo sapiens

<400> SEQUENCE: 265

Ile Leu Thr Val Ile Leu Gly Val Leu
1 5

<210> SEQ ID NO 266
<211> LENGTH: 9
<212> TYPE: PRT

<213> ORGANISM: Homo sapiens

<400> SEQUENCE: 266

Met Ser Leu Gln Arg Gln Phe Leu Arg
1 5

<210> SEQ ID NO 267
<211> LENGTH: 9
<212> TYPE: PRT
<213> ORGANISM: Homo sapiens

<400> SEQUENCE: 267

Ser Val Tyr Asp Phe Phe Val Trp Leu
1 5

<210> SEQ ID NO 268
<211> LENGTH: 9
<212> TYPE: PRT
<213> ORGANISM: Homo sapiens

<400> SEQUENCE: 268

Leu Leu Gly Pro Gly Arg Pro Tyr Arg
1 5

<210> SEQ ID NO 269
<211> LENGTH: 9
<212> TYPE: PRT
<213> ORGANISM: Homo sapiens

<400> SEQUENCE: 269

Tyr Leu Ser Gly Ala Asn Leu Asn Leu
1 5

<210> SEQ ID NO 270
<211> LENGTH: 9
<212> TYPE: PRT
<213> ORGANISM: Homo sapiens

<400> SEQUENCE: 270

Lys Ile Phe Gly Ser Leu Ala Phe Leu
1 5

<210> SEQ ID NO 271
<211> LENGTH: 10
<212> TYPE: PRT
<213> ORGANISM: Homo sapiens

<400> SEQUENCE: 271

Val Met Ala Gly Val Gly Ser Pro Tyr Val
1 5 10

<210> SEQ ID NO 272
<211> LENGTH: 9
<212> TYPE: PRT
<213> ORGANISM: Homo sapiens

<400> SEQUENCE: 272

Ile Ile Ser Ala Val Val Gly Ile Leu
1 5

<210> SEQ ID NO 273
<211> LENGTH: 9
<212> TYPE: PRT
<213> ORGANISM: Homo sapiens

<400> SEQUENCE: 273

Leu Leu His Glu Thr Asp Ser Ala Val
1 5

<210> SEQ ID NO 274
<211> LENGTH: 9
<212> TYPE: PRT
<213> ORGANISM: Homo sapiens

<400> SEQUENCE: 274

Ala Leu Phe Asp Ile Glu Ser Lys Val
1 5

<210> SEQ ID NO 275
<211> LENGTH: 9
<212> TYPE: PRT
<213> ORGANISM: Homo sapiens

<400> SEQUENCE: 275

Glu Ala Asp Pro Thr Gly His Ser Tyr
1 5

<210> SEQ ID NO 276
<211> LENGTH: 9
<212> TYPE: PRT
<213> ORGANISM: Homo sapiens

<400> SEQUENCE: 276

Ser Leu Phe Arg Ala Val Ile Thr Lys
1 5

<210> SEQ ID NO 277
<211> LENGTH: 9
<212> TYPE: PRT
<213> ORGANISM: Homo sapiens

<400> SEQUENCE: 277

Ser Ala Tyr Gly Glu Pro Arg Lys Leu
1 5

<210> SEQ ID NO 278
<211> LENGTH: 9
<212> TYPE: PRT
<213> ORGANISM: Homo sapiens

<400> SEQUENCE: 278

Lys Met Val Glu Leu Val His Phe Leu
1 5

<210> SEQ ID NO 279
<211> LENGTH: 10
<212> TYPE: PRT
<213> ORGANISM: Homo sapiens

<400> SEQUENCE: 279

Tyr Leu Gln Leu Val Phe Gly Ile Glu Val
1 5 10

<210> SEQ ID NO 280
<211> LENGTH: 9
<212> TYPE: PRT
<213> ORGANISM: Homo sapiens

<400> SEQUENCE: 280

Glu Val Asp Pro Ile Gly His Leu Tyr
1 5

<210> SEQ ID NO 281
<211> LENGTH: 9
<212> TYPE: PRT
<213> ORGANISM: Homo sapiens

<400> SEQUENCE: 281

Phe Leu Trp Gly Pro Arg Ala Leu Val
1 5

<210> SEQ ID NO 282
<211> LENGTH: 10
<212> TYPE: PRT
<213> ORGANISM: Homo sapiens

<400> SEQUENCE: 282

Met Glu Val Asp Pro Ile Gly His Leu Tyr
1 5 10

<210> SEQ ID NO 283
<211> LENGTH: 9
<212> TYPE: PRT
<213> ORGANISM: Homo sapiens

<400> SEQUENCE: 283

Ala Ala Arg Ala Val Phe Leu Ala Leu
1 5

<210> SEQ ID NO 284
<211> LENGTH: 8
<212> TYPE: PRT
<213> ORGANISM: Homo sapiens

<400> SEQUENCE: 284

Tyr Arg Pro Arg Pro Arg Arg Tyr
1 5

<210> SEQ ID NO 285
<211> LENGTH: 9
<212> TYPE: PRT
<213> ORGANISM: Homo sapiens

<400> SEQUENCE: 285

Val Leu Pro Asp Val Phe Ile Arg Cys
1 5

<210> SEQ ID NO 286
<211> LENGTH: 9
<212> TYPE: PRT
<213> ORGANISM: Homo sapiens

<400> SEQUENCE: 286

Gln Leu Ser Leu Leu Met Trp Ile Thr
1 5

<210> SEQ ID NO 287
<211> LENGTH: 9
<212> TYPE: PRT
<213> ORGANISM: Homo sapiens

<400> SEQUENCE: 287

Ser Leu Leu Met Trp Ile Thr Gln Cys
1 5

<210> SEQ ID NO 288

-continued

<211> LENGTH: 10
<212> TYPE: PRT
<213> ORGANISM: Homo sapiens

<400> SEQUENCE: 288

Ala Ser Gly Pro Gly Gly Gly Ala Pro Arg
1 5 10

<210> SEQ ID NO 289
<211> LENGTH: 10
<212> TYPE: PRT
<213> ORGANISM: Homo sapiens

<400> SEQUENCE: 289

Gln Asp Leu Thr Met Lys Tyr Gln Ile Phe
1 5 10

<210> SEQ ID NO 290
<211> LENGTH: 9
<212> TYPE: PRT
<213> ORGANISM: Homo sapiens

<400> SEQUENCE: 290

Ala Tyr Gly Leu Asp Phe Tyr Ile Leu
1 5

<210> SEQ ID NO 291
<211> LENGTH: 10
<212> TYPE: PRT
<213> ORGANISM: Homo sapiens

<400> SEQUENCE: 291

Glu Ala Tyr Gly Leu Asp Phe Tyr Ile Leu
1 5 10

<210> SEQ ID NO 292
<211> LENGTH: 9
<212> TYPE: PRT
<213> ORGANISM: Homo sapiens

<400> SEQUENCE: 292

Ser Tyr Leu Asp Ser Gly Ile His Phe
1 5

<210> SEQ ID NO 293
<211> LENGTH: 9
<212> TYPE: PRT
<213> ORGANISM: Homo sapiens

<400> SEQUENCE: 293

Glu Thr Val Ser Glu Gln Ser Asn Val
1 5

<210> SEQ ID NO 294
<211> LENGTH: 9
<212> TYPE: PRT
<213> ORGANISM: Homo sapiens

<400> SEQUENCE: 294

Phe Pro Ser Asp Ser Trp Cys Tyr Phe
1 5

<210> SEQ ID NO 295
<211> LENGTH: 9
<212> TYPE: PRT
<213> ORGANISM: Homo sapiens -continued

```
<400> SEQUENCE: 295

Glu Glu Lys Leu Ile Val Val Leu Phe
1               5


<210> SEQ ID NO 296
<211> LENGTH: 13
<212> TYPE: PRT
<213> ORGANISM: Artificial sequence
<220> FEATURE:
<223> OTHER INFORMATION: Synthetic construct; pan-DR epitope PADRE

<400> SEQUENCE: 296

Ala Lys Phe Val Ala Ala Trp Thr Leu Lys Ala Ala Ala
1               5                   10
```

SELF-ASSEMBLING PEPTIDE NANOPARTICLES USEFUL AS VACCINES

This application is a U.S. national stage of International Application No. PCT/EP2009/050996 filed Jan. 29, 2009.

FIELD OF THE INVENTION

The present invention relates to self-assembling peptide nanoparticles incorporating B-cell epitopes and/or T-cell epitopes. Furthermore, the invention relates to the use of such nanoparticles for vaccination.

BACKGROUND OF THE INVENTION

The adaptive immune system has two different responses, the humoral immune response and the cellular immune response. The first is characterized by an antibody response in which these antibodies bind to surface epitopes of pathogens while the latter is characterized by cytotoxic T-lymphozytes (CTLs) that kill already infected cells. Both immune responses are further stimulated by T-helper cells that activate either the B-cells that are producing specific pathogen binding antibodies or T-cells that are directed against infected cells.

The specificity of the interaction between the antibodies produced by B-cells and the pathogen is determined by surface structures of the pathogen, so called B-cell epitopes, while the specificity of the interaction of CTLs with the infected target cell is by means of T-cell epitopes presented on surface molecules of the target cell, the so-called major histocompatibility complex class I molecules (MHC I). This type of T-cell epitopes (CTL-epitopes) are fragments of the proteins from the pathogen that are produced by the infected cell. Finally, the specificity of the interaction of the T-helper cells with the respective B-cell or CTL is determined by binding of receptor molecules of the T-helper cells to the other type of T-cell epitopes (HTL-epitopes) presented by the MHC class II molecules (MHC II) on the B-cells or CTL-cells.

Binding of the antibodies to the B-cell epitopes requires the B-cell epitope to assume a particular three-dimensional structure, the same structure that this B-cell epitope has in its native environment, i.e. when it is on the surface of the pathogen. The B-cell epitope may be composed of more than one peptide chain and is organized in a three dimensional structure by the scaffold of the protein.

The T-cell epitopes, however, do not require a particular three-dimensional structure, rather they are bound by the respective MHC I or MHC II molecule in a very specific manner. CTL epitopes are trimmed to a size of 9 amino acids in length for optimal presentation by the MHC I molecules, while HTL epitopes make a similar interaction with the MHC II molecules but may be longer than just 9 amino acids. Important in the context of this invention is, that the binding of the epitopes to the MHC molecules follows very particular rules, i.e. only peptides with specific features will be able to bind to the respective MHC molecule and hence be useful as epitopes. These features have been thoroughly investigated and from the wealth of epitopes known, prediction programs have been developed that are able to predict with high accuracy epitopes that are able to bind to the MHC molecules. Peptide strings composed of several such T-cell epitopes in a linear peptide chain are now being engineered as vaccine candidates.

In general an efficient vaccine should induce a strong humoral as well as a strong cellular immune response. It has been shown that by repetitive antigen display of B-cell epitopes a strong humoral immune response can be achieved. Virus-like particles (VLPs) can be used as an efficient tool to present B-cell epitopes in a regular, repetitive and rigid manner, and hence VLPs are now widely used for vaccine design. Another approach for repetitive antigen display has been described in Patent EP 1 594 469 B1. In this patent self-assembling peptide nanoparticles (SAPN) composed of trimeric and pentameric protein oligomerization domains have been engineered that repetitively display B-cell epitopes on their surface. The B-cell epitopes were attached at the end of the oligomerization domains in order to guarantee that the B-cell epitopes are presented at the surface of the nanoparticles in multiple copies. One of the most frequently encountered protein oligomerization motif is the coiled-coil structural motif and this motif can efficiently be used in the design of these SAPN.

SUMMARY OF THE INVENTION

The invention relates to self-assembling peptide nanoparticles (SAPN) incorporating T-cell epitopes and/or B-cell epitopes. In particular, nanoparticles of the invention consist of aggregates of a continuous peptidic chain comprising two oligomerization domains connected by a linker segment wherein one or both oligomerization domains is a coiled-coil that incorporates T-cell epitopes and/or B-cell epitopes within its peptide sequence.

The invention further relates to a method of vaccinating humans or non-human animals using such self-assembling peptide nanoparticles incorporating T-cell epitopes and/or B-cell epitopes.

DETAILED DESCRIPTION OF THE INVENTION

Monomeric Building Blocks

Figure 1:
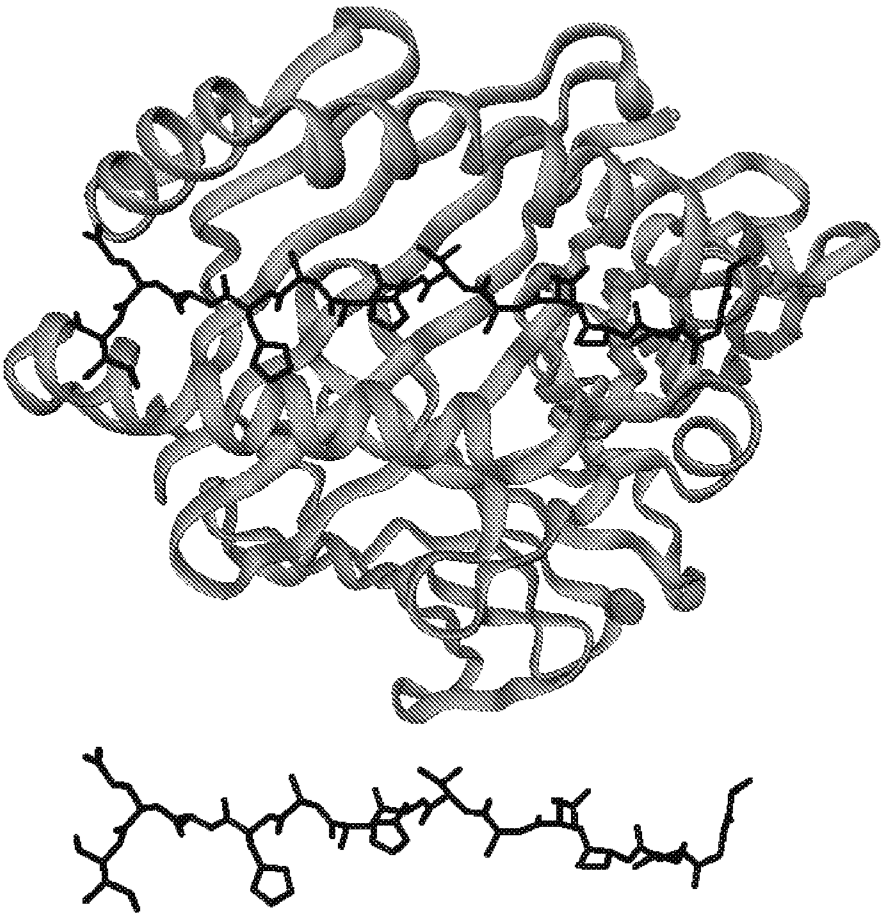
FIG. 1: The structure of mouse MHC II molecule I-Ad covalently linked to an ovalbumin peptide (OVA323-339), which is a HTL epitope for I-Ad. The MHC II protein is shown from the top in a C-alpha trace in gray. The two helices forming the walls of the epitope binding sites are flanking the bound peptide. The peptide is shown in an all-atom ball-and-stick model in black. The peptide HTL epitope in its bound form is in extended conformation as can be seen more clearly by the structure of the peptide alone at the bottom of the figure.

Self-assembling peptide nanoparticles (SAPN) are formed from a multitude of monomeric building blocks of formula (I) consisting of a continuous chain comprising a peptidic oligomerization domain D1, a linker segment L and a peptidic oligomerization domain D2

D1-L-D2 (I), wherein D1 is a synthetic or natural peptide having a tendency to form oligomers $(D1)_m$ of m subunits D1, D2 is a synthetic or natural peptide having a tendency to form oligomers $(D2)_n$ of n subunits D2, m and n each is a figure between 2 and 10, with the proviso that m is not equal n and not a multiple of n, and n is not a multiple of m, L is a bond or a short linker chain selected from optionally substituted carbon atoms, optionally substituted nitrogen atoms, oxygen atoms, sulfur atoms, and combinations thereof; either D1 or D2 or both D1 and D2 is a coiled-coil that incorporates one or more T-cell epitopes and/or a B-cell epitope within the oligomerization domain, and wherein D1, D2 and L are optionally further substituted.

A peptide (or polypeptide) is a chain or sequence of amino acids covalently linked by amide bonds. The peptide may be natural, modified natural, partially synthetic or fully synthetic. Modified natural, partially synthetic or fully synthetic is understood as meaning not occurring in nature. The term amino acid embraces both naturally occurring amino acids selected from the 20 essential natural α-L-amino acids, synthetic amino acids, such as α-D-amino acids, 6-aminohexanoic acid, norleucine, homocysteine, or the like, as well as naturally occurring amino acids which have been modified in some way to alter certain properties such as charge, such as phoshoserine or phosphotyrosine, or the like. In derivatives of amino acids the amino group forming the amide bond is alkylated, or a side chain amino, hydroxy or thio functions is alkylated or acylated, or a side chain carboxy function is amidated or esterified.

A short linker chain L is selected from optionally substituted carbon atoms, optionally substituted nitrogen atoms, oxygen atoms, sulfur atoms, and combinations thereof, with preferably 1 to 60 atoms, in particular 1 to 20 atoms in the chain. Such a short linker chain is, e.g. a polyethylenoxy chain, a sugar chain or, preferably, a peptide chain, e.g. a peptide chain consisting of 1 to 20 amino acids, in particular 1 to 6 amino acids.

m and n each is a figure between 2 and 10, with the proviso that m is not equal n and not a multiple of n, and n is not a multiple of m. Preferred combinations of n and m are combinations wherein m is 2 and n is 5, or m is 3 and n is 4 or 5, or m is 4 and n is 5. Likewise preferred combinations of n and m are combinations wherein m is 5 and n is 2, or m is 4 or 5 and n is 3, or m is 5 and n is 4. Most preferred are combinations wherein m or n is 5.

A coiled-coil is a peptide sequence with a contiguous pattern of mainly hydrophobic residues spaced 3 and 4 residues apart, which assembles to form a multimeric bundle of helices, as will explained in more detail hereinbelow.

"A coiled-coil that incorporates T-cell and/or B-cell epitopes" means that the corresponding epitope is comprised within an oligomerization domain such that the amino acid sequences at the N-terminal and the C-terminal ends of the epitope force the epitope to adapt a conformation which is still a coiled-coil in line with the oligomerization properties of the oligomerization domain comprising the epitope. In particular, "incorporated" excludes a case wherein the epitope is attached at either end of the coiled-coil oligomerization domain.

In the context of this document the term T-cell epitopes shall be used to refer to both CTL and HTL epitopes.

T-cell epitopes bind to the MHC molecules in extended conformation (FIG. 1). Therefore, incorporating T-cell epitopes into an α-helical coiled-coil (compare FIG. 3A and FIG. 1) is not a trivial task of protein engineering. In this invention it is demonstrated how these peptide sequences that have an extended conformation when bound to the respective MHC molecule can nevertheless be incorporated into an α-helical coiled-coil oligomerization domain.

Optional substituents of D1, D2 and L are e.g. B-cell epitopes, targeting entities, or substituents reinforcing the adjuvant properties of the nanoparticle, such as an immunostimulatory nucleic acid, preferably an oligodeoxynucleotide containing deoxyinosine, an oligodeoxynucleotide containing deoxyuridine, an oligodeoxynucleotide containing a CG motif, or an inosine and cytidine containing nucleic acid molecule. Other substituents reinforcing the adjuvant properties of the nanoparticle are antimicrobial peptides, such as cationic peptides, which are a class of immunostimulatory, positively charged molecules that are able to facilitate and/or improve adaptive immune responses. An example of such a peptide with immunopotentiating properties is the positively charged artificial antimicrobial peptide KLKLLLLLKLK (SEQ ID NO: 63) which induces potent protein-specific type-2 driven adaptive immunity after prime-boost immunizations. A particular targeting entity considered as substituent is an ER-targeting signal, i.e. a signal peptide that induces the transport of a protein or peptide to the endoplasmic reticulum (ER). Other optional substituents are, for example, an acyl group, e.g. acetyl, bound to a free amino group, in particular to the N-terminal amino acid, or amino bound to the free carboxy group of the C-terminal amino acid to give a carboxamide function.

Optional substituents, e.g. those optional substituents described hereinabove, are preferably connected to suitable amino acids close to the free end of the oligomerization domain D1 and/or D2. On self-assembly of the peptide nanoparticle, such substituents will then be presented at the surface of the SAPN.

In a most preferred embodiment the substituent is another peptide sequence S1 and/or S2 representing a simple extension of the peptide chain D1-L-D2 at either end or at both ends to generate a combined single peptide sequence of any of the forms S1-D1-L-D2, D1-L-D2-S2, or S1-D1-L-D2-S2, wherein S1 and S2 are peptidic substituents as defined hereinbefore and hereinafter. The substituents S1 and/or S2 are said to extend the core sequence D1-L-D2 of the SAPN. Any such peptide sequence S1-D1-L-D2, D1-L-D2-S2, or S1-D1-L-D2-S2 may be expressed in a recombinant protein expression system as one single molecule.

A preferred substituent S1 and/or S2 is a B-cell epitope. Other B-cell epitopes considered are hapten molecules such as a carbohydrate or nicotine, which are likewise attached to the end of the oligomerization domains D1 and/or D2, and hence will be displayed at the surface of the SAPN.

Obviously it is also possible to attach more than one substituent to the oligomerization domains D1 and/or D2. For example, considering the peptide sequence S1-D1-L-D2-S2, another substituent may be covalently attached to it, preferably at a location distant from the linker segment L, either close to the ends of D1 and/or D2, or anywhere in the substituents S1 and/or S2.

It is also possible to attach a substituent to the linker segment L. In such case, upon refolding of the SAPN, the substituent will be located in the inner cavity of the SAPN.

A tendency to form oligomers means that such peptides can form oligomers depending on the conditions, e.g. under denaturing conditions they are monomers, while under physiological conditions they may form, for example, trimers. Under predefined conditions they adopt one single oligomerization state, which is needed for nanoparticle formation. However, their oligomerization state may be changed upon changing conditions, e.g. from dimers to trimers upon increasing salt concentration (Burkhard P. et al., Protein Science 2000, 9:2294-2301) or from pentamers to monomers upon decreasing pH.

A building block architecture according to formula (I) is clearly distinct from viral capsid proteins. Viral capsids are composed of either one single protein, which forms oligomers of 60 or a multiple thereof, as e.g. the hepatitis virus B particles (EP 1 262 555, EP 0 201 416), or of more than one protein, which co-assemble to form the viral capsid structure, which can adopt also other geometries apart from icosahedra, depending on the type of virus (Fender P. et al., Nature Biotechnology 1997, 15:52-56). Self-assembling peptide nanoparticles (SAPN) of the present invention are also clearly distinct from virus-like particles, as they (a) are constructed from other than viral capsid proteins and (b) that the cavity in the middle of the nanoparticle is too small to accommodate the DNA/RNA of a whole viral genome.

Peptidic oligomerization domains are well-known (Burkhard P. et al., Trends Cell Biol 2001, 11:82-88). The most simple oligomerization domain is probably the coiled-coil folding motif. This oligomerization motif has been shown to exist as a dimer, trimer, tetramer and pentamer. Some examples are the GCN4 leucine zipper, fibritin, tetrabrachion and COMP, representing dimeric, trimeric, tetrameric and pentameric coiled coils, respectively.

One or both oligomerization domains D1 and D2, independently of each other, are coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, Ile, Leu, Met, Tyr, Phe and Trp. Mainly hydrophobic means that at least 50% of the residues must be selected from the mentioned hydrophobic amino acids.

For example, in a preferred monomeric building block of formula (I), D1 and/or D2 is a peptide of any of the formulae $$[aa(a)\text{-}aa(b)\text{-}aa(c)\text{-}aa(d)\text{-}aa(e)\text{-}aa(f)\text{-}aa(g)]_X \quad \text{(IIa)},$$

$$[aa(b)\text{-}aa(c)\text{-}aa(d)\text{-}aa(e)\text{-}aa(f)\text{-}aa(g)\text{-}aa(a)]_X \quad \text{(IIb)},$$

$$[aa(c)\text{-}aa(d)\text{-}aa(e)\text{-}aa(f)\text{-}aa(g)\text{-}aa(a)\text{-}aa(b)]_X \quad \text{(IIc)},$$

$$[aa(d)\text{-}aa(e)\text{-}aa(f)\text{-}aa(g)\text{-}aa(a)\text{-}aa(b)\text{-}aa(c)]_X \quad \text{(IId)},$$

$$[aa(e)\text{-}aa(f)\text{-}aa(g)\text{-}aa(a)\text{-}aa(b)\text{-}aa(c)\text{-}aa(d)]_X \quad \text{(IIe)},$$

$$[aa(f)\text{-}aa(g)\text{-}aa(a)\text{-}aa(b)\text{-}aa(c)\text{-}aa(d)\text{-}aa(e)]_X \quad \text{(IIf)},$$

$$[aa(g)\text{-}aa(a)\text{-}aa(b)\text{-}aa(c)\text{-}aa(d)\text{-}aa(e)\text{-}aa(f)]_X \quad \text{(IIg)},$$

wherein aa means an amino acid or a derivative thereof, aa(a), aa(b), aa(c), aa(d), aa(e), aa(f), and aa(g) are the same or different amino acids or derivatives thereof, preferably aa(a) and aa(d) are the same or different hydrophobic amino acids or derivatives thereof; and X is a figure between 2 and 20, preferably 3, 4, 5 or 6.

Hydrophobic amino acids are Val, Ile, Leu, Met, Tyr, Phe and Trp.

A heptad is a heptapeptide of the formula aa(a)-aa(b)-aa (c)-aa(d)-aa(e)-aa(f)-aa(g) (IIa) or any of its permutations of formulae (IIb) to (IIg).

Preferred are monomeric building blocks of formula (I) wherein one or both peptidic oligomerization domains D1 or D2 are (1) a peptide of any of the formulae (IIa) to (IIg) wherein X is 3, and aa(a) and aa(d) are selected from the 20 natural α-L-amino acids such that the sum of scores from Table 1 for these 6 amino acids is at least 14, and such peptides comprising up to 17 further heptads; or (2) a peptide of any of the formulae (IIa) to (IIg) wherein X is 3, and aa(a) and aa(d) are selected from the 20 natural α-L-amino acids such that the sum of scores from Table 1 for these 6 amino acids is at least 12, with the proviso that one amino acid aa(a) is a charged amino acid able to form an inter-helical salt bridge to an amino acid aa(d) or aa(g) of a neighboring heptad, or that one amino acid aa(d) is a charged amino acid able to form an inter-helical salt bridge to an amino acid aa(a) or aa(e) of a neighboring heptad, and such peptides comprising up to two further heptads. A charged amino acid able to form an inter-helical salt bridge to an amino acid of a neighboring heptad is, for example, Asp or Glu if the other amino acid is Lys, Arg or His, or vice versa.

TABLE 1

Scores of amino acid for determination of preference

| Amino acid | Position aa(a) | Position aa(d) |
|---|---|---|
| L (Leu) | 3.5 | 3.8 |
| M (Met) | 3.4 | 3.2 |
| I (Ile) | 3.9 | 3.0 |

TABLE 1-continued

| Scores of amino acid for determination of preference | | |
|---|---|---|
| Amino acid | Position aa(a) | Position aa(d) |
| Y (Tyr) | 2.1 | 1.4 |
| F (Phe) | 3.0 | 1.2 |
| V (Val) | 4.1 | 1.1 |
| Q (Gln) | −0.1 | 0.5 |
| A (Ala) | 0.0 | 0.0 |
| W (Trp) | 0.8 | −0.1 |
| N (Asn) | 0.9 | −0.6 |
| H (His) | −1.2 | −0.8 |
| T (Thr) | 0.2 | −1.2 |
| K (Lys) | −0.4 | −1.8 |
| S (Ser) | −1.3 | −1.8 |
| D (Asp) | −2.5 | −1.8 |
| E (Glu) | −2.0 | −2.7 |
| R (Arg) | −0.8 | −2.9 |
| G (Gly) | −2.5 | −3.6 |
| P (Pro) | −3.0 | −3.0 |
| C (Cys) | 0.2 | −1.2 |

Also preferred are monomeric building blocks of formula (I) wherein one or both peptidic oligomerization domains D1 or D2 are selected from the following preferred peptides:

(11) Peptide of any of the formulae (IIa) to (IIg) wherein aa(a) is selected from Val, Ile, Leu and Met, and a derivative thereof, and aa(d) is selected from Leu, Met and Ile, and a derivative thereof.

(12) Peptide of any of the formulae (IIa) to (IIg) wherein one aa(a) is Asn and the other aa(a) are selected from Asn, Ile and Leu, and aa(d) is Leu. Such a peptide is usually a dimerization domain (m or n=2).

(13) Peptide of any of the formulae (IIa) to (IIg) wherein aa(a) and aa(d) are both Leu or both Ile. Such a peptide is usually a trimerization domain (m or n=3).

(14) Peptide of any of the formulae (IIa) to (IIg) wherein aa(a) and aa(d) are both Trp. Such a peptide is usually a pentamerization domain (m or n=5).

(15) Peptide of any of the formulae (IIa) to (IIg) wherein aa(a) and aa(d) are both Phe. Such a peptide is usually a pentamerization or tetramerization domain (m or n=4 or 5).

(16) Peptide of any of the formulae (IIa) to (IIg) wherein aa(a) and aa(d) are both either Trp or Phe. Such a peptide is usually a pentamerization domain (m or n=5).

(17) Peptide of any of the formulae (IIa) to (IIg) wherein aa(a) is either Leu or Ile, and one aa(d) is Gln and the other aa(d) are selected from Gln, Leu and Met. Such a peptide has the potential to be a pentamerization domain (m or n=5).

Other preferred peptides are peptides (1), (2), (11), (12), (13), (14), (15), (16) and (17) as defined hereinbefore, and wherein further

(21) at least one aa(g) is selected from Asp and Glu and aa(e) in a following heptad is Lys, Arg or His; and/or

(22) at least one aa(g) is selected from Lys, Arg and His, and aa(e) in a following heptad is Asp or Glu, and/or

(23) at least one aa(a to g) is selected from Lys, Arg and His, and an aa(a to g) 3 or 4 amino acids apart in the sequence is Asp or Glu. Such pairs of amino acids aa(a to g) are, for example aa(b) and aa(e) or aa(f).

Coiled-coil prediction programs such as COILS (Gruber M. et al., J. Struct. Biol. 2006, 155(2):140-5) or MULTICOIL can predict coiled-coil forming peptide sequences. Therefore, in a preferred monomeric building block of formula (I), D1 and/or D2 is a peptide that contains at least a sequence two heptad-repeats long that is predicted by the coiled-coil prediction program COILS to form a coiled-coil with higher probability than 0.9 for all its amino acids with at least one of the window sizes of 14, 21, or 28.

In a more preferred monomeric building block of formula (I), D1 and/or D2 is a peptide that contains at least one sequence three heptad-repeats long that is predicted by the coiled-coil prediction program COILS to form a coiled-coil with higher probability than 0.9 for all its amino acids with at least one of the window sizes of 14, 21, or 28.

In another more preferred monomeric building block of formula (I), D1 and/or D2 is a peptide that contains at least two separate sequences two heptad-repeats long that are predicted by the coiled-coil prediction program COILS to form a coiled-coil with higher probability than 0.9 for all its amino acids with at least one of the window sizes of 14, 21, or 28.

In another preferred embodiment, one oligomerization domain D1 or D2 is the pentamerization domain (m or n=5) of COMP (Malashkevich V. N. et al., Science 1996, 274:761-765) or a derivative thereof. This pentamerization domain has the sequence LAPQMLRELQETNAALQDVRELL-RQQVKQITFLKNTVMECDACG (SEQ ID NO:1). Small modifications of this domain are also envisaged. Such modifications may be e.g. the substitution of amino acids at the outside of the pentamer at positions aa(b), aa(c) or aa(f), preferably in position aa(f), by Cys for the purpose of the formation of a disulfide bridge between adjacent domains. Other modifications of surface amino acids of this domain may include substitutions of amino acids for optimizing the interactions at the interface between adjacent oligomerization domains such as hydrophobic, hydrophilic or ionic interactions or covalent bonds like disulfide bridges. Also shorter constructs of this domain, e.g. lacking the C-terminal CDACG motif in which the cysteins form intermolecular disulfide bridges at the C-terminus of this pentamerization domain are also envisaged. Modification of amino acids affecting the oligomerization state of this domain are also envisaged, resulting e.g. in a transition from pentamer to tetramer. Yet other modifications of surface amino acids of this domain may include substitutions of amino acids (e.g. by cysteine or lysine) for the generation of attachment sites for functional groups.

In another preferred embodiment, one oligomerization domain D1 or D2 is the pentamerization domain (m or n=5) of the tryptophan zipper (Liu J et al., Proc Natl Acad Sci USA 2004; 101(46):16156-61) or a derivative thereof. This pentamerization domain has the sequence SSNAKWDQWSSD-WQTWNAKWDQWSNDWNAWRSDWQAWKDD WAR-WNQRWDNWAT (SEQ ID NO:2). Small modifications of this domain are also envisaged. Such modifications may be, e.g., the substitution of amino acids at the outside of the pentamer at positions aa(b), aa(c) or aa(f), preferably in position aa(f), by Cys for the purpose of the formation of a disulfide bridge between adjacent domains. Other modifications of surface amino acids of this domain may include substitutions of amino acids for optimizing the interactions at the interface between adjacent oligomerization domains such as hydrophobic, hydrophilic or ionic interactions, or covalent bonds such as disulfide bridges. Also shorter constructs of this domain are envisaged. Modification of amino acids affecting the oligomerization state of this domain are also envisaged, resulting, for example, in a transition from pentamerization domain to tetramerization domain exchanging core residues Trp by Phe. Other core residue mutations as in Example 10 are also considered, but at least 70% of the core positions aa(a) and aa(d) have to be either a Trp or another aromatic amino acid. Yet other modifications of surface amino acids of this domain may include substitutions of amino acids (e.g. by cysteine or lysine) for the generation of attachment sites for functional groups.

In another preferred embodiment, one oligomerization domain D1 or D2 is the tetramerization domain (m or n=4) of the coiled-coil domain of tetrabrachion (Stetefeld J. et al., Nature Structural Biology, 2000; 7(9):772-776) or a derivative thereof. This tetramerization domain has the sequence IINETADDIVYRLTVIIDDRYESLKNLITLRADRL MIINDNVSTILASG (SEQ ID NO:64). The sequences of coiled coils are characterized by a heptad repeat of seven residues with a 3,4-hydrophobic repeat. The next periodicity that allows residues to assume quasi-equivalent positions after a small number of turns is three turns or 11 residues. Based on the presence of 11-residue repeats, the C-terminus of the surface layer glycoprotein tetrabrachion from the hyperthermophilic archae-bacterium *Staphylothermus marinus* forms a right-handed coiled coil structure. It forms a tetrameric α-helical coiled coil stalk 70 nm long that is anchored to the cell membrane at its C-terminal end. This tetrameric coiled-coil contains a series of HTL epitopes (Example 9) and hence is ideally suited as core oligomer of the self-assembling peptide nanoparticle (SAPN).

In yet another preferred embodiment, one oligomerization domain D1 or D2 is the trimerization domain (foldon) of the bacteriophage T4 protein fibritin (Tao, Y. et al., Structure 1997, 5:789-798) or a derivative thereof. This trimerization domain (m or n=3) has the sequence GYIPEAPRDGQAYVRKDGEWVLLSTFL (SEQ ID NO:3). Small modifications of this domain are also envisaged. Such modifications may be the substitution of Asp 9 by Cys for the purpose of the formation of a disulfide bridge between adjacent domains. Other modifications of surface amino acids of this domain may include substitutions of residues for optimizing the interactions at the interface between adjacent oligomerization domains such as hydrophobic, hydrophilic or ionic interactions or covalent bonds like disulfide bridges. Yet other modifications of surface amino acids of this domain may include substitutions of amino acids (e.g. by cysteine or lysine) for the generation of attachment sites for functional groups.

Most preferred are the coiled-coil sequences and monomeric building blocks described in the examples.

Self-Assembling Peptide Nanoparticles: Even Units

Figure 2:
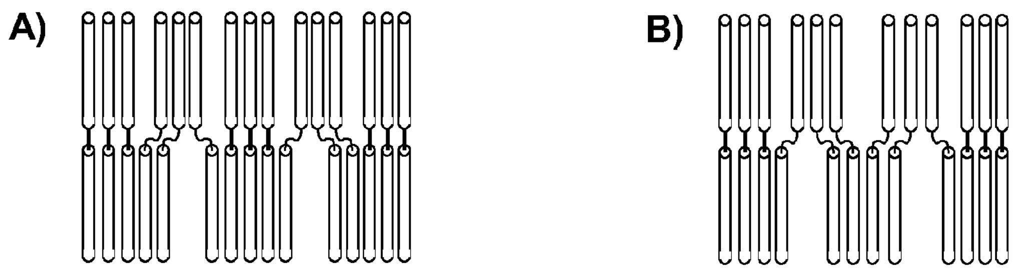
FIG. 2: Schematic drawing of "even units" for trimeric and pentameric oligomerization domains [left side, A)] and trimeric and tetrameric oligomerization domains [right side, B)], respectively. The number of monomers (building blocks) is defined by the least common multiple (LCM) of the oligomerization states of the two oligomerization domains D1 and D2 of the building blocks. In the even units the linker segments of all building blocks will be arranged as closely to each other as possible, i.e. as close to the center of the peptidic nanoparticle as possible and hence the even units will self-assemble to a spherical nanoparticle.

Self-assembling peptide nanoparticles (SAPN) are formed from monomeric building blocks of formula (I). If such building blocks assemble, they will form so-called "even units". The number of monomeric building blocks, which will assemble into such an even unit will be defined by the least common multiple (LCM). Hence, if for example the oligomerization domains of the monomeric building block form a trimer $(D1)_3$ (m=3) and a pentamer $(D2)_5$ (n=5), 15 monomers will form an even unit (FIG. 2A). If the linker segment L has the appropriate length, this even unit may assemble in the form of a spherical peptidic nanoparticle. Similarly, if the oligomerization domains D1 and D2 of the monomeric building block form a trimer $(D1)_3$ (m=3) and a tetramer $(D2)_4$ (n=4), the number of monomers needed to form an even unit will be 12 (FIG. 2B).

Since m and n cannot be equal or a multiple of each other, the least common multiple (LCM) is always larger than m and n.

Self-assembling peptide nanoparticles (SAPN) may be formed by the assembly of only one or more than one even units (Table 2). Such SAPN represent topologically closed structures.

TABLE 2

Possible combinations of oligomerization states

| ID No. | m | n | Polyhedron Type | LCM | No. of Even Units | No. of Building Blocks |
|---|---|---|---|---|---|---|
| 1 | 5 | 2 | dodecahedron/icosahedrons | 10 | 6 | 60 |
| 2 | 5 | 3 | dodecahedron/icosahedrons | 15 | 4 | 60 |
| 3 | 4 | 3 | cube/octahedron | 12 | 2 | 24 |
| 4 | 3 | 4 | cube/octahedron | 12 | 2 | 24 |
| 5 | 3 | 5 | dodecahedron/icosahedrons | 15 | 4 | 60 |
| 6 | 2 | 5 | dodecahedron/icosahedrons | 10 | 6 | 60 |
| 7 | 5 | 4 | Irregular | 20 | 1 | 20 |
| 8 | 4 | 5 | Irregular | 20 | 1 | 20 |

Regular Polyhedra

Figure 3:
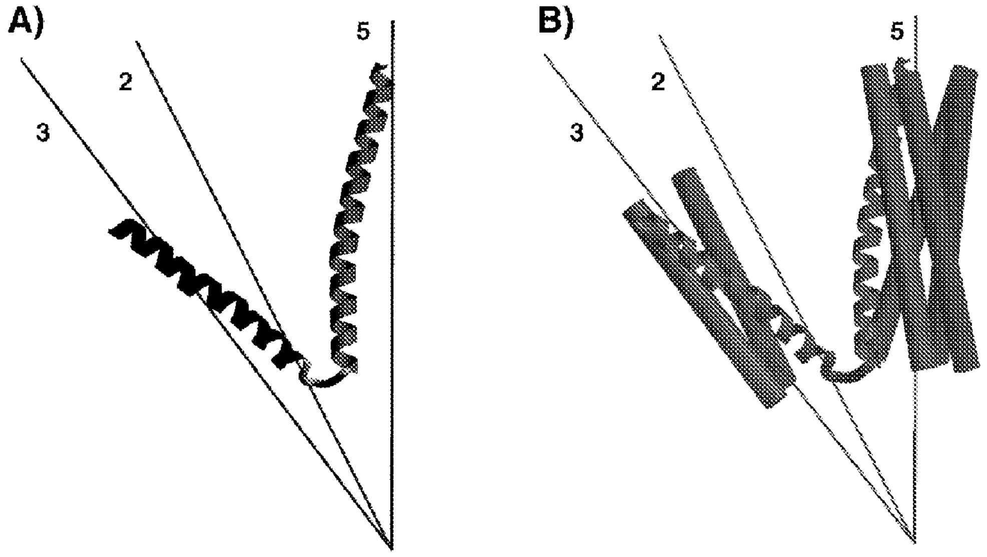
FIG. 3: Internal symmetry elements of the dodecahedron/icosahedron. The rotational symmetry axes (2-fold, 3-fold and 5-fold) are displayed as lines marked 2, 3 and 5. In A) a monomeric building block composed of oligomerization domain D1 (left, coiled-coil domain with three-fold symmetry), a linker segment L (bottom), and oligomerization domain D2 (right; coiled-coil domain with five-fold symmetry) is displayed such that the internal symmetry elements of the oligomerization domains D1 and D2 are superimposed onto the symmetry elements of the polyhedron. In B), the complete coiled-coil domains D1 and D2 are displayed. The additional symmetry objects generated by the 3-fold and the 5-fold rotational symmetry elements of the polyhedron are displayed as cylinders while the original molecule is displayed as a helix as in A).

There exist five regular polyhedra, the tetrahedron, the cube, the octahedron, the dodecahedron and the icosahedron. They have different internal rotational symmetry elements. The tetrahedron has a 2-fold and two 3-fold axes, the cube and the octahedron have a 2-fold, a 3-fold and a 4-fold rotational symmetry axis, and the dodecahedron and the icosahedron have a 2-fold, a 3-fold and a 5-fold rotational symmetry axis. In the cube the spatial orientation of these axes is exactly the same as in the octahedron, and also in the dodecahedron and the icosahedron the spatial orientation of these axes relative to each other is exactly the same. Hence, for the purpose of SAPN of the invention the cube and the octahedron, and similarly the dodecahedron and the icosahedron can be considered to be identical. The cube/octahedron is built up from 24 identical three-dimensional building blocks, while the dodecahedron/icosahedron is built up from 60 identical three-dimensional building blocks (Table 2). These building blocks are the asymmetric units (AUs) of the polyhedron. They are tri-pyramids and each of the pyramid edges corresponds to one of the rotational symmetry axes, hence these AUs will carry at their edges 2-fold, 3-fold, and 4-fold or 5-fold symmetry elements depending on the polyhedron type. If these symmetry elements are generated from peptidic oligomerization domains such AUs are constructed from monomeric building blocks as described above. It is sufficient to align the two oligomerization domains D1 and D2 along two of the symmetry axes of the AU (FIG. 3). If these two oligomerization domains form stable oligomers, the symmetry interface along the third symmetry axis will be generated automatically, and it may be stabilized by optimizing interactions along this interface, e.g. hydrophobic, hydrophilic or ionic interactions, or covalent bonds such as disulfide bridges.

Assembly to Self-Assembling Peptide Nanoparticles (SAPN) with Regular Polyhedral Symmetry To generate self-assembling peptide nanoparticles (SAPN) with a regular geometry (dodecahedron, cube), more than one even unit is needed. E.g. to form a dodecahedron from a monomer containing trimeric and pentameric oligomerization domains, 4 even units, each composed of 15 monomeric building blocks are needed, i.e. the peptidic nanoparticle with regular geometry will be composed of 60 monomeric building blocks. The combinations of the oligomerization states of the two oligomerization domains needed and the number of even units to form any of the regular polyhedra are listed in Table 2.

Whether the even units will further assemble to form regular polyhedra composed of more than one even unit depends on the geometrical alignment of the two oligomerizations domains D1 and D2 with respect to each other, especially on the angle between the rotational symmetry axes of the two oligomerization domains. This is governed by i) the interactions at the interface between neighboring domains in a nanoparticle, ii) the length of the linker segment L, iii) the shape of the individual oligomerization domains. This angle is larger in the even units compared to the arrangement in a regular polyhedron. Also this angle is not identical in monomeric building blocks as opposed to the regular polyhedron. If this angle is restricted to the smaller values of the regular polyhedron (by means of hydrophobic, hydrophilic or ionic interactions, or a covalent disulfide bridge) and the linker segment L is short enough, a given number of topologically closed even units each containing a defined number of monomeric building blocks will then further anneal to form a regular polyhedron (Table 2), or enclose more monomeric building blocks to from nanoparticles lacking strict internal symmetry of a polyhedron.

If the angle between the two oligomerization domains is sufficiently small (even smaller than in a regular polyhedron with icosahedral symmetry), then a large number (several hundred) peptide chains can assemble into a peptidic nanoparticle. This can be achieved by replacing the two cysteine residues that are located at the interface between the two helices as in the original design of Raman S. et al., Nanomedicine: Nanotechnology, Biology, and Medicine 2006, 2:95-102, and that are forming a disulfide bridge between the two helices, by the small residue alanine as in sequence SEQ ID NO:33. The angle between the two helices can get smaller and consequently more than 60 peptide chains can assemble into a SAPN. In such a design the SAPN have a molecular weight of about 4 MD, corresponding to about 330 peptide chains (Example 6).

T-Cell Epitopes and B-Cell Epitopes

Since the T-cell epitopes—as opposed to the B-cell epitopes—do not need to be displayed on the surface of a carrier to cause immunization, they can be incorporated into the core scaffold of the SAPN, i.e. the coiled-coil sequence of an oligomerization domain. In the present invention it is shown how the features of MHC binding of T-cell epitopes, which requires an extended conformation for MHC binding (FIG. 1), can be combined with the features of coiled-coil formation, which requires α-helical conformation for coiled-coil formation, such that these epitopes can be both, part of the coiled-coil scaffold of the SAPN as well as being able to bind to the respective MHC molecules. It should be noted that not all coiled-coil sequences will be able to bind to MHC molecules and not all T-cell epitopes can be incorporated into a coiled-coil structure. This invention provides the general rules, how to select appropriate T-cell epitopes and describes the way how to incorporate them into a particular coiled-coil oligomerization domain such that these peptides will form SAPN. By using these rules a wide variety of T-cell epitopes can be incorporated into the coiled-coil scaffold of the SAPN.

In a further aspect of this invention B-cell epitopes that are not coiled-coils are incorporated into the coiled-coil sequence of the SAPN oligomerization domain by inserting them between two stretches of coiled-coil segments, such that this whole sequence acts as a single oligomerization domain. This is of particular interest as the coiled-coil scaffold can provide means to restrict the conformation of the B-cell epitope to a conformation that is nearly identical to its native conformation.

Sources of T-Cell Epitopes

To incorporate T-cell epitopes into an oligomerization domain leading finally to a self-assembling peptide nanoparticle (SAPN), the T-cell epitopes can be chosen from different sources: For example, the T-cell epitopes can be determined by experimental methods, they are known from literature, they can be predicted by prediction algorithms based on existing protein sequences of a particular pathogen, or they may be de novo designed peptides or a combination of them.

There is a wealth of known T-cell epitopes available in the scientific literature. These T-cell epitopes can be selected from a particular pathogen (e.g. as in Examples 12, 13 and 14), from a cancer specific peptide sequence (e.g. as in Example 4), or they may be de novo designed peptides with a particular feature, e.g. the PADRE peptide (U.S. Pat. No. 5,736,142) that binds to many different MHC II molecules, which makes it a so-called promiscuous T-cell epitope (e.g. as in Example 1). There exist commonly accessible databases that contain thousands of different T-cell epitopes, for example the MHC-database "MHCBN VERSION 4.0" or the PDB-database "Protein Data Bank", or others.

It is well known and well documented that incorporation of HTL epitopes into an otherwise not immunogenic peptide sequence or attaching it to a non-peptidic antigen can make those much more immunogenic. The PanDR binding peptide HTL epitope PADRE has widely been used in vaccine design for a malaria, Alzheimer and many others vaccines.

According to the definition of the MHCBN database (supra) T-cell epitopes are peptides that have binding affinities ($IC_{50}$ values) of less than 50,000 nM to the corresponding MHC molecule. Such peptides are considered as MHC binders. According to this definition, as of August 2006, in the Version 4.0 of the MHCBN database the following data is available: 20717 MHC binders and 4022 MHC non-binders.

Suitable T-cell epitopes can also be obtained by using prediction algorithms. These prediction algorithms can either scan an existing protein sequence from a pathogen for putative T-cell epitopes, or they can predict, whether de novo designed peptides bind to a particular MHC molecule. Many such prediction algorithms are commonly accessible on the internet. Examples are SVRMHCdb (J. Wan et al., BMC Bioinformatics 2006, 7:463), SYFPEITHI, MHCPred, motif scanner or NetMHCIIpan for MHC II binding molecules and NetMHCpan for MHC I binding epitopes.

HTL epitopes as described herein and preferred for the design are peptide sequences that are either measured by biophysical methods or predicted by NetMHCIIpan to bind to any of the MHC II molecules with binding affinities ($IC_{50}$ values) better than 500 nM. These are considered weak binders. Preferentially these epitopes are measured by biophysical methods or predicted by NetMHCIIpan to bind to the MHC II molecules with $IC_{50}$ values better than 50 nM. These are considered strong binders.

CTL epitopes as described herein and preferred for the design are peptide sequences that are either measured by biophysical methods or predicted by NetMHCpan to bind to any of the MHC I molecules with binding affinities ($IC_{50}$ values) better than 500 nM. These are considered weak binders. Preferentially these epitopes are measured by biophysical methods or predicted by NetMHCpan to bind to the MHC I molecules with $IC_{50}$ values better than 50 nM. These are considered strong binders.

Places for T-Cell Epitopes

The T-cell epitopes can be incorporated at several places within the peptide sequence of the coiled-coil oligomerization domains D1 and or D2. To achieve this, the particular sequence with the T-cell epitope has to obey the rules for coiled-coil formation as well as the rules for MHC binding. The rules for coiled-coil formation have been outlined in detail above. The rules for binding to MHC molecules are incorporated into the MHC binding prediction programs that use sophisticated algorithms to predict MHC binding peptides.

There are many different HLA molecules, each of them having a restriction of amino acids in their sequence that will best bind to it. The binding motifs are summarized in Table 3. In this table the motif shows x for positions that can have any amino acid, and in square brackets the (list of) amino acids that can only be at a particular position of the binding motif.

TABLE 3

MHC-binding motifs for HLA genotypes

| MHC molecule | Motif[1)] | Reference[2)] |
|---|---|---|
| A*01 | xx[DE]xxxxx[Y] | SYFPEITHI |
| A*0101 | xx[DE]xxxxx[Y] | Marsh2000 |
| A*0201 | x[L(M)]xxxxxx[V(L)] | Marsh2000 |
| A*0201 | x[LM]xxxxxx[VL] | SYFPEITHI |
| A*0202 | x[L]xxxxxx[L] | Marsh2000 |
| A*0202 | x[L(A)]xxxxxx[LV] | SYFPEITHI |
| A*0204 | x[L]xxxxxx[L] | Marsh2000 |
| A*0204 | x[L]xxxxxx[L] | SYFPEITHI |
| A*0205 | x[V(QL)]xxxxxx[L] | Marsh2000 |
| A*0205 | xxxxxxxx[L] | SYFPEITHI |
| A*0206 | x[V(Q)]xxxxxxx | Marsh2000 |
| A*0206 | x[V(Q)]xxxxxx[V(L)] | SYFPEITHI |
| A*0207 | x[L][D]xxxxx[L] | Marsh2000 |
| A*0207 | x[L]xxxxxx[L] | SYFPEITHI |
| A*0214 | x[QV]xxx[K]xx[VL] | Luscher2001 |
| A*0214 | x[VQ(L)]xxxxxx[L] | Marsh2000 |
| A*0214 | x[VQL(A)]xxxxxx[L(VM)] | SYFPEITHI |
| A*0217 | x[L]xxxxxx[L] | SYFPEITHI |
| A*03 | x[LVM]xxxxxx[KYF] | SYFPEITHI |
| A*0301 | x[LVM(IAST)]xxxxxx[KY(FR)] | Marsh2000 |
| A*1101 | xxxxxxxx[K] | Marsh2000 |
| A*1101 | xxxxxxxx[KR] | SYFPEITHI |
| A*24 | x[Y(F)]xxxxxx[ILF] | SYFPEITHI |
| A*2402 | x[YF]xxxxxx[FWIL] | Marsh2000 |
| A*2402 | x[YF]xxxxxx[LFI] | SYFPEITHI |
| A*2501 | xxxxxxxxx[W] | Yusim2004 |
| A*2601 | x[VTIFL]xxxxxx[YF] | Marsh2000 |
| A*2601 | x[VTILF]xxxxxx[YF] | SYFPEITHI |
| A*2602 | x[VTILF]xxxxxx[YFML] | Marsh2000 |
| A*2602 | x[VTILF]xxxxxx[YF(ML)] | SYFPEITHI |
| A*2603 | x[VFILT]xxxxxx[YFML] | Marsh2000 |
| A*2603 | x[VTILF]xxxxxx[YFML] | SYFPEITHI |
| A*2902 | x[E(M)]xxxxxx[Y(L)] | Marsh2000 |
| A*2902 | x[E(M)]xxxxxx[Y(L)] | SYFPEITHI |
| A*3001 | x[YF(VLMIT)]xxxxxx[L(YFM)] | SYFPEITHI |
| A*3002 | x[YFLV]xxxxxx[Y] | SYFPEITHI |
| A*3003 | x[FYIVL]xxxxxx[Y] | SYFPEITHI |
| A*3004 | xxxxxxxx[YML] | SYFPEITHI |
| A*3101 | xxxxxxxx[R] | Marsh2000 |
| A*3101 | xxxxxxxx[R] | SYFPEITHI |
| A*3201 | x[I]xxxxxxx[W] | Yusim2004 |
| A*3303 | xxxxxxxx[R] | Marsh2000 |
| A*3303 | xxxxxxxx[R] | SYFPEITHI |
| A*6601 | x[TV(APLIC)]xxxxxx[RK] | SYFPEITHI |
| A*6801 | x[VT]xxxxxx[RK] | Marsh2000 |
| A*6801 | x[VT]xxxxxx[RK] | SYFPEITHI |
| A*6802 | x[TV]xxxxxx[VL] | Yusim2004 |
| A*6901 | x[VT(A)]xxxxxx[VL] | Marsh2000 |
| A*6901 | x[VTA]xxxxxx[VL(MQ)] | SYFPEITHI |
| B*07 | x[P]xxxxxx[LF] | SYFPEITHI |
| B*0702 | x[P]xxxxxx[L(F)] | Marsh2000 |
| B*0702 | x[P(V)]xxxxxx[L] | SYFPEITHI |
| B*0703 | x[P]xxxxxxx | Marsh2000 |
| B*0703 | x[P(ND)]xxxxxx[L] | SYFPEITHI |
| B*0705 | x[P]xxxxxxx | Marsh2000 |
| B*0705 | x[P]xxxxxx[L(F)] | SYFPEITHI |
| B*08 | xx[K(R)]x[KR]xxx[L(FM)] | SYFPEITHI |
| B*0801 | xx[K(R)]x[K(RH)]xxxx | Marsh2000 |
| B*0801 | xx[K(R)]xxxxxx | SYFPEITHI |
| B*0802 | xx[K(RY)]x[K(H)]xxxx | Marsh2000 |
| B*0802 | xx[K(RY)]x[K(H)]xxxx | SYFPEITHI |
| B*14 | x[RK]xx[RH]xxx[L] | SYFPEITHI |
| B*1402 | x[R(K)]xx[R(H)]xxx[L] | Marsh2000 |
| B*1501 | x[Q(LMVP)]xxxxxxx[YF] | Marsh2000 |
| B*1501 | x[QL(MVP)]xxxxxxx[FY] | SYFPEITHI |
| B*1502 | xxxxxxxx[YF(M)] | Marsh2000 |
| B*1502 | x[QLVP]xxxxxx[FYM] | SYFPEITHI |
| B*1503 | x[QK]xxxxxx[YF] | SYFPEITHI |
| B*1508 | x[P(A)]xxxxxx[YF] | Marsh2000 |
| B*1508 | x[PA]xxxxxx[YF] | SYFPEITHI |
| B*1509 | x[H]xxxxxx[L(F)] | Marsh2000 |

TABLE 3-continued

| MHC-binding motifs for HLA genotypes | | |
|---|---|---|
| MHC molecule | Motif[1)] | Reference[2)] |
| B*1509 | x[H]xxxxxx[LFM] | SYFPEITHI |
| B*1510 | x[H]xxxxxx[L(F)] | SYFPEITHI |
| B*1512 | x[Q(LM)]xxxxxx[YF] | SYFPEITHI |
| B*1513 | xxxxxxxx[W] | Marsh2000 |
| B*1513 | x[LIQVPM]xxxxxx[W] | SYFPEITHI |
| B*1516 | x[T(S)]xxxxxx[Y(IVFM)] | Marsh2000 |
| B*1516 | x[ST(F)]xxxxxx[IVYF] | SYFPEITHI |
| B*1517 | x[TS]xxxx[L]x[Y(F)] | Marsh2000 |
| B*1517 | x[TS]xxxxxx[YFLI] | SYFPEITHI |
| B*1518 | x[H]xxxxxx[Y(F)] | SYFPEITHI |
| B*18 | x[E]xxxxxxx | Marsh2000 |
| B*27 | x[R]xxxxxxx | SYFPEITHI |
| B*2701 | x[RQ]xxxxxx[Y] | Marsh2000 |
| B*2701 | x[RQ]xxxxxx[Y] | SYFPEITHI |
| B*2702 | x[R]xxxxxx[FY(ILW)] | Marsh2000 |
| B*2702 | x[R]xxxxxx[FYILW] | SYFPEITHI |
| B*2703 | x[R(M)]xxxxxxx | Marsh2000 |
| B*2703 | x[R]xxxxxx[YF(RMWL)] | SYFPEITHI |
| B*2704 | x[R]xxxxxx[YLF] | Marsh2000 |
| B*2704 | x[R]xxxxxx[YLF] | SYFPEITHI |
| B*2705 | x[R(K)]xxxxxxx | Marsh2000 |
| B*2705 | x[R]xxxxxx[LFYRHK(MI)] | SYFPEITHI |
| B*2706 | x[R]xxxxxx[L] | Marsh2000 |
| B*2706 | x[R]xxxxxx[L] | SYFPEITHI |
| B*2707 | x[R]xxxxxx[L] | Marsh2000 |
| B*2707 | x[R]xxxxxx[LF] | SYFPEITHI |
| B*2709 | x[R]xxxxxx[LVFIM] | Marsh2000 |
| B*2710 | x[R]xxxxxx[YF] | Marsh2000 |
| B*35 | x[P(AVYRD)]xxxxxx[YFMLI] | SYFPEITHI |
| B*3501 | x[P(AV)]xxxxxxx | Marsh2000 |
| B*3501 | x[P(AVYRD)]xxxxxx[YFMLI] | SYFPEITHI |
| B*3503 | x[P(A)]xxxxxx[ML(F)] | Marsh2000 |
| B*3503 | x[P(MILFV)]xxxxxx[ML(F)] | SYFPEITHI |
| B*3701 | x[D(E)]xxxxx[FML][IL] | Marsh2000 |
| B*3701 | x[DE(HPGSL)]xxxxx[FML(QKYL)][IL(TENDQ GH)] | SYFPEITHI |
| B*3801 | xxxxxxxx[FL] | Marsh2000 |
| B*3801 | xxxxxxxx[FL(I)] | SYFPEITHI |
| B*3901 | x[RH]xxxxxx[L] | Marsh2000 |
| B*3901 | x[RH]xxxxxx[L(VIM)] | SYFPEITHI |
| B*3902 | x[KQ]xxxxxx[L] | Marsh2000 |
| B*3902 | x[KQ]xxxxxx[L(FM)] | SYFPEITHI |
| B*3909 | x[RH(P)]xxxxxx[LF] | SYFPEITHI |
| B*40 | x[E]xxxxxx[LWMATR] | SYFPEITHI |
| B*4001 | x[E]xxxxxx[L] | Marsh2000 |
| B*4001 | x[E]xxxxxx[L] | SYFPEITHI |
| B*4002 | x[E]xxxxxx[IAVL] | Yusim2004 |
| B*4006 | x[E]xxxxxx[V] | Marsh2000 |
| B*4006 | x[E(P)]xxxxxx[V(AP)] | SYFPEITHI |
| B*4201 | x[P]xxxxxx[L] | Yusim2004 |
| B*44 | x[E]xxxxxx[Y] | SYFPEITHI |
| B*4402 | x[E]xxxxxx[YF] | Marsh2000 |
| B*4402 | x[E(MILD)]xxxxxx[FY] | SYFPEITHI |
| B*4403 | x[E]xxxxxx[YF] | Marsh2000 |
| B*4403 | x[E(MILVD)]xxxxxx[YF] | SYFPEITHI |
| B*4601 | xxxxxxxx[YF] | Marsh2000 |
| B*4601 | x[M(I)]xxxxxx[YF] | SYFPEITHI |
| B*4801 | x[QK]xxxxxx[L] | Marsh2000 |
| B*4801 | x[QK(M)]xxxxxx[L] | SYFPEITHI |
| B*5101 | xxxxxxxx[FI] | Marsh2000 |
| B*5101 | x[APG(WF)]xxxxxx[VI(WMVL)] | SYFPEITHI |
| B*5102 | x[APG]xxxxxx[IV] | Marsh2000 |
| B*5102 | x[APG]xxxxxx[IV] | SYFPEITHI |
| B*5103 | xxxxxxxx[VIF] | Marsh2000 |
| B*5103 | x[APG(FW)]xxxxxx[VIF] | SYFPEITHI |
| B*5201 | xxxxxxx[IV][IV] | Marsh2000 |
| B*5201 | xxxxxxx[IV(MF)][IV(MF)] | SYFPEITHI |
| B*5301 | x[P]xxxxxxx | Marsh2000 |
| B*5301 | x[P]xxxxxx[WFL] | SYFPEITHI |
| B*5401 | x[P]xxxxxxx | Marsh2000 |
| B*5401 | x[P]xxxxxxx | SYFPEITHI |
| B*5501 | x[P]xxxxxxx | Marsh2000 |
| B*5501 | x[P]xxxxxxx | SYFPEITHI |
| B*5502 | x[P]xxxxxxx | Marsh2000 |
| B*5502 | x[P]xxxxxxx | SYFPEITHI |
| B*5601 | x[P]xxxxxxx | Marsh2000 |

TABLE 3-continued

MHC-binding motifs for HLA genotypes

| MHC molecule | Motif[1)] | Reference[2)] |
|---|---|---|
| B*5601 | x[P]xxxxxx[A(L)] | SYFPEITHI |
| B*5701 | x[ATS]xxxxxx[FW] | Marsh2000 |
| B*5701 | x[ATS]xxxxxx[FWY] | SYFPEITHI |
| B*5702 | x[ATS]xxxxxx[FW] | Marsh2000 |
| B*5702 | x[ATS]xxxxxx[FW] | SYFPEITHI |
| B*5801 | x[ATS]xxxxxx[WF] | Marsh2000 |
| B*5801 | x[AST(G)]xxxxxx[FW(Y)] | SYFPEITHI |
| B*5802 | x[ST]xxx[R]xx[F] | Marsh2000 |
| B*5802 | x[ST]xxx[R]xx[F] | SYFPEITHI |
| B*6701 | x[P]xxxxxxx | Marsh2000 |
| B*6701 | x[P]xxxxxxx | SYFPEITHI |
| B*7301 | x[R]xxxxxx[P] | Marsh2000 |
| B*7301 | x[R]xxxxxx[P] | SYFPEITHI |
| B*7801 | x[PAG]xxxxxxx | Marsh2000 |
| B*7801 | x[PAG]xxxxx[A(KS)]x | SYFPEITHI |
| B*8101 | x[P]xxxxxx[L] | Yusim2004 |
| Cw*0102 | xx[P]xxxxx[L] | Marsh2000 |
| Cw*0102 | x[AL]xxxxxx[L] | SYFPEITHI |
| Cw*0103 | x[AL]xxxxxx[L] | Yusim2004 |
| Cw*0202 | x[A]xxxxxx[L] | Yusim2004 |
| Cw*0203 | x[A]xxxxxx[L] | Yusim2004 |
| Cw*0301 | xxxxxxxx[LFMI] | SYFPEITHI |
| Cw*0302 | x[A]xxxxxx[FWY] | Yusim2004 |
| Cw*0303 | x[A]xxxxxx[LM] | Yusim2004 |
| Cw*0304 | x[A]xxxxxx[LM] | Marsh2000 |
| Cw*0304 | x[A]xxxxxx[LM] | SYFPEITHI |
| Cw*0305 | x[A]xxxxxx[LM] | Yusim2004 |
| Cw*0306 | x[A]xxxxxx[LM] | Yusim2004 |
| Cw*0307 | x[A]xxxxxx[LF] | Yusim2004 |
| Cw*0308 | x[A]xxxxxx[LM] | Yusim2004 |
| Cw*0309 | x[A]xxxxxx[LM] | Yusim2004 |
| Cw*0401 | x[YP]xxxxxxx | Marsh2000 |
| Cw*0401 | x[YPF]xxxxxx[LFM] | SYFPEITHI |
| Cw*0402 | x[YP]xxxxxx[LF] | Yusim2004 |
| Cw*0403 | x[P]xxxxxx[LF] | Yusim2004 |
| Cw*0404 | x[YP]xxxxxx[LF] | Yusim2004 |
| Cw*0405 | x[YP]xxxxxx[LF] | Yusim2004 |
| Cw*0406 | x[P]xxxxxx[LF] | Yusim2004 |
| Cw*0501 | x[A]xxxxxx[LF] | Yusim2004 |
| Cw*0502 | x[A]xxxxxx[LF] | Yusim2004 |
| Cw*0601 | xxxxxxxx[LIVY] | SYFPEITHI |
| Cw*0602 | xxxxxxxx[L] | Marsh2000 |
| Cw*0602 | xxxxxxxx[LIVY] | SYFPEITHI |
| Cw*0603 | x[ALP]xxxxxx[L] | Yusim2004 |
| Cw*0604 | x[RQ]xxxxxx[L] | Yusim2004 |
| Cw*0701 | x[RHK]xxxxxx[Y] | Yusim2004 |
| Cw*0702 | xxxxxxxx[YFL] | SYFPEITHI |
| Cw*0703 | x[YP]xxxxxx[YL] | Yusim2004 |
| Cw*0704 | x[RQ]xxxxxx[LM] | Yusim2004 |
| Cw*0705 | x[RQ]xxxxxx[Y] | Yusim2004 |
| Cw*0706 | x[RHK]xxxxxx[Y] | Yusim2004 |
| Cw*0707 | x[RHK]xxxxxx[YL] | Yusim2004 |
| Cw*0708 | x[RQ]xxxxxx[YL] | Yusim2004 |
| Cw*0709 | x[RHK]xxxxxx[YL] | Yusim2004 |
| Cw*0710 | x[YP]xxxxxx[FWY] | Yusim2004 |
| Cw*0711 | x[R]xxxxxx[LM] | Yusim2004 |
| Cw*0712 | x[R]xxxxxx[LM] | Yusim2004 |
| Cw*0801 | x[A]xxxxxx[LM] | Yusim2004 |
| Cw*0802 | x[A]xxxxxx[LM] | Yusim2004 |
| Cw*0803 | x[A]xxxxxx[LM] | Yusim2004 |
| Cw*0804 | x[A]xxxxxx[LM] | Yusim2004 |
| Cw*0805 | x[A]xxxxxx[LM] | Yusim2004 |
| Cw*0806 | x[A]xxxxxx[LM] | Yusim2004 |
| Cw*1202 | x[A]xxxxxx[FWY] | Yusim2004 |
| Cw*1203 | x[A]xxxxxx[FWY] | Yusim2004 |
| Cw*1204 | x[A]xxxxxx[L] | Yusim2004 |
| Cw*1205 | x[A]xxxxxx[L] | Yusim2004 |
| Cw*1206 | x[A]xxxxxx[FWY] | Yusim2004 |
| Cw*1402 | x[YP]xxxxxx[FWY] | Yusim2004 |
| Cw*1403 | x[YP]xxxxxx[FWY] | Yusim2004 |
| Cw*1404 | x[YP]xxxxxx[FWY] | Yusim2004 |
| Cw*1502 | x[A]xxxxxx[LMYF] | Yusim2004 |
| Cw*1503 | x[A]xxxxxx[LMYF] | Yusim2004 |
| Cw*1504 | x[A]xxxxxx[L] | Yusim2004 |

TABLE 3-continued

| MHC-binding motifs for HLA genotypes | | |
|---|---|---|
| MHC molecule | Motif[1)] | Reference[2)] |
| Cw*1505 | x[A]xxxxxx[L] | Yusim2004 |
| Cw*1506 | x[A]xxxxxx[LM] | Yusim2004 |
| Cw*1507 | x[A]xxxxxx[LMY] | Yusim2004 |
| Cw*1601 | x[A]xxxxxx[FWY] | Yusim2004 |
| Cw*1602 | x[A]xxxxxx[L] | Yusim2004 |
| Cw*1604 | x[A]xxxxxx[L] | Yusim2004 |
| Cw*1701 | x[A]xxxxxx[L] | Yusim2004 |
| Cw*1702 | x[A]xxxxxx[L] | Yusim2004 |
| Cw*1801 | x[RQ]xxxxxx[LY] | Yusim2004 |
| Cw*1802 | x[RQ]xxxxxx[LY] | Yusim2004 |
| DPA1*0102/DPB1*0201 | [FLMVWY]xxx[FLMY]xx[IAMV] | SYFPEITHI |
| DPA1*0103/DPB1*0201 | [YLVFK]xx[DSQT]x[YFWV]xx[LVI] | Marsh2000 |
| DPA1*0103/DPB1*0201 | [FLM]xxx[FL]xx[IA] | Marsh2000 |
| DPA1*0201/DPB1*0401 | [FLYM(IVA)]xxxxx[FLY(MVIA)]xx[VYI(AL)] | Marsh2000 |
| DPA1*0201/DPB1*0401 | [FLYMIVA]xxxxx[FLYMVIA]xx[VYIAL] | SYFPEITHI |
| DPA1*0201/DPB1*0901 | [RK]xxxx[AGL]xx[LV] | Marsh2000 |
| DPB1*0301 | x[R]xxxxxxx | Marsh2000 |
| DQA1*0101/DQB1*0501 | [L]xxx[YFW] | Marsh2000 |
| DQA1*0102/DQB1*0602 | xxxxx[LIV(APST)]xx[AGST(LIVP)] | Marsh2000 |
| DQA1*0301/DQB1*0301 | xx[AGST]x[AVLI] | Marsh2000 |
| DQA1*0301/DQB1*0301 | [DEW]xx[AGST]x[ACLM] | SYFPEITHI |
| DQA1*0301/DQB1*0302 | [RK]xxxx[AG]xx[NED] | Marsh2000 |
| DQA1*0301/DQB1*0302 | [TSW]xxxxxxx[RE] | SYFPEITHI |
| DQA1*0501/DQB1*0201 | [FWYILV]xx[DELVIH]x[PDE(H)][ED]x[FYWVILM] | Marsh2000 |
| DQA1*0501/DQB1*0201 | [FWYILV]xx[DELVIH]x[PDEHPA][DE]x[FWYILVM] | SYFPEITHI |
| DQA1*0501/DQB1*0301 | [FYIMLV]xxx[VLIMY]x[YFMLVI] | Marsh2000 |
| DQA1*0501/DQB1*0301 | [WYAVM]xx[A]x[AIVTS]xxx[QN] | SYFPEITHI |
| DQB1*0602 | [AFCILMNQSTVWYDE]x[AFGILMNQSTVWYCDE][AFGILMNQSTVWY]x[LIVAPST]xx[ASTGLIVP] | SYFPEITHI |
| DRB1*0101 | [YFWLIMVA]xx[LMAIVN]x[AGSTCP]xx[LAIVNFYMW] | Marsh2000 |
| DRB1*0101 | [YVLFIAMW]xx[LAIVMNQ]x[AGSTCP]xx[LAIVNFY] | SYFPEITHI |
| DRB1*0102 | [ILVM]xx[ALM]x[AGSTCP]xx[ILAMYW] | Marsh2000 |
| DRB1*0102 | [ILVM]xx[ALM]x[AGSTP]xx[ILAMYW] | SYFPEITHI |
| DRB1*0301 | [LIFMV]xx[D]x[KR(EQN)]x[L][YLF] | Marsh2000 |
| DRB1*0301 | [LIFMV]xx[D]x[KREQN]xx[YLF] | SYFPEITHI |
| DRB1*0301 or DRB3*0201 | [FILVY]xx[DNQT] | Marsh2000 |
| DRB1*0401 | [FLV]xxxxxxx[NQST] | Marsh2000 |
| DRB1*0401 or DRB4 | [FYWILVM]xx[FWILVADE]x[NSTQHR]xx[K] | Marsh2000 |
| DRB1*0401 or DRB4*0101 | [FYW]xxxxxxx[ST] | Marsh2000 |
| DRB1*0401 or DRB4*0101 | [FYWILVM]xx[PWILVADE]x[NSTQHR][DEHKNQRSTYACILMV]x[DEHKNQRSTYACILMV] | SYFPEITHI |
| DRB1*0402 or DRB4 | [VILM]xx[YFWILMRNH]x[NSTQHK]x[RKHNQP]x[H] | Marsh2000 |
| DRB1*0402 or DRB4 | [VILM]xx[YFWILMRN]x[NQSTK][RKHNQP]x[DEHLNQRSTYCILMVHA] | SYFPEITHI |
| DRB1*0404 or DRB4 | [VILM]xx[FYWILVMADE]x[NTSQR]xx[K] | Marsh2000 |
| DRB1*0404 or DRB4 | [VILM]xx[FYWILVMADE]x[NTSQR]xx[K] | SYFPEITHI |
| DRB1*0405 or DRB4 | [FYWVILM]xx[VILMDE]x[NSTQKD]xxx[DEQ] | Marsh2000 |
| DRB1*0405 or DRB4 | [FYWVILM]xx[VILMDE]x[NSTQKD]xxx[DEQ] | SYFPEITHI |
| DRB1*0405 or DRB4*0101 | [Y]xxxx[VT]xxx[D] | Marsh2000 |
| DRB1*0407 or DRB4 | [FYW]xx[AVTK]x[NTDS]xxx[QN] | Marsh2000 |
| DRB1*0407 or DRB4 | [FYW]xx[AVK]x[NTDS]xxx[QN] | SYFPEITHI |
| DRB1*0701 | [FILVY]xxxx[NST] | Marsh2000 |
| DRB1*0701 | [FYWILV]xx[DEHKNQRSTY]x[NST]xx[VILYF] | SYFPEITHI |
| DRB1*0801 | [FILVY]xxx[HKR] | Marsh2000 |
| DRB1*0901 or DRB4*0101 | [YFWL]xx[AS] | Marsh2000 |
| DRB1*0901 or DRB4*0101 | [WYFL]xx[AVS] | SYFPEITHI |
| DRB1*1101 | [YF]xx[LVMAFY]x[RKH]xx[AGSP] | Marsh2000 |
| DRB1*1101 | [WYF]xx[LVMAFY]x[RKH]xx[AGSP] | SYFPEITHI |
| DRB1*1101 or DRB3*0202 | [YF]xxxx[RK]x[RK] | Marsh2000 |
| DRB1*1104 | [ILV]xx[LVMAFY]x[RKH]xx[AGSP] | Marsh2000 |
| DRB1*1104 | [ILV]xx[LVMAFY]x[RKH]xx[AGSP] | SYFPEITHI |
| DRB1*1201 or DRB3 | [ILFY(V)]x[LNM(VA)]xx[VY(FIN)]xx[YFM(IV)] | Marsh2000 |
| DRB1*1201 or DRB3 | [ILFYV]x[LMNVA]xx[VYFINA]xx[YFMIV] | SYFPEITHI |
| DRB1*1301 | [IVF]xx[YWLVAM]x[RK]xx[YFAST] | Marsh2000 |
| DRB1*1301 | [ILV]xx[LVMAWY]x[RK]xx[YFAST] | SYFPEITHI |
| DRB1*1301 or DRB3*0101 | [ILV]xxxx[RK]xx[Y] | Marsh2000 |
| DRB1*1302 | [YFVAI]xx[YWLVAM]x[RK]xx[YFAST] | Marsh2000 |

TABLE 3-continued

| MHC-binding motifs for HLA genotypes | | |
|---|---|---|
| MHC molecule | Motif[1)] | Reference[2)] |
| DRB1*1302 | [YFVAI]xx[LVMAWY]x[RK]xx[YFAST] | SYFPEITHI |
| DRB1*1302 or DRB3*1301 | [ILFY]xxxx[RK]xx[Y] | Marsh2000 |
| DRB1*1501 | [LVI]xx[FYI]xx[ILVMF] | Marsh2000 |
| DRB1*1501 | [LVI]xx[FYI]xx[ILVMF] | YFPEITHI |
| DRB1*1501 or DRB5*0101 | [ILV]xxxxxxxx[HKR] | Marsh2000 |
| DRB3*0202 | [YFIL]xx[N]x[ASPDE]xx[LVISG] | Marsh2000 |
| DRB3*0202 | [YFIL]xx[N]x[ASPDE]xx[LVISG] | SYFPEITHI |
| DRB3*0301 | [ILV]xx[N]x[ASPDE]xx[ILV] | Marsh2000 |
| DRB3*0301 | [ILV]xx[N]x[ASPDE]xx[ILV] | SYFPEITHI |
| DRB5*0101 | [FYLM]xx[QVIM]xxxx[RK] | Marsh2000 |
| DRB5*0101 | [FYLM]xx[QVIM]xxxx[RK] | SYFPEITHI |

[1)]The anchor residues are shown in the square brackets. The preferred but not dominant amino acids in the anchor positions are shown in parentheses. For example, the motif x-[VTILF]-x-x-x-x-x-[YF(ML)] means that second and C-terminal positions are anchor positions. The dominant amino acids at the second position are V, T, I, L, F, and at the C-terminal anchor position the dominant amino acids are Y and F, while M and L are preferred but not dominant.
[2)]Marsh2000: Marsh S. G. E., Parham P. and Barber L. D., The HLA Factsbook. Academic Press, San Diego, 2000. URL: http://www.anthonynolan.com/HIG/. SYFPEITHI: The SYFPEITHI Database of MHC Ligands, Peptide Motifs and Epitope Prediction. January 2003. URL: http://www.syfpeithi.de. Luscher2001: Luscher M. A. et al., Immunogenetics. 2001, 53(1): 10-14. Yusim2004: Yusim K. et al., Appl Bioinformatics 2005, 4(4): 217-225.

Many of the MHC molecules have very similar binding motifs and hence these can be grouped into so-called HLA supertypes. The binding motifs for these supertypes are summarized in Table 4.

TABLE 4

| MHC-binding motifs of HLA supertypes | | |
|---|---|---|
| Supertype | Motif | Genotypes |
| A1 | x[TI(SVLM)]xxxxxx[WFY] | A*0101, A*0102, A*2501, A*2601, A*2604, A*3201, A*3601, A*4301, A*8001 |
| A2 | x[LIVMATQ]xxxxxx[LIVMAT] | A*0201, A*0202, A*0203, A*0204, A*0205, A*0206, A*0207, A*6802, A*6901 |
| A3 | x[AILMVST]xxxxxx[RK] | A*0301, A*1101, A*3101, A*3301, A*6801 |
| A24 | x[YF(WIVLMT)]xxxxxx[FI(YWLM)] | A*2301, A*2402, A*2403, A*2404, A*3001, A*3002, A*3003 |
| B7 | x[P]xxxxxx[ALIMVFWY] | B*0702, B*0703, B*0704, B*0705, B*1508, B*3501, B*3502, B*3503, B*51, B*5301, B*5401, B*5501, B*5502, B*5601, B*5602, B*6701, B*7801 |
| B27 | x[RKH]xxxxxx[FLY(WMI)] | B*1401, B*1402, B*1503, B*1509, B*1510, B*1518, B*2701, B*2702, B*2703, B*2704, B*2705, B*2706, B*2707, B*2708, B*3801, B*3802, B*3901, B*3902, B*3903, B*3904, B*4801, B*4802, B*7301 |
| B44 | x[E(D)]xxxxxx[FWYLIMVA] | B*18, B*3701, B*4001, B*4006, B*4101, B*4402, B*4403, B*4501, B*4901, B*5001 |
| B58 | x[AST]xxxxxx[FWY(LIV)] | B*1516, B*1517, B*5701, B*5702, B*58 |
| B62 | x[QL(IVMP)]xxxxxx[FWY(MIV)] | B*1301, B*1302, B*1501, B*1502, B*1506, B*1512, B*1513, B*1514, B*1519, B*1521, B*4601, B*52 |

The frequency of occurrence of a particular amino acid at a certain position of the T-cell epitope can also be summarized. For MHC binding the positions 1, 4, 6 and 9 in a T-cell epitope are the most critical ones. The most preferred residues at these positions are listed in Table 5, however, the preferences for particular amino acids at these position vary largely between the different MHC molecules. Therefore, as mentioned above, binding of a particular amino acid sequence to a MHC molecule can be much more accurately predicted by the prediction programs listed above.

TABLE 5

Overall frequency of amino acids at particular postions of T-cell epitopes (derived from Motif Scanner)

| Pos 1 | | Pos 2 | Pos 3 | | Pos 4 | | Pos 5 | | Pos 6 | | Pos 7 | | Pos 8 | | Pos 9 | | Pos10 | |
|---|---|---|---|---|---|---|---|---|---|---|---|---|---|---|---|---|---|---|
| L | 37 | | L | 2 | V | 21 | H | 1 | S | 20 | M | 3 | K | 2 | Y | 17 | Q | 4 |
| I | 35 | | M | 2 | L | 20 | K | 1 | K | 17 | V | 3 | R | 2 | L | 14 | D | 3 |
| V | 33 | | N | 2 | M | 20 | R | 1 | R | 17 | L | 3 | H | 1 | A | 14 | E | 2 |
| F | 31 | | V | 2 | A | 20 | | | T | 17 | I | 3 | N | 1 | S | 14 | H | 2 |
| Y | 28 | | A | 2 | Y | 15 | | | N | 16 | F | 2 | Q | 1 | I | 13 | N | 2 |
| M | 16 | | | | I | 14 | | | Q | 10 | K | 2 | P | 1 | F | 11 | K | 1 |
| W | 13 | | | | F | 11 | | | A | 9 | R | 2 | | | V | 11 | R | 1 |
| A | 4 | | | | W | 10 | | | D | 8 | H | 2 | | | T | 8 | | |
| | | | | | N | 10 | | | P | 8 | N | 2 | | | M | 7 | | |
| | | | | | D | 10 | | | H | 7 | Q | 2 | | | K | 6 | | |
| | | | | | E | 7 | | | E | 6 | P | 1 | | | G | 6 | | |
| | | | | | Q | 5 | | | G | 4 | D | 1 | | | N | 5 | | |
| | | | | | K | 3 | | | V | 3 | E | 1 | | | P | 4 | | |
| | | | | | R | 3 | | | C | 3 | S | 1 | | | R | 4 | | |
| | | | | | T | 3 | | | Y | 2 | T | 1 | | | W | 3 | | |
| | | | | | S | 3 | | | F | 2 | Y | 1 | | | H | 3 | | |
| | | | | | H | 2 | | | I | 2 | A | 1 | | | Q | 3 | | |
| | | | | | P | 1 | | | | | C | 1 | | | E | 2 | | |
| | | | | | | | | | | | | | | | D | 2 | | |
| | | | | | | | | | | | | | | | C | 2 | | |

From this Table 5 it is easily visible that, for example, the most frequently encountered amino acids at position 1 and position 4 are the ones that are found at core positions of the coiled-coil heptad repeat (indicated by underlining). Position 1 and 4 can be superposed on the heptad repeat positions aa(a) and aa(d). Therefore, a T-cell epitope with the amino acid L in position 1 and amino acid V in position 4 is perfectly in agreement with a coiled-coil peptide having the same amino acids at the core positions aa(a) and aa(d) of the heptad repeat. Therefore, if a peptide sequence obeys both, T-cell binding motif restriction as well as coiled-coil heptad repeat motif restriction, it can be incorporated into the coiled-coil oligomerization domain of the SAPN. This can be achieved for a large number of T-cell epitopes by adjusting the alignment of peptide sequence such that the T-cell binding motif overlaps with the coiled-coil forming motif.

Engineering T-Cell Epitopes into Coiled-Coil

To engineer SAPN that incorporate T-cell epitopes in the coiled-coil oligomerization domain of the SAPN, three steps have to be taken. In a first step a candidate T-cell epitope has to be chosen by using known T-cell epitopes from the literature or from databases or predicted T-cell epitopes by using a suitable epitope prediction program. In a second step a proteasomal cleavage site has to be inserted at the C-terminal end of the CTL epitopes. This can be done by using the prediction program for proteasomal cleavage sites PAProc (Hadeler K. P. et al., Math. Biosci. 2004, 188:63-79) and modifying the residues immediately following the desired cleavage site. This second step is not required for HTL epitopes. In the third and most important step the sequence of the T-cell epitope has to be aligned with the coiled-coil sequence such that it is best compatible with the rules for coiled-coil formation as outlined above. Whether the sequence with the incorporated T-cell epitope will indeed form a coiled-coil can be predicted, and the best alignment between the sequence of the T-cell epitope and the sequence of the coiled-coil repeat can be optimized by using coiled-coil prediction programs such as COILS (Gruber M. et al., J. Struct. Biol. 2006, 155(2):140-5) or MULTICOIL which are available on the internet.

Even if it is not possible to find a suitable alignment—maybe because the T-cell epitope contains a glycine or even a proline which is not compatible with a coiled-coil structure—the T-cell epitope may be incorporated into the oligomerization domain (see Example 3). In this case the T-cell epitope has to be flanked by strong coiled-coil forming sequences of the same oligomerization state. This will either stabilize the coiled-coil structure to a sufficient extent or alternatively it can generate a loop structure within this coiled-coil oligomerization domain. This is essentially the same procedure as described in the next section for the incorporation of B-cell epitopes into the coiled-coil core sequence of the SAPN.

Engineering B-Cell Epitopes into the Coiled-Coil Core

In a particular aspect of this invention the incorporation into the coiled-coil core of the SAPN of small B-cell epitopes that are not α-helical is envisaged. This can be accomplished by the same procedure as outlined above for the T-cell epitopes that are not compatible with a coiled-coil structure. The structure of T4 fibritin (pdb accession code 1aa0) contains two loops structures within its coiled-coil. The loops protrude from the coiled-coil helix between two helical turns such that the helical structure of the coiled-coil is not interrupted.

In fibritin, the loops leave the helix at position aa(b) of the coiled-coil and reenter the helix at position aa(c) of the coiled-coil sequence. One of the loops is a short beta-turn while the other is a more irregular loop structure. The spacing between the residues aa(b) and aa(c) in a coiled-coil is ideally suited to serve as anchor points for an antiparallel beta-turn peptide. When residues aa(b) or aa(c) or both of them are glycine residues this allows for the needed flexibility of the protein secondary structure to exit and reenter the alpha-helix of the coiled-coil.

```
                                                    (SEQ ID NO: 4)
..VQNLQVEIGNNSAGIKGQVVALNTLVNGTNPNGSTVEERGLTNSIKANETNIASVTQEV...
  a  d   a    d  a  d  a             d  a  d  a  d  a
```

In the sequence of fibritin above the loops structures are displayed in italic and the residues at the aa(b) and aa(c) positions (where the two loops exit and reenter the helix) are indicated by underscores. Three of these four residues are glycine residues. Taking this as a template, a B-cell epitope that has an anti-parallel beta-turn conformation can now be incorporated into the coiled-coil core of the SAPN. The coiled-coil structure has to be sufficiently stable to allow incorporation of such a loops structure, hence it must be able to form coiled-coils on both sides of the loop. The smallest autonomously folding coiled-coil sequence described so far is two heptad repeats long. In the sequence below the tip of the V3 epitope from the protein gp120 of HIV, which is an anti-parallel beta-turn peptide, is incorporated into the coiled-coil of a designed stable coiled-coil with flanking helices of more than two heptad repeats on both sides. These are very stable coiled-coil fragments derived from Burkhard P. et al., J Mol Biol 2002, 318:901-910.

```
                                                      (SEQ ID NO: 5)
LEELERRLEELERRLEELERRLGSIRIGPGQTFYAGVDLELAALRRRLEELAR
 a  d  a  d  a  d  a              d  a  d  a  d core residues
```

This will restrict the conformation of the V3 loop within the coiled-coil to an anti-parallel beta-turn conformation which corresponds to the native conformation of this peptide on the protein.

Preferred Design

To engineer a SAPN with the best immunological profile for a given particular application the following consideration have to be taken into account:

CTL epitopes require a proteasomal cleavage site at their C-terminal end. The epitopes should not be similar to human sequences to avoid autoimmune responses—except when it is the goal to elicit an immune response against a human peptide. Possible examples are the cancer-specific CTL epitopes of Example 4.

Accordingly a SAPN is preferred wherein at least one of the T-cell epitopes is a CTL epitope, and, in particular, wherein the sequence further contains a proteasomal cleavage site after the CTL epitope.

Likewise preferred is a SAPN wherein at least one of the T-cell epitopes is a HTL epitope, in particular, a pan-DR-binding HTL epitope. Such pan-DR-binding HTL epitopes bind to many of the MHC class II molecules as listed at the bottom of Table 3 and are therefore recognized in a majority of healthy individuals, which is critical for a good vaccine.

Also preferred is a SAPN wherein the sequence D1-L-D2 contains a series of overlapping T-cell epitopes, either if D1 or D2 are a trimer (Examples 7 and 8), a tetramer (Examples 9) or a pentamer (Examples 10).

B-cell epitopes need to be displayed at the surface of the SAPN. They may or may not be part of the coiled-coil sequence, i.e. the coiled-coil itself may partially be a B-cell epitope depending on whether the portion of the coiled-coil is surface accessible. For example the B-cell epitope composed of the trimeric coiled-coil of the surface proteins of enveloped viruses can be displayed on the surface of the SAPN and be part of coiled-coil sequence at the same time. An example of such a design is presented in Raman S. et al., Nanomedicine: Nanotechnology, Biology, and Medicine 2006; 2:95-102. Coiled-coils of any oligomerization state in general are exceptionally well-suited to be presented in conformation specific manner by the SAPN. Coiled-coils are abundant, not only in enveloped virus surface proteins but also, for example, in the genome of the malaria pathogen *Plasmodium falciparum* (Villard V. et al., PLoS ONE 2007; 2(7):e645).

In general, however, the B-cell epitopes will not be part of the coiled-coil oligomerization domains, or they may be composed of a coiled-coil and an additional portion that is not a coiled-coil, as for example the trimeric autotransporter adhesions (TAA) of bacteria, which have a coiled-coil stalk and a globular head domain, such as the TAA of *N. meningitidis*.

Of particular interest are proteins as B-cell epitopes that are themselves oligomeric, such as trimeric hemagglutinin, and the tetrameric sialidase or M2 surface proteins of influenza.

Considerations for the Design of a Vaccine Against a Pathogen

Such a vaccine preferably contains all three types of epitopes, B-cell, HTL and CTL epitopes. (1) Preferably only one (or very few) B-cell epitope should be placed at either end of the peptide chains. This will place the B-cell epitope on the surface of the SAPN in a repetitive antigen display. (2) The HTL epitopes should be as promiscuous as possible. They do not necessarily need to be derived from the pathogen but can be peptides that elicit a strong T-help immune response. An example would be the PADRE peptide. Preferably these are the T-cell epitopes that are incorporated into the D1-L-D2 core sequence of the SAPN. (3) The CTL epitopes need to be pathogen specific, they need to have C-terminal proteasomal cleavage sites. Since the T-cell epitopes do not require repetitive antigen display several different T-cell epitopes can be incorporated into one single SAPN by co-assembly of different peptide chains that all have the same nanoparticle forming D1-L-D2 core but carry different T-cell epitopes that are not part of the core forming sequence and hence would not be incorporated into the coiled-coil sequences.

In a similar manner peptide chains carrying an ER-targeting signal, i.e. a signal peptide that induces the transport of a protein or peptide to the endoplasmic reticulum (ER), can be co-assembled into the same SAPN to bring the CTL epitopes into the ER for proper presentation by the MHC I molecules since cross-presentation is not very efficient in humans. The ER targeting signal, however, does not need to be on a separate peptide chain, it can be in the same peptide as the CTL epitopes. A suitable ER signal peptide would be for example the ER targeting signal (E3/19K) MRYMILGLLALAAVCSA (SEQ ID NO:6).

Therapeutic Vaccine Aimed to Generate a Strong Antibody Response

A therapeutic vaccine aimed to generate a strong antibody response is particularly useful for the treatment of Alzheimer, hypertension, obesity, drug addictions, or inflammation. For such a vaccine preferably only one B-cell epitope is used. The strong humoral immune response due to repetitive antigen display can be further enhanced by including one or more promiscuous HTL epitopes into the SAPN. Preferably these are the T-cell epitopes that are incorporated into the D1-L-D2 core sequence of the SAPN. Furthermore there should be as few and as weakly binding CTL epitopes as possible—in particular not against a human peptide to avoid autoimmune responses.

Therapeutic Vaccine to Induce a CTL Response, e.g. Against Cancer

In this case no B-cell epitope has to be used. The immune response against the particular CTL epitopes (for example MAGE-1,2,3; MART-1,2,3; or Her-2/neu, see also Example 4) is further enhanced by including one or more promiscuous HTL epitopes into the SAPN.

Self-Assembling Peptide Nanoparticles (SAPN) as Adjuvants

A SAPN that is composed of many HTL epitopes will induce a strong T-help immune response (see Example 2). If given in the same dose with any other vaccine formulation this will result in a stimulation of the immune response. Such a SAPN will be an adjuvant without the need of any CTL or B-cell epitope. However, B-cell and CTL epitopes can be combined with such an adjuvant SAPN. In addition particular adjuvant molecules can be covalently coupled to the SAPN as a substituent to the oligomerization domain D1 or D2 to further stimulate the adjuvant effect of the SAPN. Of particular interest are immunostimulatory nucleic acids, preferably an oligodeoxynucleotide containing deoxyinosine, an oligodeoxynucleotide containing deoxyuridine, an oligodeoxynucleotide containing a CG motif, an inosine and cytidine containing nucleic acid molecule. Other immunostimulatory molecules are, for example, antimicrobial peptides such as cationic peptides which are a class of immunostimulatory, positively charged molecules that are able to facilitate and/or improve adaptive immune responses. An example of such a peptide with immunopotentiating properties is the positively charged artificial antimicrobial peptide KLKLLLLLKLK (SEQ ID NO: 63), which induces potent protein-specific type-2 driven adaptive immunity after prime-boost immunizations.

Preferably, antigens of the invention are selected from the group consisting (a) proteins suited to induce an immune response against cancer cells; (b) proteins or carbohydrates suited to induce an immune response against infectious diseases; (c) proteins suited to induce an immune response against allergens; (d) peptide hormones suited to induce an immune response for the treatment of a human disease; and (e) hapten molecules suited to induce an immune response to treat addictions or other disorders. Peptidic nanoparticles comprising such proteins, peptidic fragments thereof, peptides, carbohydrates, or haptens may be suited to induce an immune response in humans, or also in farm animals and pets.

In one preferred embodiment of the invention, the antigens or antigenic determinants are the ones that are useful for the prevention of infectious disease. Such treatment will be useful to prevent a wide variety of infectious diseases affecting a wide range of hosts, e.g. humans or non-human animals, such as cow, sheep, pig, dog, cat, other mammalian species and non-mammalian species as well.

In particular the invention relates to SAPN comprising one of the following antigens:

(a) an antigen suited to induce an immune response against bacteria;

(b) an antigen suited to induce an immune response against viruses;

(c) an antigen suited to induce an immune response against parasites;

(d) an antigen suited to induce an immune response against cancer cells;

(e) an antigen suited to induce an immune response against allergens;

(f) an antigen suited to induce an immune response against addictions;

(g) an antigen suited to induce an immune response against diseases and metabolic disorders;

(h) an antigen suited to induce an immune response in a farm animals; and (i) an antigen suited to induce an immune response in a pet.

Treatable infectious diseases are well known to those skilled in the art. Examples include infections of viral, bacterial or parasitic etiology such as the following diseases: Amoebiasis, Anthrax, *Campylobacter* infections, Chickenpox, Cholera, Dengue, Diphtheria, Encephalitis, Ebola, Influenza, Japanese Encephalitis, Leishmaniasis, Malaria, Measles, Meningococcal Disease, Mumps, Nosocomial infections, Pertussis, Pneumococcal Disease, Polio (Poliomyelitis), Rubella, Shingles, Shistosomiasis, Tetanus, Tick-Borne Encephalitis, Trichomoniasis, Trypanosomiasis, Tuberculosis, Typhoid, Varicella, and Yellow Fever.

In particular the invention relates to SAPN comprising one of the following antigens from the following parasites:

*Campylobacter*, Cytomegalovirus, Epstein-Barr Virus, FMDV, *Haemophilus influenzae* Type b, *Helicobacter pylori*, Hepatitis B Virus, Hepatitis C Virus, Hepatitis E Virus, Herpes Simplex Virus, Human Immunodeficiency Virus, Human Papillomavirus, *Neisseria meningitides, Pseudomonas aeruginosa, Staphylococcus aureus, Streptococcus pneumoniae*, Respiratory Syncytial Virus, Rotavirus, Roundworm, Hookworm, and West Nile Virus.

In a preferred aspect of the invention, a composition for the prevention and treatment of malaria is envisaged (Example 11). The life cycle of the malaria parasite provides several stages at which interference could lead to cessation of the infective process. In the life cycle of the malaria parasite, a human becomes infected with malaria from the bite of a female *Anopheles* mosquito. The mosquito inserts its probe into a host and in so doing, injects a sporozoite form of *Plasmodium falciparum* (or vivax), present in the saliva of the mosquito. Possible protein and peptide sequences suitable for the design of a peptide vaccine may contain sequences from the following *Plasmodium* proteins: MSP-1 (a large polymorphic protein expressed on the parasite cell surface), MSA1 (major merozoite surface antigen 1), CS protein (native circumsporozoite), 35 KD protein or 55 KD protein or 195 KD protein according to U.S. Pat. No. 4,735,799, AMA-1 (apical membrane antigen 1), or LSA (liver stage antigen).

In a preferred design one of the B-cell epitopes is a sequence of 8 to about 48 residues that constitute a B cell epitope of the circumsporozoite (CS) protein. This B-cell epitope is a redundant repeat region of the amino acid sequence NANP for *Plasmodium falciparum*. In a preferred SAPN design this B cell epitope comprises two to about five repeats of the amino acid residue sequence NANP or the permutations thereof ANPN, NPNA, and PNAN. The corresponding repeat region in *Plasmodium vivax* is composed of any of the following highly similar sequences

TABLE 6

| Plasmodium vivax CS repeat B-cell epitope sequences | |
|---|---|
| Peptide | SEQ ID NO: |
| GDRAAGQPA | 65 |
| GDRADGQPA | 66 |
| GDRADGQAA | 67 |
| GNGAGGQPA | 68 |
| GDGAAGQPA | 69 |
| GDRAAGQAA | 70 |
| GNGAGGQAA | 71 |

In a preferred design one of the B-cell epitopes is a sequence of 8 to about 48 residues composed of any of these sequences.

Specific peptide sequences for the design of SAPN for the treatment of malaria are listed in the three tables below for B-cell epitopes, HTL-epitopes and CTL-epitopes.

The following Table 7 lists preferred *P. falciparum* coiled-coil B-cell epitopes (Villard V. et al., PLoS ONE 2007, 2(7): e645 and Agak G. W., Vaccine (2008) 26, 1963-1971. Since for B-cell epitopes only the surface accessible residues are of critical importance for their interactions with the B-cell receptor and the production of antibodies, the coiled-coil core residues at aa(a) and aa(d) positions, which are not surface exposed can be modified to some extent without changing the ability of the immunogen to elicit neutralizing antibodies. For example, exchanging a valine at an aa(a) position with an isoleucine will not affect the general immunological properties of the coiled-coil B-cell epitope. Therefore these coiled-coil sequences can be artificially stabilized by optimizing the core residues for best coiled-coil formation and stability (Example 13) without abolishing their immunological potential. Accordingly, modifications of these peptide B-cell epitopes at one or more of their core residues at aa(a) and/or aa(d) in line with the coiled-coil forming propensities as outlined in detail above are also envisioned for these B-cell epitopes.

Thus, in a preferred design, the coiled-coil B-cell epitope with modifications of one or more of their core positions is a peptide that contains at least a sequence which is two heptad-repeats long that is predicted by the coiled-coil prediction program COILS to form a coiled-coil with higher probability than 0.9 for all its amino acids with at least one of the window sizes of 14, 21, or 28.

In a more preferred design, the coiled-coil B-cell epitope with modifications of one or more of their core positions is a peptide that contains at least one sequence three heptad-repeats long that is predicted by the coiled-coil prediction program COILS to form a coiled-coil with higher probability than 0.9 for all its amino acids with at least one of the window sizes of 14, 21, or 28.

In another more preferred design, the coiled-coil B-cell epitope with modifications of one or more of their core positions is a peptide that contains at least two separate sequences two heptad-repeats long that are predicted by the coiled-coil prediction program COILS to form a coiled-coil with higher probability than 0.9 for all its amino acids with at least one of the window sizes of 14, 21, or 28.

TABLE 7

| Plasmodium falciparum coiled-coil B-cell epitope sequences | |
|---|---|
| B-cell epitope | SEQ ID NO: |
| IKTMNTQISTLKNDVHLLNEQIDKLNNEKGTLNSKISE LNVQIMDL | 72 |
| LLSKDKEIEEKNKKIKELNNDIKKL | 73 |
| ICSLTTEVMELNNKKNELIEENNKLNLVDQGKKKLKKD VEKQKKEIEKL | 74 |
| VDKIEEHILDYDEEINKSRSNLFQLKNEICSLTTEVME LNNKKNELIEENNKLNLVDQGKKKLKKDVEKQKKEIEKL | 75 |
| LDENEDNIKKMKSKIDDMEKEIKYR | 76 |
| GMNNMNGDINNIN(GDINNMN)$_4$ | 77 |
| KKRNVEEELHSLRKNYNIINEEIEEIT | 78 |
| EEIKEEIKEVKEEIKEVKEEIKEVKEEIKEVKEEIKE | 79 |
| KNDINVQLDDINVQLDDINVQLDDINIQLDEINLN | 80 |
| KIQIEEIKKETNQINKDIDHIEMNIINLKKKIEF | 81 |
| DSMNNHKDDMNNYNDNINNYVESMNNYDDIMNK | 82 |
| MCELNVMENNMNNIHSNNNNISTHMDDVIE | 83 |
| KEIQMLKNQILSLEESIKSLNEFINNLKN | 84 |
| GGLKNSNHNLNNIEMKYNTLNNNMNSINK | 85 |
| EKLKKYNNEISSLKKELDILNEKMGKCT | 86 |
| EKMNMKMEQMDMKMEKIDVNMDQMDVKMEQMDVKMEQM DVKMKRMNK | 87 |
| KNKLNKKWEQINDHINNLETNINDYNKKIKEGDSQLNN IQLQCENIEQKINKIKE | 88 |
| NEMNKEVNKMNEEVNKMNEEVNKMNEEVNKMNKEVNKM DEEVNKMNKEVNKMNK | 89 |
| QNKMENDMNIIKNDMNIMENDMNIMENDMNIIKNDMNI MEKDMNIIKNDMNIIKNNMNIIKNEMNIIKNV | 90 |
| TKKLNKELSEGNKELEKLEKNIKELEETNNTLENDIKV | 91 |
| ENINNMDEKINNVDEQNNNMDEKINNVDEKK | 92 |
| ARDDIQKDINKMESELINVSNEINRLD | 93 |
| EKKLDILKVNISNINNSLDKLK | 94 |
| NSLDYYKKVIIKLKNNINNMEEYTNNITNDINVLKA HID | 95 |
| PDFDAYNEKLGSISQSIDEIKKKIDNLQKEIKVANK | 96 |
| QLEEKTKQYNDLQNNMKTIKEQNEHLKNKFQSMGK | 97 |
| IIDIKKHLEKLKIEIKEKKEDLENL | 98 |

The following Table 8 lists preferred *P. falciparum* HTL epitopes (Doolan, D. L., The Journal of Immunology, 2000, 165: 1123-1137; U.S. Pat. No. 5,114,713)

TABLE 8

| *Plasmodium falciparum* HTL epitope sequences | | |
|---|---|---|
| Protein | HTL Epitope | SEQ ID NO: |
| CSP-2 | MRKLAILSVSSFLFV | 99 |
| LSA-13 | LVNLLIFHINGKIIKNS | 100 |
| CSP-53 | MNYYGKQENWYSLKK | 101 |
| SSP2-61 | RHNWVNHAVPLAMKLI | 102 |
| SSP2-223 | VKNVIGPFMKAVCVE | 103 |
| CSP-375 | SSVFNVVNSSIGLIM | 104 |
| EXP-82 | AGLLGNVSTVLLGGV | 105 |
| EXP-71 | KSKYKLATSVLAGLL | 106 |
| SSP2-527 | GLAYKFVVPGAATPY | 107 |
| SSP2-62 | HNWVNHAVPLAMKLI | 108 |
| SSP2-509 | KYKIAGGIAGGLALL | 109 |
| CSP | EKKIAKMEKASSVFNVV | 110 |
| CSP | EYLNKIQNSLSTEWSPCSVT | 111 |

The following Table 9 lists preferred *P. falciparum* CTL epitopes (U.S. Pat. Nos. 5,028,425, 5,972,351, 6,663,871)

TABLE 9

| *Plasmodium falciparum* CTL epitope sequences | | |
|---|---|---|
| CTL epitope | HLA-restriction | SEQ ID NO: |
| KPNDKSLY | B35 | 112 |
| KPKDELDY | B35 | 113 |
| KPIVQYDNF | B35 | 114 |
| ASKNKEKALII | B8 | 115 |
| GIAGGLALL | A2.1 | 116 |
| MNPNDPNRNV | B7 | 117 |
| MINAYLDKL | A2.2 | 118 |
| ISKYEDEI | B17 | 119 |
| HLGNVKYLV | A2.1 | 120 |
| KSLYDEHI | B58 | 121 |
| LLMDCSGSI | A2.2 | 122 |
| KSKDELDY | B35 | 123 |
| IPSLALMLI | unknown | 124 |
| MPLETQLAI | unknown | 125 |
| MPNDPNRNV | B7 | 126 |
| YLNKIQNSL | A2.1 | 127 |
| MEKLKELEK | B8 | 128 |
| ATSVLAGL | B58 | 129 |

In another preferred aspect of the invention, a composition for the prevention and treatment of HIV is envisaged (Examples 5 and 12). For the preparation of an anti-HIV vaccine a synthetic peptide capable of eliciting HIV-specific antibodies may be used, said synthetic peptide having the amino acid sequence of a functional T-cell epitope or B-cell epitope of an envelope or gag protein or gp120 or gp41 of HIV-1 to provide an immune response. Of special interest are sequences within gp41 or gp120, which can induce conformation specific neutralizing antibodies able to interfere with the fusion process like the known antibodies 2F5 and 4E10 or from the V3-loop of gp41 or gp120. Such sequences are mainly localized in and around the HR1 and HR2 and the cluster I and cluster II regions. Antibodies binding to e.g. the coiled-coil trimer of gp41 and elicited by peptidic nanoparticles of the invention incorporating this coiled-coil trimer will inhibit hairpin formation and hence viral fusion. Similarly, antibodies raised against the trimeric coiled-coil of Ebola or of another virus with a similar fusion process will inhibit viral entry of these viruses.

Using the highly conserved HIV protein sequences as described in Letourneau S. et al., PLoS ONE 2007, 10:e984, CTL epitopes were predicted using SVRMHCdb (Wan J. et al., BMC Bioinformatics 2006, 7:463). These conserved protein sequences contain CTL epitopes predicted to bind to the HLA molecules as listed in Table 10 and are preferred CTL epitopes for the design of an SAPN-HIV vaccine. These peptide epitopes contain largely overlapping sequences that can be combined to longer peptide sequences that harbor multiple CTL epitopes in one single continuous peptide string (Table 11).

TABLE 10

| Conserved predicted HIV CTL epitopes | | |
|---|---|---|
| CTL-Epitope | SEQ ID NO: | HLA restriction |
| PLDEGFRKY | 130 | A*0101 |
| LLQLTVWGI | 131 | A*0201 |
| YTAFTIPSI | 132 | A*0202 |
| GLNKIVRMY | 133 | A*0203 |
| ILKDPVHGV | 134 | A*0204 |
| YTAFTIPSI | 135 | A*0206 |
| IIGRNLLTQI | 136 | A*0207 |
| KGPAKLLWK | 137 | A*0301 |
| VLFLDGIDK | 138 | A*0302 |
| AVFIHNFKR | 139 | A*1101 |
| HNFKRKGGI | 140 | A*3101 |
| IVWQVDRMR | 141 | A*3301 |
| SDIKVVPRR | 142 | A*6801 |
| YTAFTIPSI | 143 | A*6802 |
| LGIPHPAGL | 144 | B*0702 |
| FSVPLDEGF | 145 | B*3501 |
| AVFIHNFKR | 146 | A11 |
| RWIILGLNK | 147 | A24 |
| AIFQSSMTK | 148 | A3 |
| AVFIHNFKR | 149 | A31 |

TABLE 10-continued

Conserved predicted HIV CTL epitopes

| CTL-Epitope | SEQ ID NO: | HLA restriction |
|---|---|---|
| AVFIHNFKR | 150 | A68 |
| WQVMIVWQV | 151 | B35 |
| YSPVSILDI | 152 | B51 |
| APRKKGCWK | 153 | B7 |
| LKDPVHGVY | 154 | A*0101 |
| YTAFTIPSI | 155 | A*0201 |
| TLNFPISPI | 156 | A*0203 |
| FKRKGGIGG | 157 | A*0204 |
| LLQLTVWGI | 158 | A*0206 |
| EILKDPVHGV | 159 | A*0207 |
| GIPHPAGLK | 160 | A*0301 |
| GPAKLLWKG | 161 | A*1101 |
| SQGIRKVLF | 162 | A*3101 |
| SDLEIGQHR | 163 | A*6801 |
| LVSQGIRKV | 164 | A*6802 |
| QGIRKVLFL | 165 | B*0702 |
| EEAELELAE | 166 | B*3501 |
| FTIPSINNE | 167 | B*5301 |
| FKRKGGIGG | 168 | B*5401 |
| KGPAKLLWK | 169 | A11 |

TABLE 10-continued

Conserved predicted HIV CTL epitopes

| CTL-Epitope | SEQ ID NO: | HLA restriction |
|---|---|---|
| LLTQIGCTL | 170 | A2 |
| KGPAKLLWK | 171 | A3 |
| YTAFTIPSIN | 172 | A68 |
| LYVGSDLEI | 173 | B35 |
| LLTQIGCTL | 174 | B51 |
| DFWEVQLGI | 175 | A*0201 |
| LLWKGEGAV | 176 | A*0202 |
| MIVWQVDRM | 177 | A*0203 |
| FPISPIETV | 178 | A*0204 |
| AGLKKKKSV | 179 | A*0206 |
| APRKKGCWK | 180 | A*0301 |
| ISPIETVPV | 181 | B*0702 |
| WEVQLGIPH | 182 | B*5401 |
| AIFQSSMTK | 183 | A11 |
| GIPHPAGLK | 184 | A3 |
| AELELAENR | 185 | A31 |
| SDIKVVPRR | 186 | A68 |
| LTEEAELEL | 187 | B35 |
| SPAIFQSSM | 188 | B7 |

TABLE 11

Conserved combined predicted HIV CTL epitopes

| Peptide | SEQ ID NO: | HLA-restriction |
|---|---|---|
| PLDEGFRKYTAFTIPSINNE | 189 | A*0101, A*0201, A*0202, A*0206, A*6802, B*3501, B*5301, A68 |
| AVFIHNFKRKGGIGG | 190 | A*3101, A*1101, A11, A31, A68, B*5401, A*0204 |
| IIGRNLLTQIGCTLNFPISPIETVPV | 191 | A*0207, B51, A2, B*0702, A*0204, A*0203 |
| DFWEVQLGIPHPAGLKKKKSV | 192 | A*0201, B*0702, A*0301, A*0206, B*5401, A3 |
| LTEEAELELAENREILKDPVHGV | 193 | A31, B35, B*3501, A*0204, A*0101 |
| KGPAKLLWKGEGAV | 194 | A*0202, A*1101, A*0301, A11, A3 |
| LVSQGIRKVLFLDGIDK | 195 | A*0302, A*3101, A*6801, B*0702 |
| RWIILGLNKIVRMYSPVSILDI | 196 | A24, A*0203, B51 |
| WQVMIVWQVDRMR | 197 | A*3301, B35, A*0203 |
| SPAIFQSSMTK | 198 | A3, A11, B7 |
| SDIKVVPRR | 199 | A*6801, A68 |
| LLQLTVWGI | 200 | A*0202, A*0206 |

TABLE 11-continued

| Conserved combined predicted HIV CTL epitopes | | |
|---|---|---|
| Peptide | SEQ ID NO: | HLA-restriction |
| APRKKGCWK | 201 | A*0301, B7 |
| LYVGSDLEIGQHR | 202 | A*6801, B35 |

In another preferred aspect of the invention, a composition for the prevention and treatment of influenza is envisaged. Influenza A encodes an integral membrane protein, M2, a homotetramer, the subunit of which has a small external domain (M2e) of 23 amino acid residues. The natural M2 protein is present in a few copies in the virus particle and hidden to the immune system by the bulky other two surface proteins hemagglutinin and sialidase. On the other hand it exists in abundance on the membrane surface of virus-infected cells. The sequence of M2e is highly conserved. It has been shown that M2e presented to the immune system as a tetramer in a chimeric GNC4-M2e protein, generates a highly specific and protective humoral immune response (DeFilette M. et al., J Biol Chem 2008; 283(17):11382-11387).

The M2e tetramer is a highly conserved B-cell epitope for both, human and avian specific influenza strains (Table 12 and 13). In a preferred embodiment of this invention it can be displayed in its native tetrameric conformation when attached to the N-terminus of the tetrameric coiled-coil from tetrabrachion—or any other tetrameric coiled-coil—of the SAPN (Example 9).

TABLE 12

| M2e human-specific M2e sequences | | | | |
|---|---|---|---|---|
| Representative Strain | Subtype | Host | Amino acid Sequence | SEQ ID NO: |
| A/New Caledonia/20/99 | H1N1 | human | SLLTEVETPIRNEWGCRCNDSSDP | 203 |
| A/Aichi/470/68 | H3N1 | human | SLLTEVETPIRNEWGCRCNDSSDP | 203 |
| A/Ann arbor/6/60 | H2N2 | human | SLLTEVETPIRNEWGCRCNDSSDP | 203 |
| A/Berkeley/1/68 | H2N2 | human | SLLTEVETPIRNEWGCRCNDSSDP | 203 |
| A/Puerto Rico/8/34 | H1N1 | human | SLLTEVETPIRNEWGCRCN**G**SSDP | 204 |
| A/Wisconsin/3523/88 | H1N1 | human | SLLTEVETPIRNEWGC**K**CNDSSDP | 205 |
| A/Hebei/19/95 | H3N2 | human | SLLTEVETPIRNEWECRCN**G**SSDP | 204 |
| A/Viet Nam/1203/2004 | H5N1 | human | SLLTEVETPTRNEWECRCSDSSDP | 206 |
| A/Hong Kong/156/97 | H5N1 | human | SLLTEVET**L**TRN**G**W**G**CRCSDSSDP | 207 |
| A/Hong Kong/1073/99 | H9N2 | human | SLLTEVET**L**TRN**G**WEC**K**C**R**DSSDP | 208 |

TABLE 13

| M2e avian-specific M2e sequences | | | | |
|---|---|---|---|---|
| Representative Strain | Subtype | Host | Amino acid Sequence | SEQ ID NO: |
| A/Chicken/Nakorn-Patom/Thailand | H5N1 | avian | SLLTEVETPTRNEWECRCSDSSDP | 206 |
| A/Thailand/1(KAN-1)/04 | H5N1 | avian | SLLTEVETPTRNEWECRCSDSSDP | 206 |
| A/Duck/1525/81 | H5N1 | avian | SLLTEVETPTRN**G**WEC**K**CSDSSDP | 209 |
| A/Chicken/New York/95 | H7N2 | avian | SLLTEVETPTRN**G**WEC**K**CSDSSDP | 209 |
| A/Chicken/Hong Kong/G9/97 | H9N2 | avian | SLLTEVETPTRN**G**W**G**CRCS**G**SSDP | 210 |

Influenza hemagglutinin (HA) is activated by cleavage of the precursor protein into two separate peptide chains (Steinauer D. S. et al., Virology 1999; 258:1-20). Cleavage of the HA precursor molecule HA0 is required to activate virus infectivity, and the distribution of activating proteases in the host is one of the determinants of tropism and, as such, pathogenicity. The HAs of mammalian and nonpathogenic avian viruses are cleaved extracellularly, which limits their spread in hosts to tissues where the appropriate proteases are encountered. On the other hand, the HAs of pathogenic viruses are cleaved intracellularly by ubiquitously occurring proteases and therefore have the capacity to infect various cell types and cause systemic infections.

In contrast to the M2e sequence, the N-terminal part of the cleavage peptide is not highly conserved (the C-terminal portion of the cleavage peptide is in fact highly conserved). In the HA precursor protein the cleavage peptide is surface exposed and the six residues (three residues on each side of the cleavage site) around the cleavage site are the most characteristic of this peptide sequence (highlighted in bold in Table 14). In a preferred SAPN design, these six residues represent the B-cell epitope, which can induce antibodies that, upon binding to the peptide, can protect the HA precursor protein from getting cleaved.

The SAPN are ideally suited to display a multitude of different cleavage sequences specific for the different HA types (Table 14) by co-assembling peptides that have the same SAPN-forming core D1-L-D2 but different B-cell epitopes attached to it (Example 15).

TABLE 14

Hemagglutinin cleavage site sequences from influenza A and influenza B

| Type | Sequence | SEQ ID NO: |
|---|---|---|
| H1 | SI**QSRGLF**GA | 211 |
| H2 | QI**ESRGLF**GA | 212 |
| H3 | ER**QTRGIF**GA | 213 |
| H4 | EK**ATRGLF**GA | 214 |
| H5 Consensus 1 | KR**KTRGLF**GA | 215 |
| H5 Consensus 2 | RR**KKRGLF**GA | 216 |
| H6 | QI**ATRGLF**GA | 217 |
| H7 Consensus 1 | IP**KGRGLF**GA | 218 |
| H7 Consensus 2 | KK**KGRGLF**GA | 219 |
| H7 Consensus 3 | KR**EKRGLF**GA | 220 |
| H8 | SI**EPKGLF**GA | 221 |
| H9 | AA**SYRGLF**GA | 222 |
| H10 | II**QGRGLF**GA | 223 |
| H11 | AI**ATRGLF**GA | 224 |
| H13 | AI**SNRGLF**GA | 225 |
| B | LL**KERGFF**GA | 226 |

For example a hemagglutinin B-cell epitope string comprising the sequences of H1, H2, and H3 cleavage sites with an inserted aspartate amino acid to make the sequence more soluble and less basic would look like this: SIQSRGLFGDIESRGLFGERQTRGIFG (SEQ ID NO:227).

Peptides with the same core sequence but different B-cell epitopes or epitope strings can be co-assembled into a single SAPN to generate a multivalent SAPN immunogen that possibly includes all or the most important (H1, H2, H3, H5, H7 and H9 for a human vaccine) sequences of Table 14 (Example 15).

In a similar approach an Influenza vaccine SAPN composed of six peptide chains with an identical core and identical N-terminal B-cell epitope M2e and about 20 CTL epitopes at the C-terminus (three or four each per peptide chain) can be co-assembled into a single SAPN (Example 14). In Table 15 preferred conserved CTL epitopes from Parida R. et al., Vaccine 2007, 25:7530-7539 are listed. Since the core of these six peptide chains is identical, co-assembly of these six peptide chains into one single SAPN allows the incorporation of about 20 different CTL epitopes into one single SAPN.

TABLE 15

Conserved influenza CTL epitopes from Parida R. et al.

| Protein name | Peptides | SEQ ID NO: | HLA restriction |
|---|---|---|---|
| Matrix protein1 | IRHENRMVL | 228 | B 2705 |
| Matrix protein1 | QAYQKRMGV | 229 | B 5101 |
| Nonstructural protein 1 | LKMPASRYL | 230 | Cw 0301 |
| Nonstructural protein 1 | SRYLTDMTL | 231 | B 2705 |
| Nonstructural protein 1 | FMLMPKQKV | 232 | A 0201 |
| Nonstructural protein 2 | MRMGDFHSL | 233 | B 2705 |
| Nonstructural protein 2 | MRMGDFHSL | 233 | Cw 0301 |
| Polymerase | YLLAWKQVL | 234 | A 0201 |
| Polymerase | APIEHIASM | 235 | Cw 0401 |
| Polymerase | RRNYFTAEV | 236 | B 2705 |

TABLE 15-continued

Conserved influenza CTL epitopes from Parida R. et al.

| Protein name | Peptides | SEQ ID NO: | HLA restriction |
|---|---|---|---|
| Nucleocapsid protein | IQMCTELKL | 237 | B 2705 |
| Nucleocapsid protein | AAGAAVKGV | 238 | B 5101 |
| Nucleocapsid protein | VGTMVMELI | 239 | B 5101 |
| Polymerase basic protein 1 | NPTLLFLKV | 240 | B 5101 |
| Polymerase basic protein 1 | RLIDFLKDV | 241 | A 0201 |
| Polymerase basic protein 1 | MQIRGFVYF | 242 | B 2705 |
| Polymerase basic protein 1 | IMFSNKMAR | 243 | B 2705 |
| Polymerase basic protein 1 | MFSNKMARL | 244 | Cw 0401 |
| Polymerase basic protein 2 | ERNEQGQTL | 245 | B 2705 |
| Polymerase basic protein 2 | VAYMLEREL | 246 | B 5101 |
| Polymerase basic protein 2 | LRHFQKDAK | 247 | B 2705 |
| Polymerase basic protein 2 | VRDQRGNVL | 248 | B 2705 |

In another preferred embodiment, the compositions of the invention are immunotherapeutics that may be used for the treatment of metabolic disorders and diseases, or addictions. Most preferred are immunotherapeutics for the treatment of Alzheimer disease, hypertension, obesity, nicotine- and cocaine addictions.

TABLE 16

B cell epitopes for SAPN vaccines

| Target antigen | Indication(s) |
|---|---|
| Nicotine | Nicotine addiction |
| Cocaine | Cocaine addiction |
| Aβ-fragment (Aβ) | Alzheimer's disease |
| angiotensin I/II (ATII/I) | Hypertension |
| cholesterol ester transfer protein (CETP) | Hyperlipidemia |
| human chorionic gonadotropin (hCG) | Fertility management |
| epidermal growth factor (EGF) | NSC-lung cancer |
| follicle stimulating hormone (FSH) | Fertility management |
| gastrin | Pancreatic cancer |
| ghrelin | Obesity |
| gonadotropin releasing hormone (GnRH) | Fertility management |
| gonadotropin releasing hormone (GnRH) | Prostate cancer |
| Her2 | Breast cancer |
| IgE | Allergic asthma |
| IL-1βb | rheumatoid arthritis |
| interferon α (IFNα) | HIV/AIDs |
| mucin | Cancer |
| tumor necrosis factor α (TNFα) | Psoriasis |
| tumor necrosis factor α (TNFα) | Arthritis |
| RANKL | Osteoporosis |
| IL-17 | Multiple sclerosis |

The Aβ-fragment (Aβ) is a 42 amino acid long peptide (Aβ1-42). Since the whole 42 residue long peptide sequence also contains CTL epitopes that can cause autoimmune reactions, it is desirable to use only shorter fragments of this peptide for vaccine design, such as Aβ1-12 or even such short peptides as Aβ1-6 (U.S. Pat. No. 7,279,165).

Likewise, the full-length TNFα protein as an immunogen has some limitations. Local overproduction of the proinflammatory cytokine TNFα is critically involved in the pathogenesis of several chronic inflammatory disorders, including rheumatoid arthritis, psoriasis, and Crohn's disease. Neutralization of TNFα by monoclonal antibodies (mAbs, infliximab, adalimumab) or chimeric soluble receptors (etanercept) is efficacious in the treatment of these conditions but has several potential drawbacks. It may induce allotype- or Id-specific Abs, which might limit long-term efficacy in many patients. Moreover, as the number of treated patients increases, it is becoming evident, that treatment with TNFα-antagonists, in particular mAbs, increases the risk of opportunistic infections, especially those caused by intracellular pathogens like *Mycobacterium tuberculosis, Listeria monocytogenes*, or *Histoplasma capsulatum*. Immunization with shorter fragments of TNFα comprising only residues 4-23 has been shown to avoid some of these problems (G. Spohn et al., The Journal of Immunology, 2007, 178: 7450-7457). Therefore, immunization with TNFα4-23 is a novel efficient therapy for rheumatoid arthritis and other autoimmune disorders, which adds a new level of safety to the existing anti-TNFα therapies. By selectively targeting only the soluble form of TNFα and sparing the transmembrane form, pathogenic effects of TNFα are neutralized by the vaccine, while important functions in the host response to intracellular pathogens remain intact.

Apart from nicotine and cocaine also the following compounds may be used as hapten molecules the design of a B-cell SAPN vaccine for addictions: opiates, marijuana, amphetamines, barbiturates, glutethimide, methyprylon, chloral hydrate, methaqualone, benzodiazepines, LSD, anticholinergic drugs, antipsychotic drugs, tryptamine, other psychomimetic drugs, sedatives, phencyclidine, psilocybine, volatile nitrite, and other drugs inducing physical dependence and/or psychological dependence.

In another preferred embodiment, the compositions of the invention are immuno-therapeutics that may be used for the treatment of allergies. The selection of antigens or antigenic determinants for the composition and the method of treatment for allergies would be known to those skilled in the medical art treating such disorders. Representative examples of this type of antigen or antigenic determinant include bee venom phospholipase A2, Bet v I (birch pollen allergen), 5 Dol m V (white-faced hornet venom allergen), and Der p I (House dust mite allergen).

In another preferred embodiment, the compositions of the invention are immuno-therapeutics that may be used for the treatment of cancer. Major cancers for targeted vaccines design are the following: Brain Cancer, Breast Cancer, Cervical Cancer, Colorectal Cancer, Esophageal Cancer, Glioblastoma, Leukemia (acute Myelogenous and chronic Myeloid), Liver cancer, Lung Cancer (Non-Small-Cell Lung Cancer, Small-Cell Lung Cancer), Lymphoma (Non-Hodgkin's Lymphoma), Melanoma, Ovarian Cancer, Pancreatic Cancer, Prostate Cancer, Renal Cancer.

The selection of antigens or antigenic determinants for the composition and method of treatment for cancer would be known to those skilled in the medical art treating such disorders. Representative examples of this type of antigen or antigenic determinant include the following: HER2/neu (breast cancer), GD2 (neuroblastoma), EGF-R (malignant glioblastoma), CEA (medullary thyroid cancer), CD52 (leukemia), MUC1 (expressed in hematological malignancies), gp100 protein, or the product of the tumor suppressor gene WT1. In Table 17 cancer specific T-cell epitopes of interest are shown with the relevant protein of origin and the MHC restriction.

TABLE 17

Cancer T-cell epitopes for SAPN vaccines

| Peptide Sequence | Protein | MCH Restriction | SEQ ID NO: |
|---|---|---|---|
| KCDICTDEY | Tyrosinase | A1 | 249 |
| YMDGTMSQV | Tyrosinase | A2 | 250 |
| MLLAYLYQL | Tyrosinase | A2 | 251 |
| AFLPWHRLF, AFLPWHRLFL | Tyrosinase | A24 | 252 253 |
| SEIWRDIDF | Tyrosinase | B44 | 254 |
| YLEPGPVTA | gp100/pMEL17 | A2 | 255 |
| KTWGQYWQV | gp100/pMEL17 | A2 | 256 |
| ITDQVPFSV | gp100/pMEL17 | A2 | 257 |
| VLYRYGSFSV | gp100/pMEL17 | A2 | 258 |
| LLDGTATLRL | gp100/pMEL17 | A2 | 259 |
| ALLAVGATK | gp100/pMEL17 | A3 | 260 |
| MLGTHTMEV | gp100/pMEL17 | A3 | 261 |
| LIYRRRLMK | gp100/pMEL17 | A3 | 262 |
| ALNFPGSQK | gp100/pMEL17 | A3 | 263 |
| AAGIGILTV | MART-1/MelanA | A2 | 264 |
| ILTVILGVL | MART-1/MelanA | A2 | 265 |
| MSLQRQFLR | gp75/TRP-1 | A31 | 266 |
| SVYDFFVWL | TRP-2 | A2 | 267 |
| LLGPGRPYR | TRP-2 | A31, A33 | 268 |
| YLSGANLNL | CEA | A2 | 269 |
| KIFGSLAFL | HER-2/neu | A2 | 270 |
| VMAGVGSPYV | HER-2/neu | A2 | 271 |
| IISAVVGIL | HER-2/neu | A2 | 272 |
| LLHETDSAV | PSMA | A2 | 273 |
| ALFDIESKV | PSMA | A2 | 274 |
| EADPTGHSY | MAGE-1 | A1 | 275 |
| SLFRAVITK | MAGE-1 | A3 | 276 |
| SAYGEPRKL | MAGE-1 | Cw*1601 | 277 |
| KMVELVHFL | MAGE-2 | A2 | 278 |

TABLE 17-continued

Cancer T-cell epitopes for SAPN vaccines

| Peptide Sequence | Protein | MCH Restriction | SEQ ID NO: |
|---|---|---|---|
| YLQLVFGIEV | MAGE-2 | A2 | 279 |
| EVDPIGHLY | MAGE-3 | A1 | 280 |
| FLWGPRALV | MAGE-3 | A2 | 281 |
| MEVDPIGHLY | MAGE-3 | B44 | 282 |
| AARAVFLAL | BAGE | Cw*1601 | 283 |
| YRPRPRRY | GAGE-1,2 | Cw6 | 284 |
| VLPDVFIRC | GnT-V | A2 | 285 |
| QLSLLMWIT | NY-ESO-1 | A2 | 286 |
| SLLMWITQC | NY-ESO-1 | A2 | 287 |
| ASGPGGGAPR | NY-ESO-1 | A31 | 288 |
| QDLTMKYQIF | 43 kD protein | A2 | 289 |
| AYGLDFYIL<br>EAYGLDFYIL | p15 | A24 | 290<br>291 |
| SYLDSGIHF | Mutated beta-catenin | A24 | 292 |
| ETVSEQSNV | Mutated elongation factor 2 | A*6802 | 293 |
| FPSDSWCYF | Mutated CASP-8 (FLICE/MACH) | B35.3 | 294 |
| EEKLIVVLF | MUM-1 gene product mutated across intron/exon junction | B*4402 | 295 |

Most preferred are the coiled-coil sequences, B-cell-, HTL- and CTL-epitopes, monomeric building blocks, SAPN, and vaccine designs described in the examples.

EXAMPLES

The following examples are useful to further explain the invention but in no way limit the scope of the invention.

Example 1

PADRE (P5c-8-Mal)

The pan-DR epitope PADRE with the sequence AKFVAAWTLKAAA (SEQ ID NO:296) is incorporated into the trimeric coiled-coil of the SAPN by using the following design criteria: The residue alanine (A) has a strong tendency to form alpha-helices. The alignment with coiled-coil core positions is such that the residues valine, tryptophan and alanine are at an aa(a), aa(d) and again an aa(a) position of the heptad repeat pattern. The remaining part of the trimeric coiled-coil N-terminal and C-terminal to the HTL epitope is designed such that the sequence is predicted to from a very strong coiled-coil.

The sequence of this peptide (SEQ ID NO:7) is predicted to form a coiled-coil by the prediction program COILS. The coiled-coil forming probability is more than 95% for all the residues in the sequence using a window of 21 amino acids for the coiled-coil prediction (see Table 18 below). Hence this is a predicted coiled-coil that also contains a T-cell epitope.

It is very important to realize that if the window comprises only 14 amino acids, the coiled-coil prediction drops to very low values of less than 2% probability within the sequence of the T-cell epitope. The larger window size of 21 amino acids with its high predicted coiled-coil propensities throughout the sequence shows the effect of the flanking regions at the N- and C-terminal ends of the T-cell epitope. If these are sequences that strongly favor coiled-coil formation then the less favorable coiled-coil propensity of the T-cell epitope may be compensated and the whole sequence will be induced to form a coiled-coil even though the T-cell epitope does not contain a very favorable coiled-coil sequence.

```
RLLARLEELERRLEEL_AKFVAAWTLKAAA_VDLELAALRRRLEELAR   (SEQ ID NO: 7)

 d   a   d   a   d   a   d   a   d   a   d   a   d    core residues
```

TABLE 18

| Coiled-coil propensity of SEQ ID NO: 7 comprising the PanDR epitope PADRE | | |
|---|---|---|
| Amino acid | Window 14 | Window 21 |
| R | 1.000 | 0.997 |
| L | 1.000 | 0.997 |
| L | 1.000 | 0.997 |
| A | 1.000 | 0.997 |
| R | 1.000 | 0.997 |
| L | 1.000 | 0.997 |
| E | 1.000 | 0.997 |
| E | 1.000 | 0.997 |
| L | 1.000 | 0.997 |
| E | 1.000 | 0.997 |
| R | 1.000 | 0.997 |
| R | 1.000 | 0.997 |
| L | 1.000 | 0.997 |
| E | 1.000 | 0.997 |
| E | 1.000 | 0.997 |
| L | 1.000 | 0.997 |
| A | 1.000 | 0.997 |
| K | 1.000 | 0.997 |
| F | 0.970 | 0.997 |
| V | 0.911 | 0.997 |
| A | 0.710 | 0.997 |
| A | 0.356 | 0.992 |
| W | 0.062 | 0.961 |
| T | 0.018 | 0.961 |
| L | 0.034 | 0.956 |
| K | 0.156 | 0.986 |
| A | 0.156 | 0.986 |
| A | 0.336 | 0.986 |
| A | 0.649 | 0.986 |
| V | 0.902 | 0.986 |
| D | 0.992 | 0.986 |
| L | 0.992 | 0.986 |
| E | 0.999 | 0.986 |
| L | 0.999 | 0.986 |
| A | 0.999 | 0.986 |
| A | 0.999 | 0.986 |
| L | 0.999 | 0.986 |
| R | 0.999 | 0.986 |
| R | 0.999 | 0.986 |
| R | 0.999 | 0.986 |
| L | 0.999 | 0.986 |
| E | 0.999 | 0.986 |
| E | 0.999 | 0.986 |
| L | 0.999 | 0.986 |
| A | 0.999 | 0.986 |
| R | 0.999 | 0.986 |

This trimeric coiled-coil of SEQ ID NO:7 was then included in the SAPN sequence of SEQ ID NO:8 below, which is composed of a His-tag, the pentameric coiled-coil of COMP, the trimeric coiled-coil composed of the sequence of SEQ ID NO:7 comprising the PADRE T-cell epitope, and the B-cell epitope from the CS-protein of *Plasmodium berghei*.

(SEQ ID NO: 8)
MGHHHHHHGDWKWDGGLVPRGSDEMLRELQETNAALQDVRELLRQQVKQI

TFLRALLMGGRLLARLEELERRLEEL*AKFVAAWTLKAAA*VDLELAALRRR

LEELARGGSGDPPPPNPNDPPPPNPND

Figure 4:
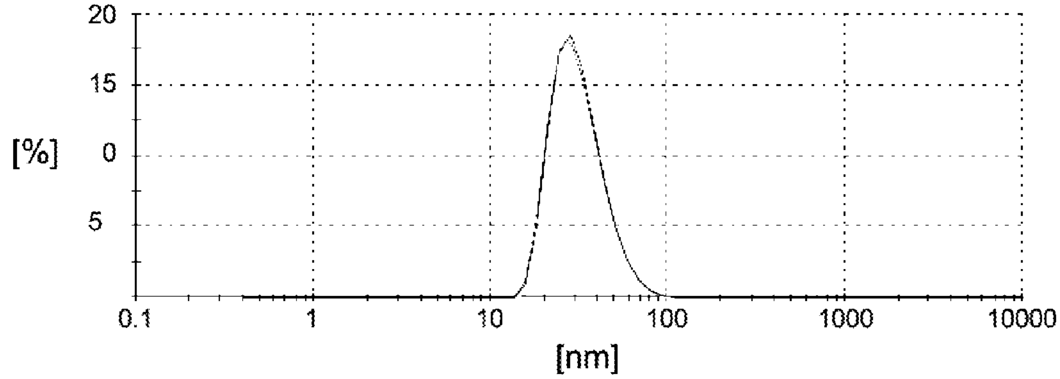
FIG. 4: Dynamic lights scattering (DLS, A) and transmission electron microscopy (TEM, B) of the self-assembled peptide nanoparticles formed from peptides with the sequence SEQ ID NO:8, Example 1. The DLS analysis shows size distribution with an average particle diameter of 32.01 nm and polydispersity index of 12.9% (A). The TEM pictures (B) show nanoparticles of the same size as determined by DLS.
Figure 4:
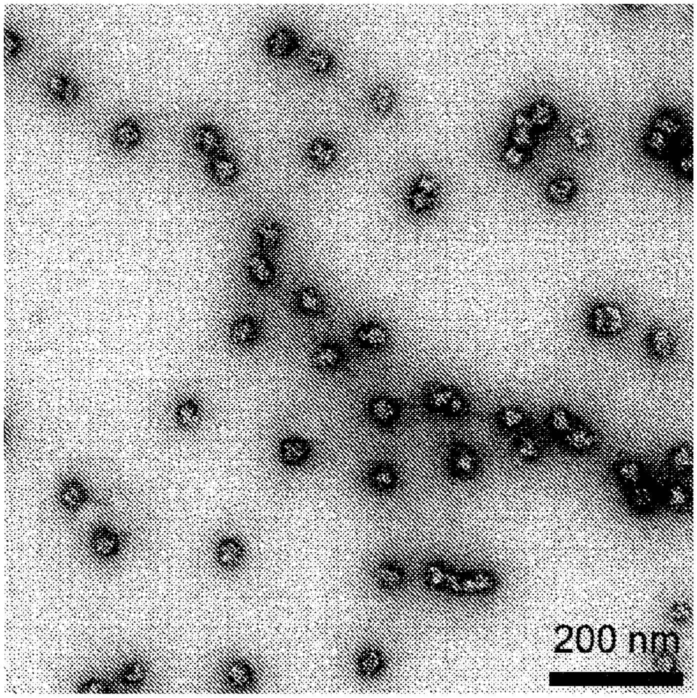

The peptide with this sequence was expressed in *E. coli* and purified on a nickel affinity column by standard biotechnology procedures. The refolding was performed according to Raman S. et al., Nanomedicine: Nanotechnology, Biology, and Medicine 2 (2006) 95-102. The refolded SAPN were analyzed for nanoparticle formation by dynamic light scattering (DLS) techniques and transmission electron microscopy (TEM). The DLS analysis showed a nice size distribution with an average particle diameter of 32.01 nm and polydispersity index of 12.9% (FIG. 4A). The TEM pictures (FIG. 4B) show nanoparticles of the same size as determined by DLS.

Example 2

P5c-6-General

This coiled-coil sequence contains four overlapping HTL epitopes with the sequences LEELERSIW (residues 6-14 of SEQ ID NO:9), IWMLQQAAA (residues 13-21 of SEQ ID NO:8), WMLQQAAR (residues 14-22 of SEQ ID NO:9), and MLQQAAARL (residues 15-23 of SEQ ID NO:9) that are predicted by the algorithm SVRMHC to bind to the different MHC II molecules DQA1*0501, DRB1*0501, DRB5*0101, and DRB1*0401 respectively, with predicted binding affinities (pIC50 values) of 6.122, 8.067, 6.682, and 6.950 respectively. These HTL epitopes are aligned with the coiled-coil heptad repeat such that they are predicted to form a very strong coiled-coil. The aa(a) and aa(d) core positions of the coiled-coil are occupied by Leu, Leu, Ile, Leu, Ala and Leu, most of them very good residues for high coiled-coil forming propensity with only Ala being somewhat less favorable.

```
RLLAR_LEELERSIWMLQQAAARL_ERAINTVDLELAALRRRLEELAR   (SEQ ID NO: 9)
 d   a d   a d   a d   a d   a d   a d    core residues
```

Consequently the sequence of the peptide is predicted to form a coiled-coil by the prediction program COILS. The coiled-coil forming probability is more than 99% for all the residues of the HTL epitopes in the sequence (Table 19). Comparing the small and large window sizes for coiled-coil prediction shows again the influence of the flanking sequences for the coiled-coil stability. With a window size of 28 amino acids the whole sequence is predicted to form a coiled-coil with a probability of 100% while the smaller window size of 14 amino acids shows the effect of the lower coiled-coil propensity of the T-cell epitopes at the N-terminal end with lower prediction values for coiled-coil formation. Hence for the whole sequence this peptide is predicted to from a stable coiled-coil including the four different HTL epitopes.

TABLE 19

| Coiled-coil propensity of SEQ ID NO: 9 comprising four different HTL epitopes | | |
|---|---|---|
| Amino acid | Window 14 | Window 28 |
| R | 0.443 | 1.000 |
| L | 0.443 | 1.000 |
| L | 0.443 | 1.000 |
| A | 0.529 | 1.000 |
| R | 0.713 | 1.000 |
| L | 0.713 | 1.000 |
| E | 0.713 | 1.000 |
| E | 0.713 | 1.000 |
| L | 0.713 | 1.000 |
| E | 0.713 | 1.000 |
| R | 0.713 | 1.000 |
| S | 0.713 | 1.000 |
| I | 0.713 | 1.000 |
| W | 0.713 | 1.000 |
| M | 0.903 | 1.000 |
| L | 0.947 | 1.000 |
| Q | 0.947 | 1.000 |
| Q | 0.947 | 1.000 |
| A | 0.947 | 1.000 |
| A | 0.947 | 1.000 |
| A | 0.947 | 1.000 |
| R | 0.947 | 1.000 |
| L | 0.947 | 1.000 |
| E | 0.947 | 1.000 |
| R | 0.947 | 1.000 |
| A | 0.947 | 1.000 |
| I | 0.947 | 1.000 |
| N | 0.947 | 1.000 |
| T | 0.947 | 1.000 |
| V | 0.902 | 1.000 |
| D | 0.992 | 1.000 |
| L | 0.992 | 1.000 |
| E | 0.999 | 1.000 |
| L | 0.999 | 1.000 |
| A | 0.999 | 1.000 |
| A | 0.999 | 1.000 |
| L | 0.999 | 1.000 |
| R | 0.999 | 1.000 |
| R | 0.999 | 1.000 |
| R | 0.999 | 1.000 |
| L | 0.999 | 1.000 |
| E | 0.999 | 1.000 |
| E | 0.999 | 1.000 |
| L | 0.999 | 1.000 |
| A | 0.999 | 1.000 |
| R | 0.999 | 1.000 |

This trimeric coiled-coil was then included into the SAPN sequence SEQ ID NO:10 below, composed of a His-tag, the pentameric coiled-coil of COMP, the trimeric coiled-coil of SEQ ID NO:9 and the B-cell epitope from the CS-protein of *Plasmodium berghei*.

```
                                    (SEQ ID NO: 10)
MGHHHHHHGDWKWDGGLVPRGSDEMLRELQETNAALQDVRELLRQQVKQI

TFLRALLMGGRLLARLEELERSIWMLQQAAARLERAINTVDLELAALRRR

LEELARGGSGDPPPPNPNDPPPPNPND
```

Figure 5:
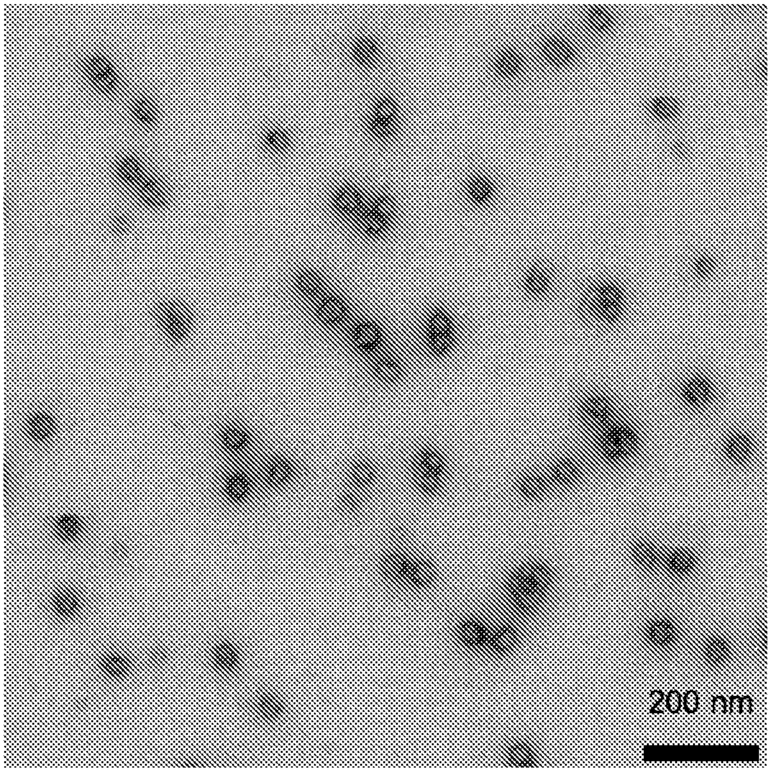
FIG. 5: Transmission electron microscopy (TEM) of the self-assembled peptide nanoparticles formed from peptides with the sequence SEQ ID NO:10, Example 2. The TEM picture shows nanoparticles of the same size of 25 nm.

The peptide with this sequence was expressed in *E. coli* and purified on a nickel affinity column by standard biotechnology procedures. The refolding was performed according to Raman S. et al., Nanomedicine (supra). The refolded SAPN were analyzed for nanoparticle formation by dynamic light scattering (DLS) techniques and transmission electron microscopy (TEM). The DLS analysis showed a nice size distribution with an average particle diameter of 46.96 nm and very low polydispersity index of 8.7%. The TEM pictures (FIG. 5) show nanoparticles of the size of about 30 nm.

Example 3

T1c-7-Influenza

This coiled-coil sequence contains two consecutive HTL epitopes with the sequences IRHENRMVL (SEQ ID NO:228) and YKIFKIEKG (residues 18-26 of SEQ ID NO:11) from the proteins M1 and neuraminidase of the influenza A virus, respectively. By the computer algorithm SVRMHC they are predicted to strongly bind to the MHC II molecules DRB1*0405 and DRB1*0401 with predicted binding affinities (pIC50 values) of 8.250 and 6.985, respectively. Furthermore, according to Panda R. et al., Vaccine 2007, 25:7530-7539, the first T-cell epitope IRHENRMVL (SEQ ID NO:228) is predicted to bind to many other HLA molecules as well such as B14, B1510, B2705, B2706, B3909, DP9, DR11, DR12, DR17, DR53, and DRB1, i.e. it is a predicted promiscuous epitope.

The best alignment of these HTL epitopes with the coiled-coil heptad repeat is shown below (SEQ ID NO:11). However, the sequence of the second of these epitopes contains an unfavorable glycine residue that in general acts as a helix breaking residue. The flanking parts of the coiled-coil trimer are relatively short sequences but have strong coiled-coil forming propensity. When using a small window of 14 amino acids in the coiled-coil prediction program COILS it is visible that coiled-coil structures are predicted for both sides of the T-cell epitopes (see Table 20 below). Hence the whole sequence will again act as a single folding unit and form a stable coiled-coil with a trimeric oligomerization state.

```
RLLARLEEIRHENRMVLYKIFKIEKGINTVDLELAALRRRLEELAR   (SEQ ID NO: 11)

d   a d   a d   a d   a d   a d   a d   a d      core residues
```

TABLE 20

| Coiled-coil propensity of SEQ ID NO: 11 comprising two HTL-epitopes from the influenza A virus | |
|---|---|
| Amino acid | Window 14 |
| R | 0.716 |
| L | 0.716 |
| L | 0.716 |
| A | 0.716 |
| R | 0.716 |
| L | 0.716 |
| E | 0.716 |
| E | 0.716 |
| I | 0.716 |
| R | 0.716 |
| H | 0.716 |

TABLE 20-continued

Coiled-coil propensity of SEQ ID NO: 11 comprising two HTL-epitopes from the influenza A virus

| Amino acid | Window 14 |
|---|---|
| E | 0.716 |
| N | 0.716 |
| R | 0.716 |
| M | 0.256 |
| V | 0.051 |
| L | 0.051 |
| Y | 0.005 |
| K | 0.005 |
| I | 0.004 |
| F | 0.001 |
| K | 0.011 |
| I | 0.011 |
| E | 0.028 |
| K | 0.028 |
| G | 0.028 |
| I | 0.201 |
| N | 0.252 |
| T | 0.467 |
| V | 0.902 |
| D | 0.992 |
| L | 0.992 |
| E | 0.999 |
| L | 0.999 |
| A | 0.999 |
| A | 0.999 |
| L | 0.999 |
| R | 0.999 |
| R | 0.999 |
| R | 0.999 |
| L | 0.999 |
| E | 0.999 |
| E | 0.999 |
| L | 0.999 |
| A | 0.999 |
| R | 0.999 |

This trimeric coiled-coil was then included into the SAPN sequence SEQ ID NO:12 below, composed of a His-tag, the pentameric Trp-zipper coiled-coil, the trimeric coiled-coil as described above and the B-cell epitope from the CS-protein of *Plasmodium berghei*.

```
                                        (SEQ ID NO: 12)
MGHHHHHHGDWKWDGGLVPRGSWQTWNAKWDQWSNDWNAWRSDWQAWKDD

WARWRALWMGGRLLARLEEIRHENRMVLYKIFKIEKGINTVDLELAALRR

RLEELARGGSGDPPPPNPNDPPPPNPND
```

Figure 6:
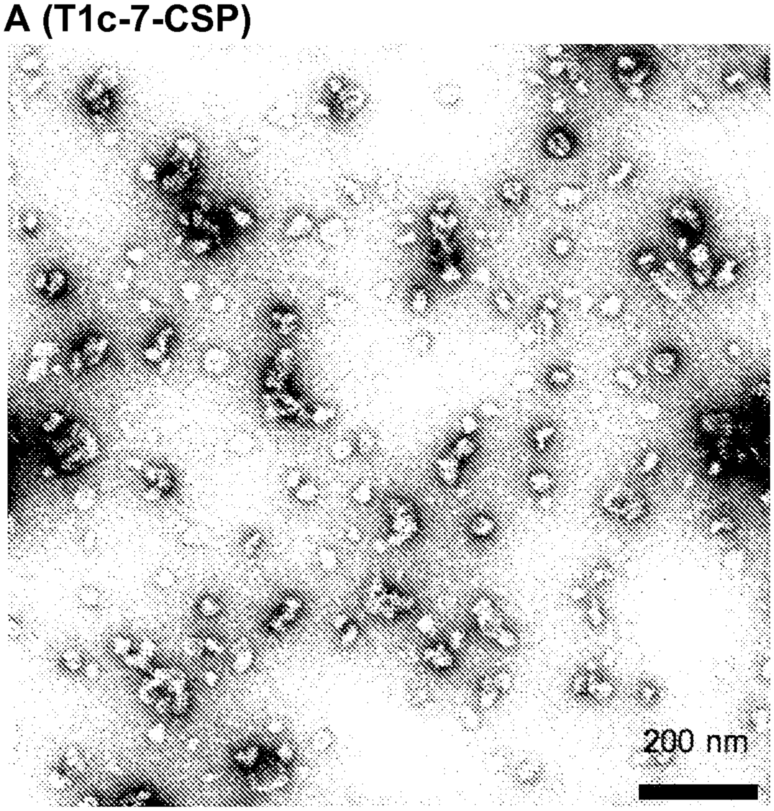
FIG. 6: Transmission electron microscopy (TEM) of the self-assembled peptide nanoparticles formed from peptides with the sequence SEQ ID NO:12, Example 3. The TEM picture shows nanoparticles of the size of about 20 to 30 nm.

The peptide with this sequence was expressed in *E. coli* and purified on a nickel affinity column by standard biotechnology procedures. The refolding was performed according to Raman S. et al., Nanomedicine (supra). The refolded SAPN were analyzed for nanoparticle formation by dynamic light scattering (DLS) techniques and transmission electron microscopy (TEM). The DLS analysis showed a somewhat broader size distribution with an average particle diameter of 57.70 nm and polydispersity index of 21.6%. The TEM pictures (FIG. 6) show nanoparticles of the size of about 30-50 nm.

Some of them have the tendency to stick together and the refolding conditions would need some more improvement.

Example 4

Prediction of Coiled-Coils for Cancer CTL Epitopes

In the following examples it is shown how cancer specific T-cell epitopes can be included into the SAPN forming peptide. 19 different T-cell epitopes are engineered into the trimeric coiled-coil of the SAPN and the corresponding coiled-coil propensities are calculated for the first 10 of these sequences. It is nicely visible that the coiled-coil propensities for the T-cell epitopes are rather low, but the flanking sequences with very high coiled-coil propensities will compensate and induce coiled-coil formation throughout the whole sequence similar as shown for the examples 1 to 3 above.

```
                                        (SEQ ID NO: 13)
WQTWNAKWDQWSNDWNAWRSDWQAWKDDWARWRALWMGGRLLARLEELER
RLEMLLAYLYQLERAINTVDLELAALRRRLEELAR

                                        (SEQ ID NO: 14)
WQTWNAKWDQWSNDWNAWRSDWQAWKDDWARWRALWMGGRLLARLEELER
RLEELLDGTATLRLAINTVDLELAALRRRLEELAR

                                        (SEQ ID NO: 15)
WQTWNAKWDQWSNDWNAWRSDWQAWKDDWARWRALWMGGRLLARLEELER
RLLIYRRRLMKLERAINTVDLELAALRRRLEELAR

                                        (SEQ ID NO: 16)
WQTWNAKWDQWSNDWNAWRSDWQAWKDDWARWRALWMGGRLLARLEELER
RLEILTVILGVLERAINTVDLELAALRRRLEELAR

                                        (SEQ ID NO: 17)
WQTWNAKWDQWSNDWNAWRSDWQAWKDDWARWRALWMGGRLLARLEELER
ELAGIGILTVELERAINTVDLELAALRRRLEELAR

                                        (SEQ ID NO: 18)
WQTWNAKWDQWSNDWNAWRSDWQAWKDDWARWRALWMGGRLLARLEELER
RMSLQRQFLRELERAINTVDLELAALRRRLEELAR

                                        (SEQ ID NO: 19)
WQTWNAKWDQWSNDWNAWRSDWQAWKDDWARWRALWMGGRLLARLEELER
RLEKIFGSLAFLERAINTVDLELAALRRRLEELAR

                                        (SEQ ID NO: 20)
WQTWNAKWDQWSNDWNAWRSDWQAWKDDWARWRALWMGGRLLARLEELER
RLEIISAVVGILERAINTVDLELAALRRRLEELAR

                                        (SEQ ID NO: 21)
WQTWNAKWDQWSNDWNAWRSDWQAWKDDWARWRALWMGGRLLARLEELER
LLHETDSAVEELERAINTVDLELAALRRRLEELAR

                                        (SEQ ID NO: 22)
WQTWNAKWDQWSNDWNAWRSDWQAWKDDWARWRALWMGGRLLARLEELER
ALFDIESKVEELERAINTVDLELAALRRRLEELAR
```

TABLE 21

Coiled-coil propensity of SEQ ID NO: 13 to SEQ ID NO: 22 comprising cancer CTL epitopes

| SEQ ID NO: 13 | | SEQ ID NO: 14 | | SEQ ID NO: 15 | | SEQ ID NO: 16 | | SEQ ID NO: 17 | |
|---|---|---|---|---|---|---|---|---|---|
| aa | Window 14 | aa | Window 14 | aa | Window 14 | aa | Window 14 | aa | Window 14 |
| R | 1.000 | R | 1.000 | R | 0.989 | R | 1.000 | R | 1.000 |
| L | 1.000 | L | 1.000 | L | 0.989 | L | 1.000 | L | 1.000 |
| L | 1.000 | L | 1.000 | L | 0.989 | L | 1.000 | L | 1.000 |

TABLE 21-continued

Coiled-coil propensity of SEQ ID NO: 13 to SEQ ID NO: 22 comprising cancer CTL epitopes

| | | | | | | | | | |
|---|---|---|---|---|---|---|---|---|---|
| A | 1.000 | A | 1.000 | A | 0.989 | A | 1.000 | A | 1.000 |
| R | 1.000 | R | 1.000 | R | 0.989 | R | 1.000 | R | 1.000 |
| L | 1.000 | L | 1.000 | L | 0.989 | L | 1.000 | L | 1.000 |
| E | 1.000 | E | 1.000 | E | 0.989 | E | 1.000 | E | 1.000 |
| E | 1.000 | E | 1.000 | E | 0.989 | E | 1.000 | E | 1.000 |
| L | 1.000 | L | 1.000 | L | 0.989 | L | 1.000 | L | 1.000 |
| E | 1.000 | E | 1.000 | E | 0.989 | E | 1.000 | E | 1.000 |
| R | 1.000 | R | 1.000 | R | 0.989 | R | 1.000 | R | 1.000 |
| R | 1.000 | R | 1.000 | R | 0.989 | R | 1.000 | E | 1.000 |
| L | 1.000 | L | 1.000 | L | 0.989 | L | 1.000 | L | 1.000 |
| E | 1.000 | E | 1.000 | L | 0.989 | E | 1.000 | A | 1.000 |
| M | 0.999 | E | 1.000 | I | 0.948 | I | 0.999 | G | 0.998 |
| L | 0.999 | L | 1.000 | Y | 0.948 | L | 0.999 | I | 0.975 |
| L | 0.999 | L | 1.000 | R | 0.948 | T | 0.999 | G | 0.837 |
| A | 0.999 | D | 1.000 | R | 0.948 | V | 0.992 | I | 0.509 |
| Y | 0.806 | G | 0.996 | R | 0.948 | I | 0.839 | L | 0.169 |
| L | 0.806 | T | 0.716 | L | 0.948 | L | 0.839 | T | 0.102 |
| Y | 0.024 | A | 0.403 | M | 0.855 | G | 0.098 | V | 0.283 |
| Q | 0.547 | T | 0.083 | K | 0.855 | V | 0.087 | E | 0.637 |
| L | 0.547 | L | 0.083 | L | 0.855 | L | 0.289 | L | 0.637 |
| E | 0.547 | R | 0.025 | E | 0.855 | E | 0.289 | E | 0.637 |
| R | 0.547 | L | 0.020 | R | 0.855 | R | 0.289 | R | 0.637 |
| A | 0.547 | A | 0.092 | A | 0.855 | A | 0.289 | A | 0.637 |
| I | 0.547 | I | 0.201 | I | 0.855 | I | 0.289 | I | 0.637 |
| N | 0.547 | N | 0.252 | N | 0.855 | N | 0.289 | N | 0.637 |
| T | 0.547 | T | 0.467 | T | 0.855 | T | 0.467 | T | 0.637 |
| V | 0.902 | V | 0.902 | V | 0.902 | V | 0.902 | V | 0.902 |
| D | 0.992 | D | 0.992 | D | 0.992 | D | 0.992 | D | 0.992 |
| L | 0.992 | L | 0.992 | L | 0.992 | L | 0.992 | L | 0.992 |
| E | 0.999 | E | 0.999 | E | 0.999 | E | 0.999 | E | 0.999 |
| L | 0.999 | L | 0.999 | L | 0.999 | L | 0.999 | L | 0.999 |
| A | 0.999 | A | 0.999 | A | 0.999 | A | 0.999 | A | 0.999 |
| A | 0.999 | A | 0.999 | A | 0.999 | A | 0.999 | A | 0.999 |
| L | 0.999 | L | 0.999 | L | 0.999 | L | 0.999 | L | 0.999 |
| R | 0.999 | R | 0.999 | R | 0.999 | R | 0.999 | R | 0.999 |
| R | 0.999 | R | 0.999 | R | 0.999 | R | 0.999 | R | 0.999 |
| R | 0.999 | R | 0.999 | R | 0.999 | R | 0.999 | R | 0.999 |
| L | 0.999 | L | 0.999 | L | 0.999 | L | 0.999 | L | 0.999 |
| E | 0.999 | E | 0.999 | E | 0.999 | E | 0.999 | E | 0.999 |
| E | 0.999 | E | 0.999 | E | 0.999 | E | 0.999 | E | 0.999 |
| L | 0.999 | L | 0.999 | L | 0.999 | L | 0.999 | L | 0.999 |
| A | 0.999 | A | 0.999 | A | 0.999 | A | 0.999 | A | 0.999 |
| R | 0.999 | R | 0.999 | R | 0.999 | R | 0.999 | R | 0.999 |

| SEQ ID NO: 18 | | SEQ ID NO: 19 | | SEQ ID NO: 20 | | SEQ ID NO: 21 | | SEQ ID NO: 22 | |
|---|---|---|---|---|---|---|---|---|---|
| aa | Window 14 | aa | Window 14 | aa | Window 14 | aa | Window 14 | aa | Window 14 |
| R | 0.997 | R | 1.000 | R | 1.000 | R | 0.981 | R | 0.761 |
| L | 0.997 | L | 1.000 | L | 1.000 | L | 0.993 | L | 0.761 |
| L | 0.997 | L | 1.000 | L | 1.000 | L | 0.993 | L | 0.761 |
| A | 0.997 | A | 1.000 | A | 1.000 | A | 0.993 | A | 0.915 |
| R | 0.997 | R | 1.000 | R | 1.000 | R | 0.993 | R | 0.915 |
| L | 0.997 | L | 1.000 | L | 1.000 | L | 0.993 | L | 0.915 |
| E | 0.997 | E | 1.000 | E | 1.000 | E | 0.993 | E | 0.915 |
| E | 0.997 | E | 1.000 | E | 1.000 | E | 0.993 | E | 0.915 |
| L | 0.997 | L | 1.000 | L | 1.000 | L | 0.993 | L | 0.915 |
| E | 0.997 | E | 1.000 | E | 1.000 | E | 0.993 | E | 0.915 |
| R | 0.997 | R | 1.000 | R | 1.000 | R | 0.993 | R | 0.915 |
| R | 0.997 | R | 1.000 | R | 1.000 | L | 0.993 | A | 0.915 |
| M | 0.997 | L | 1.000 | L | 1.000 | L | 0.993 | L | 0.915 |
| S | 0.997 | E | 1.000 | E | 1.000 | H | 0.993 | F | 0.915 |
| L | 0.963 | K | 1.000 | I | 0.998 | E | 0.993 | D | 0.997 |
| Q | 0.963 | I | 0.999 | I | 0.986 | T | 0.912 | I | 0.997 |
| R | 0.963 | F | 0.983 | S | 0.986 | D | 0.912 | E | 0.997 |
| Q | 0.963 | G | 0.871 | A | 0.986 | S | 0.831 | S | 0.997 |
| F | 0.364 | S | 0.493 | V | 0.812 | A | 0.788 | K | 0.997 |
| L | 0.663 | L | 0.493 | V | 0.605 | V | 0.788 | V | 0.997 |
| R | 0.663 | A | 0.219 | G | 0.040 | E | 0.876 | E | 0.997 |
| E | 0.663 | F | 0.098 | I | 0.085 | E | 0.876 | E | 0.997 |
| L | 0.663 | L | 0.289 | L | 0.289 | L | 0.876 | L | 0.997 |
| E | 0.663 | E | 0.289 | E | 0.289 | E | 0.876 | E | 0.997 |
| R | 0.663 | R | 0.289 | R | 0.289 | R | 0.876 | R | 0.997 |
| A | 0.663 | A | 0.289 | A | 0.289 | A | 0.876 | A | 0.997 |
| I | 0.663 | I | 0.289 | I | 0.289 | I | 0.876 | I | 0.997 |
| N | 0.663 | N | 0.289 | N | 0.289 | N | 0.876 | N | 0.997 |
| T | 0.663 | T | 0.467 | T | 0.467 | T | 0.876 | T | 0.982 |

TABLE 21-continued

Coiled-coil propensity of SEQ ID NO: 13 to SEQ ID NO: 22 comprising cancer CTL epitopes

| | | | | | | | | | |
|---|---|---|---|---|---|---|---|---|---|
| V | 0.902 | V | 0.902 | V | 0.902 | V | 0.902 | V | 0.980 |
| D | 0.992 | D | 0.992 | D | 0.992 | D | 0.992 | D | 0.992 |
| L | 0.992 | L | 0.992 | L | 0.992 | L | 0.992 | L | 0.992 |
| E | 0.999 | E | 0.999 | E | 0.999 | E | 0.999 | E | 0.999 |
| L | 0.999 | L | 0.999 | L | 0.999 | L | 0.999 | L | 0.999 |
| A | 0.999 | A | 0.999 | A | 0.999 | A | 0.999 | A | 0.999 |
| A | 0.999 | A | 0.999 | A | 0.999 | A | 0.999 | A | 0.999 |
| L | 0.999 | L | 0.999 | L | 0.999 | L | 0.999 | L | 0.999 |
| R | 0.999 | R | 0.999 | R | 0.999 | R | 0.999 | R | 0.999 |
| R | 0.999 | R | 0.999 | R | 0.999 | R | 0.999 | R | 0.999 |
| R | 0.999 | R | 0.999 | R | 0.999 | R | 0.999 | R | 0.999 |
| L | 0.999 | L | 0.999 | L | 0.999 | L | 0.999 | L | 0.999 |
| E | 0.999 | E | 0.999 | E | 0.999 | E | 0.999 | E | 0.999 |
| E | 0.999 | E | 0.999 | E | 0.999 | E | 0.999 | E | 0.999 |
| L | 0.999 | L | 0.999 | L | 0.999 | L | 0.999 | L | 0.999 |
| A | 0.999 | A | 0.999 | A | 0.999 | A | 0.999 | A | 0.999 |
| R | 0.999 | R | 0.999 | R | 0.999 | R | 0.999 | R | 0.999 |

The following sequences show likewise a high coiled coil propensity, although the coiled-coil propensities for the T-cell epitopes are rather low, but the flanking sequences with very high coiled-coil propensities will compensate and induce coiled-coil formation throughout the whole sequence.

```
(SEQ ID NO: 23)
WQTWNAKWDQWSNDWNAWRSDWQAWKDDWARWRALWMGGRLLARLEELER
RLSLFRAVITKLERAINTVDLELAALRRRLEELAR

(SEQ ID NO: 24)
WQTWNAKWDQWSNDWNAWRSDWQAWKDDWARWRALWMGGRLLARLEELER
KMVELVHFLEELERAINTVDLELAALRRRLEELAR

(SEQ ID NO: 25)
WQTWNAKWDQWSNDWNAWRSDWQAWKDDWARWRALWMGGRLLARLEELER
RYLQLVFGIEVLERAINTVDLELAALRRRLEELAR

(SEQ ID NO: 26)
WQTWNAKWDQWSNDWNAWRSDWQAWKDDWARWRALWMGGRLLARLEELER
AARAVFLALEELERAINTVDLELAALRRRLEELAR

(SEQ ID NO: 27)
WQTWNAKWDQWSNDWNAWRSDWQAWKDDWARWRALWMGGRLLARLEELER
RLEEQDLTMKYQIFAINTVDLELAALRRRLEELAR

(SEQ ID NO: 28)
WQTWNAKWDQWSNDWNAWRSDWQAWKDDWARWRALWMGGRLLARLEELER
EAYGLDFYILELERAINTVDLELAALRRRLEELAR

(SEQ ID NO: 29)
WQTWNAKWDQWSNDWNAWRSDWQAWKDDWARWRALWMGGRLLARLEELER
RLSYLDSGIHFLERAINTVDLELAALRRRLEELAR

(SEQ ID NO: 30)
WQTWNAKWDQWSNDWNAWRSDWQAWKDDWARWRALWMGGRLLARLEELER
RLEETVSEQSNVERAINTVDLELAALRRRLEELAR

(SEQ ID NO: 31)
WQTWNAKWDQWSNDWNAWRSDWQAWKDDWARWRALWMGGRLLARLEELEE
KLIVVLFRLEELERAINTVDLELAALRRRLEELAR
```

Example 5

HIV-V3

This coiled-coil sequence contains the anti-parallel beta-turn peptide, which is the tip of the V3 loop of gp120 from HIV. This peptide is a well-known B-cell epitope of HIV. It is inserted into the coiled-coil heptad repeat by two glycine residues at positions aa(b) and aa(c) of the coiled-coil.

The flanking parts of the coiled-coil trimer are relatively short sequences but have strong coiled-coil forming propensity. When using a small window of 14 amino acids in the coiled-coil prediction program COILS it is visible that coiled-coil structures are predicted for both sides of the B-cell epitopes (see Table 22 below). Hence the whole sequence will act as a single folding unit and form a stable coiled-coil with a trimeric oligomerization state with a protruding beta-turn peptide.

```
RLLARLEELERRLEELERRLEELERRLGSIRIGPGQTFYAGVDLELAALRRRLEELAR   (SEQ ID NO: 32)
 d   a   d   a   d   a   d   a                d   a   d   a   d   core residues
```

TABLE 22

Coiled-coil propensity of SEQ ID NO: 32 comprising two B-cell epitopes of HIV

| Amino acid | Window 14 |
|---|---|
| R | 1.000 |
| L | 1.000 |
| L | 1.000 |
| A | 1.000 |
| R | 1.000 |
| L | 1.000 |
| E | 1.000 |
| E | 1.000 |
| L | 1.000 |

TABLE 22-continued

Coiled-coil propensity of SEQ ID NO: 32 comprising two B-cell epitopes of HIV

| Amino acid | Window 14 |
|---|---|
| E | 1.000 |
| R | 1.000 |
| R | 1.000 |
| L | 1.000 |
| E | 1.000 |
| E | 1.000 |
| L | 1.000 |
| E | 1.000 |
| R | 1.000 |
| R | 1.000 |
| L | 1.000 |
| E | 1.000 |
| E | 1.000 |
| L | 1.000 |
| E | 1.000 |
| R | 1.000 |
| R | 1.000 |
| L | 1.000 |
| G | 1.000 |
| S | 1.000 |
| I | 0.992 |
| R | 0.969 |
| I | 0.843 |
| G | 0.271 |
| P | 0.000 |
| G | 0.000 |
| Q | 0.004 |
| T | 0.004 |
| F | 0.007 |
| Y | 0.098 |
| A | 0.396 |
| G | 0.611 |
| V | 0.927 |
| D | 0.999 |
| L | 0.999 |
| E | 1.000 |
| L | 1.000 |
| A | 1.000 |
| A | 1.000 |
| L | 1.000 |
| R | 1.000 |
| R | 1.000 |
| R | 1.000 |
| L | 1.000 |
| E | 1.000 |
| E | 1.000 |
| L | 1.000 |
| A | 1.000 |
| R | 1.000 |

Example 6

Analytical Ultracentrifugation of P5c

A peptide of the following sequence (SEQ ID NO:33) is recombinantly expressed in a standard *E. coli* expression system using a His-tag affinity purification scheme:

```
                                           (SEQ ID NO: 33)
MGHHHHHHGDWKWDGGLVPRGSDEMLRELQETNAALQDVRELLRQQVKQI

TFLRALLMGGRLLARLEELERRLEELERRLEELERAINTVDLELAALRRR

LEELAR
```

This sequence is related to the sequences from Examples 1 and 2 (SEQ ID NO:8 and SEQ ID NO:10), but without the C-terminal B-cell epitope. The SAPN formed do not have a disulfide bridge between the two helices (underlined residues 55 and 64, replacement of the two cysteines by alanine as compared to the original design of Raman S. et al., Nanomedicine: Nanotechnology, Biology, and Medicine 2006; 2:95-102) but rather have the smaller amino acid alanine instead, allowing for smaller angles between the two helices, and hence more than 60 peptide chains are incorporated into the SAPN.

Three conditions were tested for assembling nanoparticles from the monomeric building block SEQ ID NO:33. The molecular weight (MW) of the SAPN was assessed by analytical ultracentrifugation: The peptide was dissolved at 0.42 mg/ml, 0.34 mg/ml, and 0.21 mg/ml, in 150 mM NaCl, 20 mM Tris, pH 7.5. The measured MW corresponds to SAPN composed of about 330 monomers, i.e. a nanoparticle with more monomers than needed for a regular polyhedron with 60 asymmetric units (Table 23). The two helices of the two oligomerization domains are not fixed by a disulfide bridge in their relative orientation to each other and the smaller amino acid alanine allows the two helices to get closer and hence the angle between them to be smaller.

TABLE 23

Analytical ultracentrifugation of SEQ ID NO: 33

| Concentration | MW kDa | No. of monomers |
|---|---|---|
| 0.42 mg/ml | 4331 | 344 |
| 0.34 mg/ml | 4128 | 328 |
| 0.21 mg/ml | 4066 | 323 |

Example 7

Trimeric Coiled-Coil with a Series of Overlapping Measured HTL Epitopes (pan3m)

The following is an example of a trimeric coiled-coil design that includes peptide epitopes from Hepatitis B Virus polymerase, which have been measured for their binding affinities to different MHCII molecules (Mizukoshi E. et al., J Immunol 2004, 173:5863-5871). Two of these peptide have sequentially been designed into the trimeric coiled coil according to the principles outlined in this document.

```
RLLARLEELERRLEELQSLTNLLSSNLSWLSLDVSAAFRRLEELEARVM (SEQ ID NO: 34)
 d   a  d   a  d  a   d   a  d   a  d   a  d   a   core residues
```

The measured binding affinities of the peptides contained in the sequence LQSLTNLLSSNLSWLSLDVSAAF (residues 16-38 of SEQ ID NO:34) from the Hepatitis B Virus polymerase for the different MHCII molecules are as follows (binding affinities in nM in brackets): DRB1*0101 (2), DRB1*0301 (62), DRB1*0401 (10), DRB1*0405 (17), DRB1*0701 (173), DRB1*0802 (598), DRB1*0901 (791), DRB1*1101 (303), DRB1*1201 (397), DRB1*1302 (143), DRB1*1501 (21), DRB3*0101 (5), DRB4*0101 (7).

The sequence of the peptide is predicted to form a coiled-coil by the prediction program COILS. The coiled-coil forming probability is more than 98% for all the residues in the sequence (Table 24), therefore the whole sequence is predicted to form a fully folded coiled-coil.

TABLE 24

Coiled-coil propensity of SEQ ID NO: 34

| Amino acid | Window 28 |
|---|---|
| R | 1.000 |
| L | 1.000 |
| L | 1.000 |
| A | 1.000 |
| R | 1.000 |
| L | 1.000 |
| E | 1.000 |
| E | 1.000 |
| L | 1.000 |
| E | 1.000 |
| R | 1.000 |
| R | 1.000 |
| L | 1.000 |
| E | 1.000 |
| E | 1.000 |
| L | 1.000 |
| Q | 1.000 |
| S | 1.000 |
| L | 1.000 |
| T | 1.000 |
| N | 1.000 |
| L | 1.000 |
| L | 1.000 |
| S | 1.000 |
| S | 1.000 |
| N | 1.000 |
| L | 1.000 |
| S | 1.000 |
| W | 1.000 |
| L | 1.000 |
| S | 1.000 |
| L | 1.000 |
| D | 0.999 |
| V | 0.996 |
| S | 0.996 |
| A | 0.996 |
| A | 0.996 |
| F | 0.996 |
| R | 0.996 |
| R | 0.996 |
| L | 0.996 |
| E | 0.996 |
| E | 0.996 |
| L | 0.996 |
| E | 0.996 |
| A | 0.996 |
| R | 0.996 |
| V | 0.996 |
| M | 0.988 |

Example 8

Trimeric Coiled-Coil with a Series of Overlapping Predicted HTL Epitopes (pan3a)

The following is an example of a trimeric coiled-coil design that includes a subsection of the HTL epitopes from SEQ ID NO:34 from (Mizukoshi E. et al., J Immunol 2004, 173:5863-5871) in combination with a sequence that is a subsection of the PADRE HTL epitope sequence.

```
RLLARLEELERRLEELARFVAAWTLKVREVERELSWLSLDVSAAFR   (SEQ ID NO: 35)
 d   a  d   a  d   a  d   a  d   a  d   a  d    core residues
```

The following are the binding affinities as predicted by the algorithm NetMHCII of the epitopes contained in the sequence ARFVAAWTLKVREVERELSWLSLDVSAAF (residues 17-45 of SEQ ID NO:35) for the different MHCII molecules as follows (binding affinities in nM in brackets): DRB1*0101 (23), DRB1*0401 (72), DRB1*0405 (37), DRB1*0701 (164), DRB1*0802 (462), DRB1*0901 (440), DRB1*1101 (271), DRB1*1302 (303), DRB1*1501 (16), DRB3*0101 (60), DRB4*0101 (51). This sequence contains in some part the same epitopes as the sequence pan3m (SEQ ID NO:34), which have in fact shown even stronger binding to the MHCII molecules than predicted by the NetMHCII program (Mizukoshi E. et al., J Immunol 2004, 173:5863-5871).

The sequence of the peptide is predicted to form a coiled-coil by the prediction program COILS. The coiled-coil forming probability is more than 80% for all the residues in the sequence (Table 25) except for the last 8 residues, therefore the sequence is predicted to form a fully folded coiled-coil with the C-terminal end fraying a little bit apart, which will not interfere with SAPN formation as the majority of the sequence at N-terminal end form a coiled-coil.

TABLE 25

| Coiled-coil propensity of SEQ ID NO: 35 | |
|---|---|
| Amino acid | Window 28 |
| R | 1.000 |
| L | 1.000 |
| L | 1.000 |
| A | 1.000 |
| R | 1.000 |
| L | 1.000 |
| E | 1.000 |
| E | 1.000 |
| L | 1.000 |
| E | 1.000 |
| R | 1.000 |
| R | 1.000 |
| L | 1.000 |
| E | 1.000 |
| E | 1.000 |
| L | 1.000 |
| A | 1.000 |
| R | 1.000 |
| F | 1.000 |
| V | 1.000 |
| A | 1.000 |
| A | 1.000 |
| W | 1.000 |
| T | 1.000 |
| L | 1.000 |
| K | 1.000 |
| V | 1.000 |
| R | 1.000 |
| E | 1.000 |
| V | 1.000 |
| E | 1.000 |
| R | 1.000 |
| E | 1.000 |
| L | 1.000 |
| S | 1.000 |
| W | 0.971 |
| L | 0.971 |
| S | 0.838 |
| L | 0.593 |
| D | 0.532 |
| V | 0.206 |
| S | 0.070 |

TABLE 25-continued

| Coiled-coil propensity of SEQ ID NO: 35 | |
|---|---|
| Amino acid | Window 28 |
| A | 0.032 |
| A | 0.011 |
| F | 0.004 |
| R | 0.004 |

Example 9

Tetrameric Coiled-Coil with a Series of Partly Overlapping Predicted HTL Epitopes (BN5c-M2eN)

The tetrameric coiled-coil sequence from tetrabrachion (Stetefeld J. et al., Nature Structural Biology 2000, 7(9):772-776) is characterized by an undecad coiled-coil repeat rather than a heptad repeat. The following is a slightly modified sequence derived from this tetrameric coiled-coil.

```
LYRLTVIIDDRYESLKNLITLRADRLEMIINDNVSTLRALLM (SEQ ID NO: 36)
efghijkabcdefghijkabcdefghijkabcdefghijkab core residues
```

This tetrameric coiled-coil is particularly well-suited as core coiled-coil of the SAPN as it contains a series of overlapping predicted HTL epitopes. The sequences of the epitopes YRLTVIIDD (residues 2-10 of SEQ ID NO:36), LKNLITLRA (residues 15-23 of SEQ ID NO:36), LITLRADRL (residues 18-26 of SEQ ID NO:36), IINDNVSTLR (residues 29-38 of SEQ ID NO:36), INDNVSTLRA (residues 30-39 of SEQ ID NO:36), and VSTLRALLM (residues 34-42 of SEQ ID NO:36) are predicted by the algorithm NetMHCII to bind to the different MHC II molecules DRB1*0101, DRB1*0401, DRB1*0404, DRB1*0405, DRB1*0701, DRB1*1101, DRB1*1302, and DRB1*1501, respectively, with predicted binding affinities (nM) of 3, 48, 78, 162, 243, 478, 12, and 420 respectively.

The tetrameric coiled-coil is also well-suited to present tetrameric B-cell epitopes such as the M2e peptide from influenza, which has been done in the following SAPN design for a human vaccine with the sequence (SEQ ID NO:37):

```
                                           (SEQ ID NO: 37)
MGHHHHHHASLVPRGSLLTEVETPIRNEWGCRCNDSSGSLYRLTVIIDDR

YESLKNLITLRADRLEMIINDNVSTLRALLMGGRLLARLEELERRLEELE

RRLEELERAINTVDLELAALRRRLEELAR
```

Figure 7:
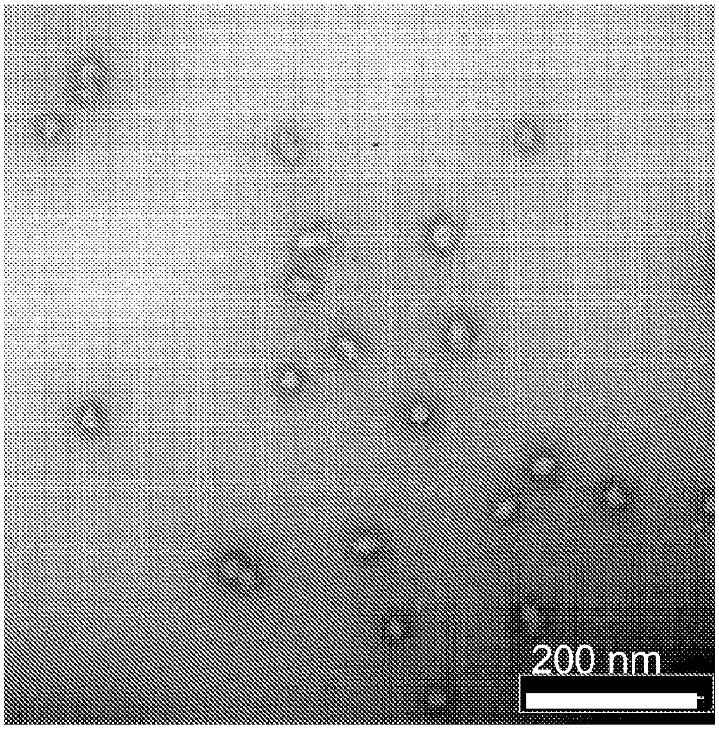
FIG. 7: Transmission electron microscopy (TEM) of the self-assembled peptide nanoparticles formed from peptides with the sequences SEQ ID NO:37 (panel A) and SEQ ID NO:38 (panel B), for a human and a chicken influenza vaccine, respectively (Example 9). The TEM pictures show nanoparticles of the size of about 25 nm.
Figure 7:
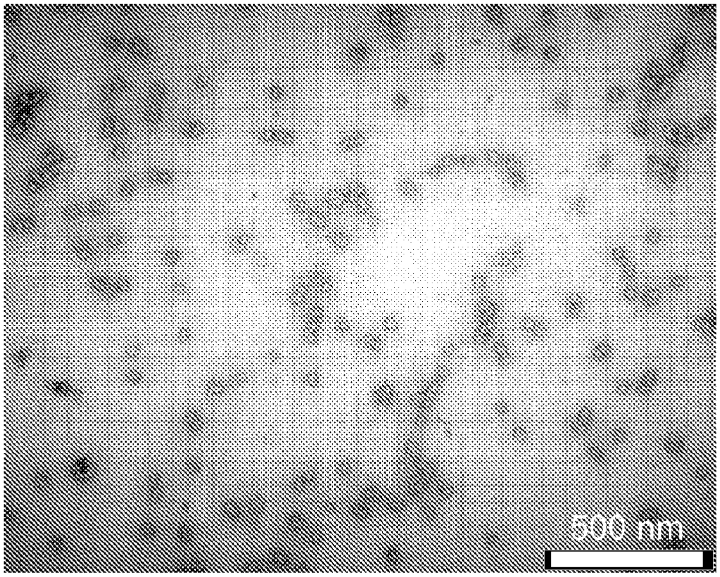

The peptide (SEQ ID NO:37) contains starting from the N-terminus: the His-tag, the M2e B-cell epitope from a human-specific influenza strain, the tetrameric coiled-coil with the HTL epitopes, the linker, and the trimeric coiled-coil. With this sequence it was expressed in *E. coli* and purified on a nickel affinity column by standard biotechnology procedures. The refolding was performed according to Raman S. et al., Nanomedicine: Nanotechnology, Biology, and Medicine 2006; 2:95-102. The refolded SAPN were analyzed for nanoparticle formation by transmission electron microscopy (TEM). The TEM pictures (FIG. 7A) show nanoparticles of the same of about 30 nm.

Also the chicken-specific M2e peptide from influenza can be displayed in its native oligomerization state and conformation as tetramer on the tetrameric coiled-coil of tetrabrachion, which has been done in the following SAPN design for an animal vaccine with the sequence (SEQ ID NO:38):

```
                                           (SEQ ID NO: 38)
MGHHHHHHASLVPRGSLLTEVETPTRNGWECKCSDSSGSLYRLTVIIDDR

YESLKNLITLRADRLEMIINDNVSTLRALLMGGRLLARLEELERRLEELE

RRLEELERAINTVDLELAALRRRLEELAR
```

The peptide with this sequence (SEQ ID NO:38) was expressed in *E. coli* and purified on a nickel affinity column by standard biotechnology procedures. It contains starting from the N-terminus: the His-tag, the M2e B-cell epitope from a chicken-specific influenza strain, the tetrameric coiled-coil with the HTL epitopes, the linker, and the trimeric coiled-coil. The refolding was performed according to Raman S. et al., Nanomedicine: Nanotechnology, Biology, and Medicine 2006; 2:95-102 with the buffer of 20 mM Tris-HCl pH 7.5, 150 mM NaCl and 5% glycerol. The refolded SAPN were analyzed for nanoparticle formation by dynamic light scattering (DLS) techniques and transmission electron microscopy (TEM). The DLS analysis showed a size distribution with an average particle diameter of 45 nm and polydispersity index of 8.9%. The TEM pictures (FIG. 7B) show nanoparticles of the same size of about 30 nm.

Example 10

Pentameric Coiled-Coil with a Series of Overlapping Predicted HTL Epitopes

This sequence is predicted to form an α-helix (H) with high probability (mostly the highest score 9) according to the secondary structure prediction program PSIPRED (The PSIPRED Protein Structure Prediction Server). Since the core positions aa(a) and aa(d) of the heptad repeat of the coiled-coil are mostly tryptophan residues, this sequence is predicted to form a pentameric oiled coil (Liu J et al., Proc Natl Acad Sci USA 2004; 101(46):16156-61).

```
ERFVAAWTLKVAEWEEKWKIWKSLWKAWRLLWM (SEQ ID NO: 39)
   a  d   a  d   a  d   a  d   a  coiled-coil core residues
567899998899899999999999999999994 score for secondary structure
HHHHHHHHHHHHHHHHHHHHHHHHHHHHHHHHH type of secondary structure
```

This pentameric coiled-coil sequence contains partly overlapping HTL epitopes with the sequences FVAAWTLKV (residues 3-11 of SEQ ID NO:39) WKIWKSLWK (residues 18-26 of SEQ ID NO:39) and KSLWKAWRL (residues 22-30 of SEQ ID NO:39) that are predicted by the algorithm NetMHCII to bind to the different MHC II molecules DRB1*0101, DRB1*0401, DRB1*0405, DRB1*0701, DRB1*0801, DRB1*0901, DRB1*1101, DRB1*1501, and DRB5*0101, respectively, with predicted binding affinities (nM) of 24, 73, 13, 120, 42, 596, 396, 6, and 13, respectively.

Example 11

Trimeric Coiled-Coil with a *Plasmodium falciparum* HTL Epitope (t811c-9-pf)

The following is an example of a trimeric coiled-coil design that includes a pan DR binding epitope from *Plasmodium falciparum*. The sequence corresponds to the 17 C-terminal amino acids with two cysteines replaced by alanines, also know as CS.T3 peptide (SEQ ID NO:40) from the circum sporozoite protein CS.

```
RLLLRLEELERRLEELEKKIAKMEKASSVFNVVLAALRRRLEELAR   (SEQ ID NO: 40)
 d   a  d   a  d   a  d   a  d   a  d   a  d    core residues
```

In a cell proliferation assay it has been shown that this CS.T3 peptide had pan DR activity and was stimulatory for DR1, DR2, DR4, DR5, DRw6, DR7 and DR9 molecules (U.S. Pat. No. 5,114,713).

The sequence of the peptide is predicted to form a coiled-coil by the prediction program COILS. The coiled-coil forming probability is more than 99% for all the residues in the sequence (Table 26), except for the last two amino acids. Therefore the whole sequence is predicted to form a fully folded coiled-coil.

TABLE 26

| Coiled-coil propensity of SEQ ID NO: 40 | |
|---|---|
| Amino acid | Window 28 |
| R | 1.000 |
| L | 1.000 |
| L | 1.000 |
| L | 1.000 |
| R | 1.000 |
| L | 1.000 |
| E | 1.000 |
| E | 1.000 |
| L | 1.000 |
| E | 1.000 |
| R | 1.000 |
| R | 1.000 |
| L | 1.000 |
| E | 1.000 |
| E | 1.000 |
| L | 1.000 |
| E | 1.000 |
| K | 1.000 |
| K | 1.000 |
| I | 1.000 |
| A | 1.000 |
| K | 1.000 |
| M | 1.000 |
| E | 1.000 |
| K | 1.000 |
| A | 1.000 |
| S | 1.000 |
| S | 1.000 |
| V | 1.000 |
| F | 1.000 |
| N | 1.000 |
| V | 1.000 |
| V | 1.000 |
| L | 1.000 |
| A | 0.999 |
| A | 0.997 |
| L | 0.997 |
| R | 0.991 |

TABLE 26-continued

| Coiled-coil propensity of SEQ ID NO: 40 | |
|---|---|
| Amino acid | Window 28 |
| R | 0.991 |
| R | 0.991 |
| L | 0.991 |
| E | 0.991 |
| E | 0.991 |
| L | 0.991 |

TABLE 26-continued

| Coiled-coil propensity of SEQ ID NO: 40 | |
|---|---|
| Amino acid | Window 28 |
| A | 0.927 |
| R | 0.927 |

This coiled-coil (SEQ ID NO:40) has been used for the design of a SAPN with the following sequence (SEQ ID NO:41)

```
                                                    (SEQ ID NO: 41)
MGHHHHHHASWKWDGGLVPRGSWQTWNAKWDQWSNDWNAWRSDWQAWKDD

WAFWRALWMGGRLLLRLEELERRLEELEKKIAKMEKASSVFNVVLAALRR

RLEELARGGSGANANPNANPNANPNANP
```

This sequence (SEQ ID NO:41) contains a his-tag, a pentameric coiled-coil tryptophan zipper, a linker, the trimeric coiled-coil SEQ ID NO:40, and a *Plasmodium falciparum* B-cell epitope, which is a tetra-repeat (NANP) of the repetitive sequence of the same circum sporozoite protein CS.

Figure 8:
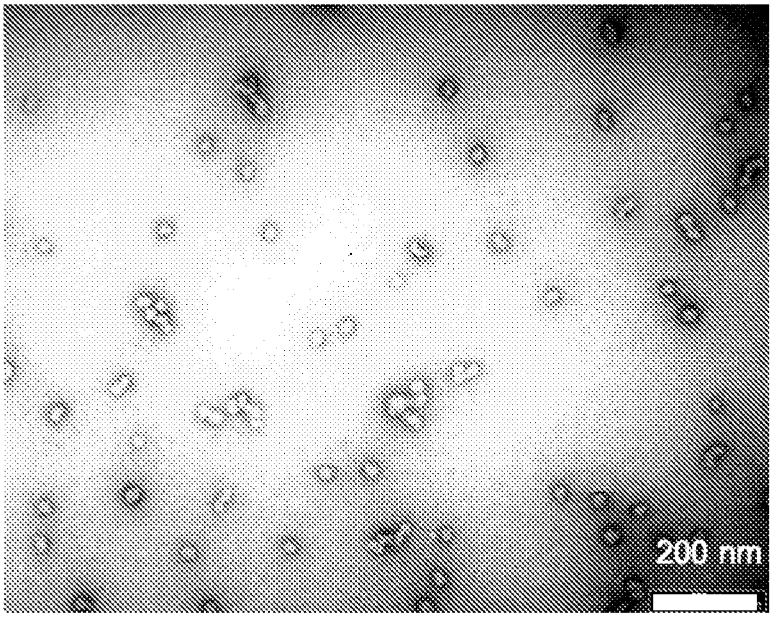
FIG. 8: Transmission electron microscopy (TEM) of the self-assembled peptide nanoparticles formed from peptides with the sequence SEQ ID NO:41, Example 11. The TEM picture shows nanoparticles of the size of about 25 nm.

The peptide with this sequence was expressed in *E. coli* and purified on a nickel affinity column by standard biotechnology procedures. The refolding was performed according to Raman S. et al., Nanomedicine (supra). The refolded SAPN were analyzed for nanoparticle formation by dynamic light scattering (DLS) techniques and transmission electron microscopy (TEM). The DLS analysis at pH 6.5 showed a size distribution with an particle diameter of 44.6 nm and a polydispersity index of 19.6%. The TEM pictures (FIG. 8) show nanoparticles of the size of about 30 nm.

Example 12

HIV Vaccine: HTL, CTL, B-Cell Co-Assembly

The following is an example of an HIV vaccine design. These conserved protein sequences contain CTL epitopes predicted to bind to the HLA molecules as listed in Table 10.

(SEQ ID NO: 42)
ELDKWASLWNWFNITNWLWYIRSWQTWNAKWDQWAKFIAAWTLKVAAWKDDWARWRALWMGGRLLLRL

EELERRLEELEKKIAKMEKASSVFNVVLAALRRRLEELARPLDEGFRKYTAFTIPSINNE (SEQ ID NO: 43)
ELDKWASLWNWFNITNWLWYIRSWQTWNAKWDQWAKFIAAWTLKVAAWKDDWARWRALWMGGRLLLRL

EELERRLEELEKKIAKMEKASSVFNVVLAALRRRLEELARKGPAKLLWKGEGAVFIHNFKRKGGIGG (SEQ ID NO: 44)
ELDKWASLWNWFNITNWLWYIRSWQTWNAKWDQWAKFIAAWTLKVAAWKDDWARWRALWMGGRLLLRL

EELERRLEELEKKIAKMEKASSVFNVVLAALRRRLEELARIIGRNLLTQIGCTLNFPISPIETVPV (SEQ ID NO: 45)
ELDKWASLWNWFNITNWLWYIRSWQTWNAKWDQWAKFIAAWTLKVAAWKDDWARWRALWMGGRLLLRL

EELERRLEELEKKIAKMEKASSVFNVVLAALRRRLEELARDFWEVQLGIPHPAGLKKKKSV (SEQ ID NO: 46)
ELDKWASLWNWFNITNWLWYIRSWQTWNAKWDQWAKFIAAWTLKVAAWKDDWARWRALWMGGRLLLRL

EELERRLEELEKKIAKMEKASSVFNVVLAALRRRLEELARLTEEAELELAENREILKDPVHGV (SEQ ID NO: 47)
ELDKWASLWNWFNITNWLWYIRSWQTWNAKWDQWAKFIAAWTLKVAAWKDDWARWRALWMGGRLLLRL

EELERRLEELEKKIAKMEKASSVFNVVLAALRRRLEELARLVSQGIRKVLFLDGIDK

The first seven CTL peptide-strings of Table 10 are engineered at the C-terminal end of the six peptide chains with identical core and identical N-terminal B-cell epitope and hence are co-assembled into a single SAPN.

The core contains the same trimer as in Example 11 with a promiscuous *P. falciparum* HTL epitope, linked to a Trp-zipper pentameric coiled-coil which contains a PADRE HTL epitope.

The B-cell epitope is the membrane proximal region of GP41, which has neutralizing potential as evidenced by binding of the monoclonal neutralizing antibodies 2F5 and 4E10. This epitope is α-helical in solution and is held in α-helical conformation by being partly engineered into the pentameric coiled-coil. In this design the surface accessible residues (i.e. the residues that are not the coiled-coil core residues) are the ones that are bound by the antibody 4E10.

Example 13

Malaria Vaccine: HTL-CTL-B-Cell-Core, B-Cell, CTL Co-Assembly

The following is an example of an malaria vaccine SAPN composed of six peptide chains with an identical core and an identical C-terminal B-cell epitope and about 18 CTL epitopes at the N-terminus (three each per peptide chain) co-assembled into a single SAPN.

(SEQ ID NO: 48)
KPNDKSLYKPKDELDYEAKPIVQYDNFMNGSERFVAAWTLKVAEWEEKWKIWKSLWKAWRLLWMGGRL

LLRLEELMEKLKELEKKLRNLEEELHSLRKNLNILNEELEELTRGGSGANANPNANPNANPNANP (SEQ ID NO: 49)
ASKNKEKALIIAAGIAGGLALLRSLLMDCSGSIGSERFVAAWTLKVAEWEEKWKIWKSLWKAWRLLWMG

GRLLLRLEELMEKLKELEKKLRNLEEELHSLRKNLNILNEELEELTRGGSGANANPNANPNANPNANP (SEQ ID NO: 50)
MNPNDPNRNVQQMPNDPNRNVQQKSLYDEHIGSERFVAAWTLKVAEWEEKWKIWKSLWKAWRLLWMGG

RLLLRLEELMEKLKELEKKLRNLEEELHSLRKNLNILNEELEELTRGGSGANANPNANPNANPNANP (SEQ ID NO: 51)
MINAYLDKLRAISKYEDEIFAHLGNVKYLVGSERFVAAWTLKVAEWEEKWKIWKSLWKAWRLLWMGGR

LLLRLEELMEKLKELEKKLRNLEEELHSLRKNLNILNEELEELTRGGSGANANPNANPNANPNANP (SEQ ID NO: 52)
ENDIEKKIAKMEKASKSLYDEHILLMDCSGSIGSERFVAAWTLKVAEWEEKWKIWKSLWKAWRLLWMG

GRLLLRLEELMEKLKELEKKLRNLEEELHSLRKNLNILNEELEELTRGGSGANANPNANPNANPNANP (SEQ ID NO: 53)
KSKDELDYEAIPSLALMLIMPLETQLAIGSERFVAAWTLKVAEWEEKWKIWKSLWKAWRLLWMGGRLL

LRLEELMEKLKELEKKLRNLEEELHSLRKNLNILNEELEELTRGGSGANANPNANPNANPNANP

The core (underlined) is a combination of a trimeric coiled-coil that contains a CTL epitope MEKLKELEK (residues 75-83 of SEQ ID NO:53) and the modified B-cell epitope KLRNLEEELHSLRKNLNILNEELEELT (residues 84-110 of SEQ ID NO:53) (sequence 27 in Villard V. et al., PLoS ONE 2007, 2(7):e645), and the pentamer shown in Example 10 with excellent panDR binding properties. At the C-terminal all six peptide chains have the identical B-cell epitope, which is a tetra-repeat (NANP) of the repetitive sequence of the circum sporozoite protein CS from *Plasmodium falciparum*. At the N-terminus are about 18 different *P. falciparum* CTL epitopes (U.S. Pat. Nos. 5,028,425, 5,972,351, 6,663,871) three different epitopes per chain. The CTL-epitopes are separated by optimized proteasomal cleavage sites (Hadeler K. P. et al., Math. Biosci. 2004, 188:63-79). Since the core of these six peptide chains is identical, co-assembly of these six peptide chains into one single SAPN allows the incorporation of about 18 different CTL epitopes into one single SAPN.

Example 14

Influenza Vaccine: HTL-Core, B-Cell Tetramer, CTL, Co-Assembly

The following is an example of an Influenza vaccine SAPN composed of six peptide chains with an identical core and identical N-terminal B-cell epitope M2e and about 20 CTL epitopes at the C-terminus (three or four each per peptide chain) co-assembled into a single SAPN. The core (underlined) is a combination of the trimer in Example 7 and the tetramer in Example 9 with excellent panDR binding properties. The tetrameric N-terminal B-cell epitope is the same as in Example 9. At the C-terminal end the conserved CTL epitopes from Parida R. et al., Vaccine 2007, 25:7530-7539 (Table 15) are placed. Since the core of these six peptide chains is identical, co-assembly of these six peptide chains into one single SAPN allows the incorporation of about 20 different CTL epitopes into one single SAPN.

(SEQ ID NO: 54)
SLLTEVETPIRNEWGCRCNDSSGSLYRLTVIIDDRYESLKNLITLRADRLEMIINDNVSTLRALLM
GGRLLARLEELERRLEELQSLTNLLSSNLSWLSLDVSAAFRRLEELEARVIRHENRMVLQAYQKRM
GVLKMPASRYLSRYLTDMTL (SEQ ID NO: 55)
SLLTEVETPIRNEWGCRCNDSSGSLYRLTVIIDDRYESLKNLITLRADRLEMIINDNVSTLRALLM
GGRLLARLEELERRLEELQSLTNLLSSNLSWLSLDVSAAFRRLEELEARVFMLMPKQKVMRMGDFH
SLYLLAWKQVL (SEQ ID NO: 56)
SLLTEVETPIRNEWGCRCNDSSGSLYRLTVIIDDRYESLKNLITLRADRLEMIINDNVSTLRALLM
GGRLLARLEELERRLEELQSLTNLLSSNLSWLSLDVSAAFRRLEELEARVAPIEHIASMRRNYFTA
EVIQMCTELKL (SEQ ID NO: 57)
SLLTEVETPIRNEWGCRCNDSSGSLYRLTVIIDDRYESLKNLITLRADRLEMIINDNVSTLRALLM
GGRLLARLEELERRLEELQSLTNLLSSNLSWLSLDVSAAFRRLEELEARVAAGAAVKGVVGTMVME
LINPTLLFLKV (SEQ ID NO: 58)
SLLTEVETPIRNEWGCRCNDSSGSLYRLTVIIDDRYESLKNLITLRADRLEMIINDNVSTLRALLM
GGRLLARLEELERRLEELQSLTNLLSSNLSWLSLDVSAAFRRLEELEARVRLIDFLKDVMQIRGFV
YFIMFSNKMARL (SEQ ID NO: 59)
SLLTEVETPIRNEWGCRCNDSSGSLYRLTVIIDDRYESLKNLITLRADRLEMIINDNVSTLRALLM
GGRLLARLEELERRLEELQSLTNLLSSNLSWLSLDVSAAFRRLEELEARVERNEQGQTLVAYMLER
ELLRHFQKDAKVRDQRGNVL

Example 15

Influenza Vaccine: HTL-Core, B-Cell Tetramer, Cleavage Peptide Co-Assembly

The following is an example of an Influenza vaccine SAPN composed of three peptide chains with an identical core and identical N-terminal B-cell epitope M2e and nine B-cell epitopes at the C-terminus (three each per peptide chain) co-assembled into a single SAPN.

(SEQ ID NO: 60)
SLLTEVETPIRNEWGCRCNDSSGSLYRLTVIIDDRYESLKNLITLRADRL
EMIINDNVSTLRALLMGGRLLARLEELERRLEELAKFVAAWTLKVREVER
ELSWLSLDVSAAFLERKKRGLFGDIQSRGLFGDERQTRGIFG (SEQ ID NO: 61)
SLLTEVETPIRNEWGCRCNDSSGSLYRLTVIIDDRYESLKNLITLRADRL
EMIINDNVSTLRALLMGGRLLARLEELERRLEELAKFVAAWTLKVREVER
ELSWLSLDVSAAFLERKTRGLFGDPKGRGLFGDQIESRGLFG

-continued (SEQ ID NO: 62)

SLLTEVETPIRNEWGCRCNDSSGSLYRLTVIIDDRYESLKNLITLRADRL

EMIINDNVSTLRALLMGGRLLARLEELERRLEELAKFVAAWTLKVREVER

ELSWLSLDVSAAFLEKKGRGLFGDASYRGLFGDKREKRGLFG

The core (underlined) is a combination of the trimer in Example 8 and the tetramer in Example 9 with excellent pan DR binding properties. The tetrameric N-terminal B-cell epitope is the same as in Example 9. The C-terminal B-cell epitopes are from Table 8 for H1, H2, H3, H5 consensus 1, H5 consensus 2, H7 consensus 1, H7 consensus 2, H7 consensus 3, H9 with negative charges between the epitopes to make the B-cell epitope string less positively charged.

The invention claimed is:

1. A self-assembling peptide nanoparticle consisting of aggregates of a multitude of building blocks of formula (I) consisting of a continuous chain comprising a peptidic oligomerization domain D1, a linker segment L, and a peptidic oligomerization domain D2

D1-L-D2 (I), wherein D1 is a peptide having a tendency to form oligomers $(D1)_m$ of m subunits D1, D2 is a peptide having a tendency to form oligomers $(D2)_n$ of n subunits D2, m and n each is a figure between 2 and 10, with the proviso that m is not equal n and not a multiple of n, and n is not a multiple of m, L is a bond or a short linker segment consisting of 1 to 6 amino acids, either D1 or D2 or both D1 and D2 is a coiled-coil oligomerization domain that incorporates one or more T- and/or B-cell epitopes within the oligomerization domain, wherein at least one of the epitopes is a helper T lymphocyte epitope (HTL epitope), and wherein D1 and/or D2 are unsubstituted or further substituted at the free end of the oligomerization domain D1 and/or D2.

2. The peptide nanoparticle according to claim 1 wherein the peptidic oligomerization domain D1 at its N-terminal end and/or the peptidic oligomerization domain D2 at its C-terminal end is substituted by one or more additional B- and/or T-cell epitope, one or more other peptide or protein, or one or more additional hapten.

3. The peptide nanoparticle according to claim 2 of the formulae S1-D1-L-D2, D1-L-D2-S2, or S1-D1-L-D2-S2, wherein S1 and S2 are peptidic substituents.

4. The peptide nanoparticle according to claim 2, consisting of identical building blocks D1-L-D2, wherein at least one of the identical building blocks carries one or more different substituent at the N-terminal end of D1 and/or the C-terminal end of D2.

5. A composition comprising a peptide nanoparticle according to claim 1.

6. A monomeric building block of formula (I) consisting of a continuous chain comprising a peptidic oligomerization domain D1, a linker segment L, and a peptidic oligomerization domain D2

D1-L-D2 (I), wherein D1 is a peptide having a tendency to form oligomers $(D1)_m$ of m subunits D1, D2 is a peptide having a tendency to form oligomers $(D2)_n$ of n subunits D2, m and n each is a figure between 2 and 10, with the proviso that m is not equal n and not a multiple of n, and n is not a multiple of m, L is a bond or a short linker segment consisting of 1 to 6 amino acids, either D1 or D2 or both D1 and D2 is a coiled-coil oligomerization domain that incorporates one or more T- and/or B-cell epitopes within the oligomerization domain, wherein at least one of the epitopes is a helper T lymphocyte epitope (HTL epitope), and wherein D1 and/or D2 are unsubstituted or further substituted at the free end of the oligomerization domain D1 and/or D2.

* * * * *